US010982171B2

(12) United States Patent
Vetcher et al.

(10) Patent No.: US 10,982,171 B2
(45) Date of Patent: Apr. 20, 2021

(54) METHODS FOR OIL DEGUMMING

(71) Applicant: Keclon SA, Rosario (AR)

(72) Inventors: Leandro Vetcher, Cambridge, MA (US); Salvador Peiru, Rosario (AR); Maria Eugenia Castelli, Rosario (AR); Hugo Gabriel Menzella, Rosario (AR)

( * ) Notice: Subject to any disclaimer, the term of this patent is extended or adjusted under 35 U.S.C. 154(b) by 408 days.

(21) Appl. No.: 15/737,413

(22) PCT Filed: Jul. 18, 2016

(86) PCT No.: PCT/US2016/042844

§ 371 (c)(1),
(2) Date: Dec. 18, 2017

(87) PCT Pub. No.: WO2017/015233

PCT Pub. Date: Jan. 26, 2017

(65) Prior Publication Data

US 2018/0251704 A1 Sep. 6, 2018

Related U.S. Application Data

(60) Provisional application No. 62/194,018, filed on Jul. 17, 2015.

(51) Int. Cl.

| | |
|---|---|
| ***C11B 3/00*** | (2006.01) |
| ***C12P 7/64*** | (2006.01) |
| ***C11C 1/04*** | (2006.01) |
| ***C12N 9/16*** | (2006.01) |
| ***C12P 3/00*** | (2006.01) |
| ***A23D 9/02*** | (2006.01) |
| ***C12N 9/10*** | (2006.01) |

(52) U.S. Cl.

CPC ................ *C11B 3/003* (2013.01); *A23D 9/02* (2013.01); *C11C 1/045* (2013.01); *C12N 9/1025* (2013.01); *C12N 9/16* (2013.01); *C12P 3/00* (2013.01); *C12P 7/649* (2013.01); *C12P 7/6418* (2013.01); *Y02E 50/10* (2013.01)

(58) Field of Classification Search

CPC .......... A23D 9/02; C12N 9/1025; C12N 9/16; C11C 1/045; C12P 3/00; C12P 7/6418; C12P 7/649; Y02E 50/13; C11B 3/003

See application file for complete search history.

(56) References Cited

U.S. PATENT DOCUMENTS

| | | | |
|---|---|---|---|
| 2005/0108789 | A1 | 5/2005 | Gramatikova |
| 2007/0298157 | A1 | 12/2007 | Soe |
| 2008/0305531 | A1 | 12/2008 | Lam |
| 2011/0136187 | A1 | 6/2011 | Soe |
| 2013/0011887 | A1 | 1/2013 | Dayton |
| 2014/0227747 | A1 | 8/2014 | Yukawa |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Pena-Montenegro et al., GenBank accession No. EON73549, May 10, 2013.*
Dallagassa et al., GenBank accession No. KXU80004, Mar. 2016.*
ISR from WO2017015233, Oct. 20, 2016.
Written Opinion from WO2017015233, dated Oct. 20, 2016.

* cited by examiner

*Primary Examiner* — Delia M Ramirez

(74) *Attorney, Agent, or Firm* — Patent GC; Naomi S. Biswas

(57) ABSTRACT

The present disclosure provides compositions and methods for enzymatic oil degumming.

6 Claims, 10 Drawing Sheets

Specification includes a Sequence Listing.

| | Mean | Std dev |
|---|---|---|
| H2O | 7,15 | 0,17 |
| PC/PE-PLC | 6,13 | 0,28 |
| PC/PE-PLC+PI-PLC+LAT | 5,01 | 0,22 |

METHODS FOR OIL DEGUMMING

RELATED APPLICATIONS

This application claims the benefit of priority of U.S. provisional application 62/194,018, filed Jul. 17, 2015.

INCORPORATION BY REFERENCE

All publications, patents, and patent applications mentioned in this specification are hereinincorporated by reference to the same extent as if each individual publication, patent, or patent application was specifically and individually indicated to be incorporated by reference.

BACKGROUND OF THE INVENTION

With the increasing need for food, cosmetics, and ecologically responsible fuels it is important to optimize the processing of crude oils for high yield and stability. In particular, there is a need for cost effective and efficient methods for removing phospholipids and lecithins, known collectively as "gums", from oil compositions (edible oils, crude oil etc.) to produce a degummed oil product that can be used for consumer products such as food or fuel.

As explained in detail by W. van Nieuwenhuyzen, "Lecithin production and properties" in Journal of the American Oil Chemists' Society (1976) 53: 425-427, lecithin is a complex mixture of phosphatides (such as phosphatidyl choline, phosphatidyl ethanolamine, phosphatidyl inositol and phosphatidic acid), their lyso-compounds, triglycerides, sugars (such as saccharose, raffinose and stachyose), some glycolipids and further minor constituents, wherein lecithin normally contains some 35% by weight triglyceride oil.

Owing to the variety of impurities in a crude oil, a series of chemical and physical methods can be employed to remove undesirable impurities that affect the stability, quality of performance, taste, smell, or color of an oil. More recently, developments were made to use enzymatic degumming.

Enzymatic degumming has several advantages over chemical and physical methods such as lower costs, minimal chemical waste, and higher yields of refined oil.

Francis Turner in chapter 5 "Degumming", book *Edible Oil Processing from a Patent Perspective*, Albert Dijkstra, Ed. Springer; makes a summary of the state of art since 1990 about the different methods of degumming developed by the principal players in this field. (Chapter 5, *"Degumming"*, p 121-155, A. J. Dijkstra, *Edible Oil Processing from a Patent Perspective*, Springer Science+Business Media, LLC 2013), this documents is incoporated herein as a reference. Several enzymatic oil degumming technologies have been developed in last years. Some of them are disclosed in patents like: U.S. Pat. Nos. 9,228,211B2, 7,906,307B2, 9,315,764, U.S. Pat. Appl. No. 20120210467; U.S. Pat. Nos. 8,541,211 and 8,241,876.

U.S. Pat. No. 9,228,211B2 discloses a process of water degumming of an edible oil (preferably a crude edible oil) comprising the steps of admixing edible oil (preferably a crude edible oil) and a lipid acyltransferase, under particular conditions. In a particular embodiment, the lipid acyltransferase (LAT) can be used in combination with a phospholipase C enzyme. This patent shows that the best results are reached using the lipid acyltransferase in a concentration of 0.5 TIPU/gr of oil, resulting in a reduction of the gum phase. The patent explains that "the addition of lipid acyltransferase to crude oil catalyses the transfer of fatty acid moiety from phospholipid to sterol, during formation of sterol esters". On a molecular level the amount of sterol is less than ⅓ of the amount of phospholipids in crude soya oil. Because the acyl acceptor sterol is the limiting factor for KLM3' in crude soya oil, the hydrolysis reaction might occur depending on enzyme dosage and reaction time". So it was found that the addition of more sterol to the crude oil produces more sterol ester, when the oil is treated with lipid acyltransferase KLM3', and the amount of free fatty acids formed is reduced compared with an oil where no sterol was added. This document shows that enzymatic degumming using LAT (at the recommended dose of 0.1-1 TIPU/g of oil) increases the free fatty acid content of oil. As the acyl acceptor sterol is the limiting factor for LAT in crude soybean oil, the hydrolysis reaction occurs. The alternative of adding 0.25-0.75% sterol is not economically viable and impracticable for an industrial process. Also, in the examples using LAT in combination with PLC the content of diglyceride is reduced compared to the PLC treatment alone.

U.S. Pat. No. 7,696,369 discloses a process for recuperating trigliceride oil from wet gums obtained from water degumming of a vegetable oil, mixing these gums with a phospholipidolytic agent. Such phospholipidolytic agent can be a phospholipase. The patent discloses the use of Novozyme's Lecitase® Ultra (PLA) for wet gums treatment, and describes a process in Example 7 using 250 mg of the enzyme per kg dry gum matter. Not only the amounts of enzyme required for the process are about 100-fold higher than the amount required for a crude oil degumming treatment for an equivalent amount of phospholipids, but also the data provided result from a 5 days long treatment. Therefore, such process could not be used in the crushing industry.

U.S. Pat. No. 9,315,764 discloses methods of processing lipid material such as soapstock, dry gums and wet gums, where enzymes are utilized to catalyze hydrolysis of the lipids materials to recover fatty acids. Examples provided for treatment of wet gums involve the use of 2% Phospholipase A2 in a 20 hrs treatment, reaching 30% oil yield. Such amounts of enzyme and duration of the process are too high to be implemented as a profitable process in the crushing industry.

BRIEF SUMMARY OF THE INVENTION

The present disclosure relates to compositions and methods for an oil degumming. In first aspect, the present invention relates to a method for degumming an oil composition, that can be vegetable oil or gum from vegetal oil, containing between 1 and 40% w/w of phospholipids and 1-30% w/w water, comprising: contacting the oil composition with an enzymatic mixture, wherein the enzymatic mixture comprises a phosphatidylinositol-specific phospholipase activity; a phosphatidylcholine and phosphatidylethanolamine-specific phospholipase activity; and a lipid acyltransferase; wherein the concentration of lysophospholipid and free fatty acids are maintained at about their initial levels.

In this method the lipid acyltransferase is an enzymatic stabilizer of the other enzymes, and produces an increase of the half life time of the other components of the enzymatic mixture, particularly the lipid acyltransferse increase the half life time of the polypeptides that has phosphatidylinositol-specific phospholipase activity, a phosphatidylcholine and phosphatidylethanolamine-specific phospholipase activity.

In some embodiments of the method, the lipid acyltransferase is a phosphatidylcholine-sterol O-acyltransferase.

This lipid acyltransferase is used in the present invention at a concentration between 1/10 and 1/100 of the recommended concentration for oil degumming (this state of the art concentration is between 0.1 to 0.5 TIPU/g of oil), wherein said acyltransferase stabilizes the activity of a phosphatidylinositol-specific phospholipase and a phosphatidylcholine and phosphatidylethanolamine-specific phospholipase when the phospholipases enzymes react with the oil composition. In some embodiments the enzymatic mixture can hydrolyze greater than 60%, 70%, 80%, or 90% (w/w) of phospholipids present in the oil composition into a diacylglycerol and a phosphate ester. In some embodiments of the method, the method results in increasing the oil yield by at least 1.0%, 1.5%, 2.0%, 2.5%, 3.0%, 3.5%, 4.0%, 4.5% or more compared to a non-enzymatic degumming method. Preferably, the method results in increasing the oil yield by up to 40% compared to a non-enzymatic degumming method.

In some embodiments, the method does not comprise a phospholipase A. In some embodiments of the method, the free fatty acid content in the oil composition does not increase. In some embodiments of the method, the lysophospholipids content in the oil composition does not increase. In some embodiments, the method can reduce greater than 60%, 70%, 80%, or 90% of the mass of the gums in the oil composition. In some embodiments, the phosphatidylinositol-specific phospholipase activity, and the phosphatidylcholine and phosphatidylethanolamine-specific phospholipase activity is maintained at 80-90% activity level during the method. In some embodiments of the method the phosphatidylinositol-specific phospholipase activity or the phosphatidylcholine and phosphatidylethanolamine-specific phospholipase activity is higher compared to an enzymatic oil degumming method without a lipid acyltransferase. In some embodiments, the total enzymatic activity from the phosphatidylinositol-specific phospholipase and the phosphatidylcholine and phosphatidylethanolamine-specific phospholipase is at least 10%, 20%, 30%, 40%, or 50% higher compared to an enzymatic degumming method without lipid acyltransferase. In some embodiments of the method the lipid acyltransferase is used at no more than one tenth of the recommended concentration for an enzymatic oil degumming method. In some embodiments of the method, the concentration of the lipid acyltransferase enzyme is not greater than 0.01 TIPU/g oil. In some embodiments of the method, the concentration of the lipid acyltransferase enzyme is not greater than 0.06 TIPU/g oil. In some embodiments of the method, the concentration of the lipid acyltransferase enzyme is not greater than 0.05 TIPU/g oil. In some embodiments, the concentration of the lipid acyltransferase enzyme is about 0.01 TIPU/g oil. In some embodiments, the concentration of the lipid acyltransferase enzyme is about 0.001 TIPU/g oil. In some embodiments, the concentration of the lipid acyltransferase enzyme is about 0.06 TIPU/g oil. In some embodiments, the concentration of the lipid acyltransferase enzyme is about 0.008 TIPU/g oil. In some embodiments of the method the enzyme that imparts lipid acyltransferase has at least 80% identity to SEQ ID NO: 6, 7, 8, 9, or 10. In some embodiments of the method the enzyme that imparts lipid acyltransferase has at least 80% identity to SEQ ID NO: 10. In some embodiments of the method, the enzyme that provides phosphatidylinositol-specific phospholipase activity and has at least 80% identity to SEQ ID NO: 1, 2, 3, or 4. In some embodiments, the enzyme that imparts phosphatidylcholine and phosphoethanolamine-specific phospholipase activity and has at least 85% identity to SEQ ID NO: 5. In some embodiments of the method, the oil composition is an edible oil. In some embodiments of the method, the edible oil is a soybean, a rapeseed, a sunflower seed, a rice bran, a sesame, a corn, a palm, a sesame, or a peanut oil, or a combination thereof. In some embodiments of the method, the oil composition is a crude oil. In some embodiments of the method, the oil composition is a wet gum which is contacted with said enzymatic mixture for a time of at least 4 hs, and more than 70% of the total phospholipids present in the initial wet gum is hydrolysed; the oil gain is at least 34 g of oil recovered per 100 g of treated gum; the phosphatidylinositol-specific phospholipase activity is provided by an enzyme that comprises at least 80% identity to SEQ ID NO: 1, 2, 3, or 4, in a concentration lower than 80 ug/g of oil; the phosphatidylcholine and phosphatidylethanolamine-specific phospholipase activity is provided by an enzyme that has at least 85% identity to SEQ ID NO: 5, in a concentration lower than 40 ug/g of oil; and the lipid acyltransferase has at least 80% identity to SEQ ID NO: 10, in a concentration lower than 1.6 ug/g. In some embodiments of the method, the phosphatidylinositol-specific phospholipase activity is provided by an enzyme that has at least 80% identity to SEQ ID NO: 1, 2, 3, or 4 and wherein the weight relationship between said phosphatidylinositol-specific phospholipase, and said lipid acyltransferase as an enzymatic stabilizer is 50:1.

In second aspect, the present disclosure relates to an edible oil for a consumer product made by the method of any one of the methods provided by the present disclosure.

In third aspect, the present disclosure relates to a biofuel made by any one of the methods provided by the present disclosure.

In fourth aspect, the present disclosure relates to an oil for a consumer product comprising detectable amounts of a polypeptide with at least 80% sequence identity to SEQ ID NO: 1, 2, 3, or 4.

In fifth aspect, the present disclosure relates to an oil for a consumer product comprising detectable amounts of a polypeptide with at least 80% identity to SEQ ID NO: 6, 7, 8, 9, or 10.

In sixth aspect, the present disclosure relates to a vector comprising: a polynucleotide encoding a polypeptide having phosphodiesterase activity, wherein the polypeptide comprises at least 80% sequence identity to SEQ ID NO: 1, 2, 3, or 4 and a heterologous sequence. In some embodiments of the vector the polynucleotide comprises at least 80% sequence identity to SEQ ID NO: 11, 12, 13 or 14 and a heterologous sequence. In some embodiments of the vector, the phosphodiesterase activity is to phosphatidylinositol. In some embodiments of the vector, the polypeptide has phosphodiesterase activity at a temperature range from about 37° C. to about 65° C. In some embodiments the polypeptide has phosphodiesterase activity within a pH range of about pH 4 to pH 9.

In seventh aspect, the present disclosure relates to a vector comprising: a polynucleotide encoding a lipid acyltransferase, wherein the polypeptide comprises at least 80% identity to SEQ ID NO: 7, 8, 9, or 10 and a heterologous sequence. In some embodiments said polynucleotide comprises at least 80% sequence identity to SEQ ID NO: 15 or 16 and a heterologous sequence In some embodiments said lipid acyltransferase acts as enzymatic stabilizer at a temperature range from about 37° C. to 65° C. and within a pH range of about pH 4 to pH 9.

In eighth aspect, the present disclosure relates to a genetically modified microorganism (GMO), preferably *Escherichia coli*. In some embodiments the genetically modified microorganism comprises a vector comprising a polynucleotide encoding a lipid acyltransferase, wherein the polypeptide comprises at least 80% identity to SEQ ID NO: 7, 8, 9, or 10 and a heterologous sequence; wherein lipid acyltransferase stabilizes the activity of a phosphatidylinositol-specific phospholipase and a phosphatidylcholine and phosphatidylethanolamine-specific phospholipase when the phospholipases enzymes react with an oil composition. In some embodiments the genetically modified microorganism comprises a vector comprising a polynucleotide comprising at least 80% sequence identity to SEQ ID NO: 15 or 16 and a heterologous sequence. In some embodiments the genetically modified microorganism comprises encoding a polypeptide having phosphodiesterase activity, and wherein the polypeptide comprises at least 80% sequence identity to SEQ ID NO: 1, 2, 3, or 4 and a heterologous sequence. In some embodiments, the having phosphodiesterase activity is phosphatidylinositol-specific phospholipase C. In some embodiments the genetically modified microorganism comprises a vector comprising, a heterologous sequence, a polypeptide with at least 85% identity to SEQ ID NO: 5, wherein the polypeptide has phospholipase C activity. In some embodiments the genetically modified microorganism comprises a vector comprising a polynucleotide comprising at least 80% sequence identity to SEQ ID NO: 11 and a heterologous sequence. In some embodiments the genetically modified microorganism comprises, one or more vectors of the present disclosure. In some embodiments the genetically modified microorganism comprises, any combination of the vectors of the present disclosure.

In ninth aspect, the present disclosure relates to an isolated polypeptide from a culture media comprising the genetically modified organism (GMO) of the invention. In some embodiment the isolated polypeptide from a culture media comprises a genetically modified organism (GMO), wherein the GMO comprises a vector comprising a polynucleotide with lipid acyltransferase activity and has at least 80% identity to SEQ ID NO: 7, 8, 9, or 10, and a heterologous sequence. In some embodiment the isolated polypeptide from a culture media comprises a genetically modified organism (GMO), wherein the GMO comprises a vector comprising a polypeptide with phospholipase C activity and has at least 85% identity to SEQ ID NO: 5, and a heterologous sequence. In some embodiment the isolated polypeptide(s) from a culture media comprises one or more GMOs of the present disclosure. In some embodiments the isolated polypeptide from a culture media is a polypeptide comprising phosphodiesterase activity and has at least 80% sequence identity to SEQ ID NO: 1, 2, 3, or 4. In some embodiments the isolated polypeptide from a culture media is a lipid acyltransferase and has at least 80% identity to SEQ ID NO: 6, 7, 8, 9, or 10. In some embodiments the isolated polypeptide from a culture media is a polypeptide comprising phosphodiesterase activity and has at least 85% identity to SEQ ID NO: 5. In some embodiments the phosphodiesterase activity is phosphatidylinositol-specific phospholipase C.

In tenth aspect, the present disclosure relates to an enzymatic mixture composition for refining an oil composition comprising: a phosphatidylinositol-specific phospholipase, preferably with at least 80% identity to SEQ ID NO: 1, 2, 3, or 4; a phosphatidylcholine and phosphatidylethanolamine-specific phospholipase, preferably with at least 85% identity to SEQ ID NO: 5; and a lipid acyltransferase enzyme, preferably with at least 80% identity to SEQ ID NO: 6, 7, 8, 9, or 10. In some embodiments of the enzymatic mixture, the lipid acyltransferase is a phosphatidylcholine-sterol O-acyltransferase. In some embodiments of the enzymatic mixture, does not increase the free fatty acid content in the oil composition after degumming. In some embodiments of the enzymatic mixture, does not increase the lysophospholipid content in the oil composition after degumming. In some embodiments, the lipid acyltransferase with at least 80% identity to SEQ ID NO: 6, 7, 8, 9, or 10, more preferably with at least 80% identity to SEQ ID NO: 10 is an enzymatic stabilizer that stabilizes the activity of a phosphatidylinositol-specific phospholipase and a phosphatidylcholine and phosphatidylethanolamine-specific phospholipase when reacting with an oil composition. In some embodiments, the phosphatidylinositol-specific phospholipase has at least 80% identity to SEQ ID NO: 1, 2, 3, or 4. In some embodiments, the phosphatidylcholine and phosphatidylethanolamine-specific phospholipase has at least 85% identity to SEQ ID NO: 5. In some embodiments, the enzymatic mixture does not comprise a phospholipase A. In some embodiments, the concentration of the lipid acyltransferase enzyme is is between 1/10 and 1/100 of the recommended concentration for oil degumming (that is between 0.1 to 1 TIPU/g oil). In some embodiments, the concentration of the lipid acyltransferase is not greater than 0.01 TIPU/g oil. In some embodiments, the concentration of the lipid acyltransferase is not greater than 0.001 TIPU/g oil. In some embodiments, the concentration of the lipid acyltransferase is not greater than 0.06 TIPU/g oil. In some embodiments, the concentration of the lipid acyltransferase is about 0.01 TIPU/g oil. In some embodiments, the concentration of the lipid acyltransferase is about 0.001 TIPU/g oil. In some embodiments, the concentration of the lipid acyltransferase is about 0.05 TIPU/g oil.

In eleventh aspect, the present disclosure relates to an oil mixture comprising: a crude oil, a phosphatidylinositol-specific phospholipase C, and a lipid acyltransferase. In some embodiments, the phosphatidylinositol-specific phospholipase C has at least 80% identity to SEQ ID NO: 1, 2, 3, or 4. In some embodiments, the lipid acyltransferase has at least 80% identity to SEQ ID NO: 6, 7, 8, 9, or 10. In some embodiments, the lipid acyltransferase is a phosphatidylcholine-sterol O-acyltransferase. In some embodiments, the lipid acyltransferase is an enzymatic stabilizer that stabilizes the activity of a phosphatidylinositol-specific phospholipase and a phosphatidylcholine and phosphatidylethanolamine-specific phospholipase when reacting with an oil composition. In some embodiments, the relationship between the concentration of phosphatidylinositol-specific phospholipase C, and a lipid acyltransferase is 50:1 for oil degumming.

In twelfth aspect, the present disclosure relates to a method for degumming an edible oil comprising: (a) providing a phosphatidylinositol-specific phospholipase with at least 80% identity to SEQ ID NO: 1, 2, 3, or 4; (b) providing a phosphatidylcholine and phosphatidylethanolamine-specific phospholipase C with at least 80% identity to SEQ ID NO: 5; (c) providing a lipid acyltransferase with at least 80% identity to SEQ ID NO: 6, 7, 8, 9, or 10; and mixing the edible oil with the enzymes of steps (a), (b), and (c), thereby degumming the edible oil. In some embodiments, the method does not comprise a phospholipase A. In some embodiments of the method, the lipid acyltransferase is a phosphatidylcholine-sterol O-acyltransferase. In some embodiments of the method, the edible oil is a soybean, a rapeseed, a sunflower seed, a rice bran, a sesame, a corn, a palm, a sesame, or a peanut oil, or a combination thereof. In some aspects, the present disclosure provides a method for degumming an edible oil comprising: providing a phosphatidylinositol-specific phospholipase with at least 80% identity to SEQ ID NO: 1, 2, 3, or 4; providing a phosphatidylcholine and phosphatidylethanolamine-specific phospholipase C with at least 80% identity to SEQ ID NO: 5; providing a lipid acyltransferase with at least 80% identity to SEQ ID NO: 6, 7, 8, 9, or 10; and mixing the edible oil with the enzymes of steps (a), (b), and (c), thereby degumming the edible soybean oil, (i) wherein the method hydrolyze greater than 80% (w/w) of phospholipids in the edible oil into diacylglycerol and phosphate ester; (ii) wherein the method increases the oil yield by at least 2.0% compared to a non-enzymatic degumming method; (iii) wherein a free fatty acid content does not increase; (iv) wherein the method reduces greater than 70% of the mass of the gums in the oil composition; (v) wherein the activity of the phosphatidylinositol-specific phospholipase, and the phosphatidylcholine and phosphatidylethanolamine-specific phospholipase is maintained at a 80-90% activity level; (vi) wherein phosphatidylinositol-specific phospholipase or the phosphatidylcholine and phosphatidylethanolamine-specific phospholipase is higher compared to an enzymatic oil degumming method without a lipid acyltransferase; and (vii) wherein the total enzymatic activity comprising phosphatidylinositol-specific phospholipase activity and the phosphatidylcholine and phosphatidylethanolamine-specific phospholipase activity is at least 10% higher compared to an enzymatic oil degumming method without a lipid acyltransferase as an enzymatic stabilizer. In some embodiments, the method does not comprise a phospholipase A. In some embodiments of the method, the concentration of the lipid acyltransferase is not greater than 0.01 TIPU/g oil. In some embodiments of the method, the concentration of the lipid acyltransferase is not greater than 0.001 TIPU/g oil. In some embodiments of the method, the concentration of the lipid acyltransferase is not greater than 0.06 TIPU/g oil. In some embodiments of the method, the concentration of the lipid acyltransferase is about 0.01 TIPU/g oil. In some embodiments of the method, the concentration of the lipid acyltransferase is about 0.008 TIPU/g oil. In some embodiments of the method, the concentration of the lipid acyltransferase is about 0.001 TIPU/g oil. In some embodiments of the method, the edible oil is a soybean, a rapeseed, a sunflower seed, a rice bran, a sesame, a corn, a palm, a sesame, or a peanut oil, or a combination thereof.

In thirteenth aspect, the present disclosure relates to a fermentation process to obtain a recombinant phosphatidylinositol-specific phospholipase of *L. sphaericus* with at least 80% identity to SEQ ID NO: 1, that comprises the following steps:

(1) culture of genetically modified microorganism comprising a polynucleotide with at least 80% sequence identity to SEQ ID NO: 11 under conditions to obtain said phospholipase in a titer at least 13 g M.

(2) separate said phospholipase from supernatant.

In some embodiments of the the fermentation process, step (1) comprise a culture medium of semidefined HM at a pH 7, agitation and a temperature of 37° C. and the expression of the PI-PLC gene is induced at OD600 of 100 with L-arabinose and glycerol as carbon source.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

1. DETAILED DESCRIPTION OF THE INVENTION

I. General Overview

Figure 1:
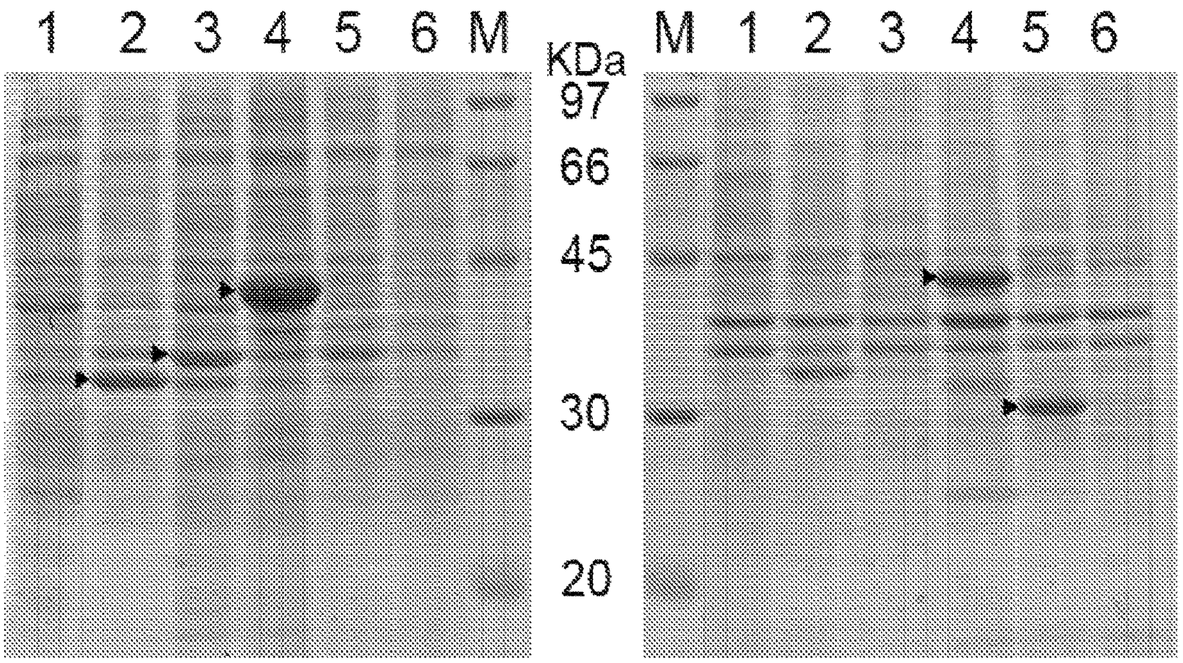
FIG. 1: shows PIPLC expression analysis. SDS-PAGE analysis of *E. coli* strains supernatants (left) and pellets (right) carrying plasmids pKCN231 (PI-PLC *B. cereus*, lane 2), pKCN232 (PI-PLC *A. flavus*, lane 3), pKCN233 (PI-PLC *L. sphaericus*, lane 4), pKCN234 (PI-PLC *S. antibioticus*, lane 5) and pKCN235 (PI-PLC *E. faecalis*, lane 6). Lane 1 corresponds to *E. coli* strain carrying the empty vector. Red arrows indicate the corresponding PI-PLC protein.

The present disclosure relates compositions and methods, for oil degumming. In various aspects the compositions and methods, described herein relate to generating an oil to be used in a consumer product. In one aspect the compositions and methods are used to make an edible oil for a consumer product. In another aspect the compositions and methods provided herein are used to make a biofuel for a consumer product.

The disclosure also provides various compositions related to oil degumming methods. In some aspects the disclosure provides for polypeptides, and functional homologs thereof. In some aspects the disclosure provides for vectors and cassettes which can be propagated in a microorganism. In some aspects the disclosure provides for various genetically modified organisms. In some aspects the disclosure provides a culture media comprising one or more genetically modified organism compositions or combination thereof. In some aspects the disclosure provides for isolated polypeptides or from a culture media comprising the genetically modified organisms of the present disclosure. In some aspects the disclosure provides for numerous enzymatic mixtures for oil degumming. In some aspects the disclosure provides for a crude oil mixture comprising the enzymatic mixtures or enzyme compositions described herein. In some aspects the disclosure provides for degummed or refined edible oil with detectable amounts of a polypeptide of the present disclosure. In some aspects the disclosure provides for a degummed or refined biofuel with detectable amounts of a polypeptide of the present disclosure.

The disclosure also provides various methods related to oil degumming. In some aspects the present disclosure provides oil degumming methods that have improved enzymatic activity. In some aspects the present disclosure provides oil degumming methods that have improved hydrolysis of phospholipids. In some aspects the present disclosure provides oil degumming methods that use a smaller amount of enzyme in an oil degumming method. In some aspects the present disclosure provides oil degumming methods that use a smaller amount of a lipid acyltransferase. In some aspects the present disclosure provides methods for refining an edible oil for a consumer product or biofuel. In some aspects the present disclosure provides a two enzyme method for refining an edible oil for a consumer product or biofuel. In some aspects the present disclosure provides a three enzyme method for refining an edible oil for a consumer product or biofuel. In some aspects, the three enzyme method for refining an edible oil or biofuel for a consumer product uses a smaller amount of a lipid acyltransferase. Lastly, the present disclosure provides an improved oil degumming method for an edible oil such as a soybean oil. In some aspects, the improved oil degumming method for an edible oil uses a smaller amount or concentration of a lipid acyltransferase.

II. DEFINITIONS

To facilitate an understanding of the present disclosure, a number of terms and phrases are defined below.

As used herein, unless otherwise indicated, the article “a” means one or more unless explicitly otherwise provided for.

As used herein, unless otherwise indicated, terms such as “contain,” “containing,” “include,” “including,” “having”, “has”, or “with” and the like mean “comprising.”

As used herein, unless otherwise indicated, the term “or” can be conjunctive or disjunctive.

As used herein, unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The term “functional homolog” refers to polynucleotides or polypeptides of the invention modified at one or more base pairs, codons, introns, exons, or amino acid residues (respectively) yet still retain the biological activity of a phospholipase of the invention. Variants can be produced by any number of means included methods such as, for example, error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, GSSM™ and any combination thereof. Techniques for producing variant phospholipases having activity at a pH or temperature, for example, that is different from a wild-type phospholipase, are included herein.

The term “transfection” as used herein refers to the introduction of foreign nucleic acid into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term “stable transfection” or “stably transfected” refers to the introduction and integration of foreign nucleic acid, DNA or RNA, into the genome of the transfected cell. The term “stable transfectant” refers to a cell which has stably integrated foreign DNA into the genomic DNA.

As used herein, the terms “nucleic acid molecule encoding,” “DNA sequence encoding,” and “DNA encoding” refer to the order or sequence of deoxyribonucleotides along a strand of deoxyribonucleic acid. The order of these deoxyribonucleotides determines the order of amino acids along the polypeptide (protein) chain. The nucleic acid sequence thus codes for the amino acid sequence.

The term “heterologous sequence”, as used herein, refers to a polypeptide or nucleotide sequence that is ligated to, or is manipulated to become ligated to, a nucleic acid sequence to which it is not ligated in nature, or to which it is ligated at a different location in nature. Heterologous nucleic acid may include a nucleotide base pair or amino acid residue or sequence that is not naturally found in the cell into which it is introduced or the heterologous nucleic acid may contain some modification relative to the naturally occurring sequence.

The term “about” is understood as within a range of normal tolerance in the art, unless specifically stated or obvious from context. For example “about” can be understood as within 2 standard deviations of the mean, “about” can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term “about”.

The term “crude oil” is can include whole crude oil from conventional sources, including crude oil that has undergone some pre-treatment. The term crude oil can also be understood to include oil that has been subjected to water-oil separations; or other processing steps know or will be known in the art of oil refinement.

The term enzymatic stabilizer is understood as a compound that maintains 80-90% activity level of PLC enzymes at least for a year of storage in aqueous solution and also maintains PLC activity in oil over 80% of its initial activity for at least 6 hours. Said enzymatic stabilizer is a macromolecule, just like a protein, a polysaccharide or glycolipid, more precisely a protein that can interact with lipids. Preferably, for this invention said enzymatic stabilizer is a lipid acyltransferase from *Aeromonas enteropelogenes*. The enzymatic stabilizer stabilize other enzymes, and produces an increase of the half life time of the other components of the enzymatic mixture, particularly the lipid acyltransferse increase the half life time of the polypeptides that has phosphatidylinositol-specific phospholipase activity, a phosphatidylcholine and phosphatidylethanolamine-specific phospholipase activity.

The term oil composition can include edible oil, crude oil, wet gums and gums between others.

III. METHODS

The present disclosure provides enhanced methods and methods for degumming an oil composition. In some aspects, the present disclosure provides a two enzyme method. In some aspects the method does not comprise a phospholipase A. In some aspects, the free fatty acid content does not increase after the oil degumming method. In some aspects, the lysophospholipids content does not significantly increase during the oil degumming.

In another aspect the present disclosure provides a three enzyme method for oil refinement.

In some aspects the three enzyme method for oil refinement can comprise a phosphatidylinositol-specific phospholipase, a phosphatidylcholine and phosphatidylethanolamine-specific phospholipase, and a lipid acyltransferase. In some aspects the method for degumming an oil composition does not comprise a phospholipase A. In some aspects, the free fatty acid content in the oil composition does not increase more than 1%, 2%, 3%, 4%, 5%. In some aspects, the free fatty acid content in the oil composition does not increase. In some aspects, the lipid acyltransferase is a phosphatidylcholine-sterol O-acyltransferase.

In some aspects, the present disclosure provides a method for enhanced oil degumming comprising: contacting an oil composition with an enzymatic mixture, wherein the enzymatic mixture comprises a phosphatidylinositol-specific phospholipase activity, a phosphatidylcholine and phosphatidylethanolamine-specific phospholipase activity, and a lipid acyltransferase. In some aspects the method for degumming an oil composition does not comprise a phospholipase A activity. In some aspects, the free fatty acid content in the oil composition does not increase more than 1%, 2%, 3%, 4%, 5%. In some aspects, the free fatty acid content in the oil composition does not increase. In some aspects, the lipid acyltransferase is a phosphatidylcholine-sterol O-acyltransferase.

In certain aspects, the enzyme mixture can hydrolyze greater than 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% (w/w) of phospholipids present in the oil into a diacylglycerol and a phosphate ester.

In some aspects, the method results in increasing the oil yield by at least 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0% compared to an non-enzymatic degumming method.

In some aspects, the method results in increasing the oil yield by at least 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0% compared to an enzymatic degumming method.

In certain aspects, the method can reduce greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 0.41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the mass of the gums in the oil.

In some aspects, the phosphatidylinositol-specific phospholipase activity, and the phosphatidylcholine and phosphatidylethanolamine-specific phospholipase activity is maintained at 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% activity level during the method. In some embodiments of the method the phosphatidylinositol-specific phospholipase activity or the phosphatidylcholine and phosphatidylethanolamine-specific phospholipase activity is higher compared to an enzymatic oil degumming method without a lipid acyltransferase.

In some aspects, total enzymatic activity from the phosphatidylinositol-specific phospholipase and the phosphatidylcholine and phosphatidylethanolamine-specific phospholipase is at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50%, higher compared to an enzymatic degumming method without lipid acyltransferase.

Recommended LAT Concentration for Degumming an Oil

The recommended concentration of lipid acyltransferase for the method of crude oil degumming of the present invention is not greater than about 0.01 TIPU/g oil. In some applications the recommended concentration of the lipid acyltransferase is not greater than about 0.1 TIPU/g oil. In some applications the recommended concentration of the lipid acyltransferase is not greater than about 0.06 TIPU/g oil. In some applications the recommended concentration of the lipid acyltransferase is about 0.01 TIPU/g oil. In some applications the recommended concentration of the lipid acyltransferase is about 0.05 TIPU/g oil. In some applications the recommended concentration of the lipid acyltransferase is about 0.002 TIPU/g oil. In some applications, the recommended LAT concentration is about 10%, 20%, 30%, 40%, 50%, or 60% less than 0.01, TIPU/g, 0.05 TIPU/g oil, or 0.06 TIPU/g oil in applications where the oil is a partially crude oil, a partially refined oil, or a substantially refined oil. In some applications, the recommended LAT concentration is about 10%, 20%, 30%, 40%, 50%, or 60% more than 0.01, TIPU/g, 0.06 TIPU/g oil, or 0.001 TIPU/g oil for an oil mixture comprising two or more oil types.

The recommended concentration of lipid acyltransferase for degumming a crude oil with the method of the present invention is about 0.2 mg/kg of oil, depending on the oil type that is being processed and the LAT preparation.

By way of example only, the recommended LAT concentration for degumming a soybean oil type can be about 0.2 mg/kg of oil In some applications, the recommended LAT concentration can be about 10%, 20%, 30%, 40%, 50%, or 60% less in applications where the oil is a partially crude oil, a partially refined oil, or a substantially refined oil. In some applications, the recommended LAT concentration can be about 10%, 20%, 30%, 40%, 50%, or 60% more for a complex oil mixture comprising two or more oil types.

In some aspects, the lipid acyltransferase enzyme is used in present invention at one tenth or one hundredth of the recommended concentration for an enzymatic oil degumming method. In some aspects, the concentration of the lipid acyltransferase is not greater than 0.01 TIPU/g oil. In some aspects, the concentration of the lipid acyltransferase is not greater than 0.06 TIPU/g oil. In some aspects, the concentration of the lipid acyltransferase is not greater than 0.005 TIPU/g oil. In some aspects, the concentration of the lipid acyltransferase is about 0.01 TIPU/g oil. In some aspects, the concentration of the lipid acyltransferase is about 0.06 TIPU/g oil. In some aspects, the concentration of the lipid acyltransferase is about 0.002 TIPU/g oil.

In some aspects, the enzyme lipid acyltransferase of the invention has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10. In some aspects, the enzyme that imparts phosphatidylinositol-specific phospholipase activity has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4.

In some aspects, the enzyme that imparts phosphatidylcholine and phosphoethanolamine-specific phospholipase activity has at least 80%, 81%, 82%, 83%, 84%, or 85%, identity to SEQ ID NO: 5.

In some embodiments of the method, the oil is an edible oil. In some embodiments of the method, the edible oil is a soybean, a rapeseed, a sunflower seed, a rice bran, a sesame, a corn, a palm, a sesame, or a peanut oil, or a combination thereof.

In some aspects, the method can comprise hydrolyzing at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the phospholipids of the original concentration in the crude oil. In some aspects the method for degumming an oil composition does not comprise a phospholipase A.

In some aspects, the method can comprise hydrolyzing at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of phosphatidylcholine, phosphatidylethanolamine, phosphatidylinositol, or phosphatidic acid, or a combination thereof in the crude oil.

In some aspects, the method comprises increasing the oil yield by at least 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, or 6.0% compared to non-enzymatic oil degumming method.

The present disclosure provides a method for degumming an oil composition comprising: treating the oil composition with a polypeptide having phosphodiesterase activity and at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4.

The present disclosure provides a method for degumming an oil composition comprising: treating the oil composition with a polypeptide having lipid acyltransferase activity and at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10. In some aspects, the method for degumming an oil composition does not comprise a phospholipase A.

In some aspects the method for degumming an oil composition further comprises, wherein said method inhibits at most 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the phosphodiesterase, phospholipase C, phosphatidylinositol-specific phospholipase, or the phosphatidylcholine and phosphatidylethanolamine-specific phospholipase activity. In some aspects the method for degumming an oil composition does not comprise a phospholipase A.

In some aspects the method for degumming an oil composition further comprises, wherein the phosphodiesterase, phospholipase C, phosphatidylinositol-specific phospholipase, or the phosphatidylcholine and phosphatidylethanolamine-specific phospholipase enzyme maintains 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of its enzymatic activity during the degumming method.

In some aspects the method, the lipid acyltransferase activity does not increase the fatty acid content in the oil greater than a 1%, 2%, 3%, 4%, 5%, increase compared to the original fatty acid content in the crude oil composition.

In some aspects, the method can increase oil yield by at least 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 0.4%, 4.8%, 4.9%, 5.0%, 5.1%, 5.2%, 5.3%, 5.4%, 5.5%, 5.6%, 5.7%, 5.8%, 5.9%, 6.0% compared to an enzymatic oil refinement method with a phospholipase A.

In some aspects the method for degumming an oil composition obtains biofuel. In some aspects the method for degumming an oil composition obtain biofuel that is biodiesel. In some aspects the method for degumming an oil composition obtain an edible oil. In some aspects the edible oil is a soybean, a rapeseed, a sunflower seed, a rice bran, a sesame, a corn, a palm, a sesame, or a peanut oil.

The present disclosure provides a method for increasing the efficiency of enzymatic oil refinement comprising: providing an oil composition comprising phospholipids; reacting the oil phospholipids with at least two phosphodiesterase and a lipid acyltransferase, thereby generating a phosphate ester and a diacylglyerol.

Increasing Enzymatic Efficiency

The present disclosure provides a method for increasing the efficiency of enzymatic oil refinement comprising: providing an oil composition comprising phospholipids; reacting the oil phospholipids with at least two phosphodiesterase and a lipid acyltransferase and does not comprise a phospholipase A, thereby generating a phosphate ester and a diacylglyerol.

In some aspects the method for increasing the efficiency of enzymatic oil refinement comprises at least two phosphodiesterase, wherein at least one of the phosphodiesterases has higher activity compared to an oil refinement method without a lipid acyltransferase.

In some aspects the method for increasing the efficiency of enzymatic oil refinement comprises a polypeptide with phosphodiesterase activity and has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4. In some aspects the method for degumming an oil composition does not comprise a phospholipase A.

In some aspects the method for increasing the efficiency of enzymatic oil refinement comprises wherein a second polypeptide has phosphodiesterase activity and at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5.

In some aspects the method for degumming an oil composition does not comprise a phospholipase A.

In some aspects the method for increasing the efficiency of enzymatic oil refinement comprises the isolated polypeptides from a vector comprising a polynucleotide encoding a polypeptide having phosphodiesterase activity and at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4, and a heterologous nucleic acid sequence. In some aspects the method for degumming an oil composition does not comprise a phospholipase A.

In some aspects the method for increasing the efficiency of enzymatic oil refinement comprises the isolated polypeptides from a vector comprising: a polynucleotide encoding a polypeptide having lipid acyltransferase activity and at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7, 8, 9, or 10 and a heterologous sequence. In some aspects the method for degumming an oil composition does not comprise a phospholipase A.

In some aspects the method for increasing the efficiency of enzymatic oil refinement comprises a lipid acyltransferase with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10. In some aspects the method for degumming an oil composition does not comprise a phospholipase A.

In some aspects, the method for increasing the efficiency of enzymatic oil refinement comprises the isolated polypeptides from a vector comprising polynucleotide sequence encoding two or more of the following proteins: phosphatidylinositol-specific phospholipase C and lipid acyltransferase, phosphatidylcholine and phosphatidylethanolamine-specific phospholipase C and lipid acyltransferase, and phosphatidylinositol-specific phospholipase C and phosphatidylcholine and phosphatidylethanolamine specific phospholipase C. In some aspects the isolated polypeptide is obtained from a media comprising the vector.

Degumming of an Edible Oil

The present disclosure provides a method for degumming an edible oil comprising the steps of: (a) providing a phosphatidylinositol-specific phospholipase with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4; (b) providing a phosphatidylcholine and phosphatidylethanolamine-specific phospholipase C with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5; (c) providing a the lipid acyltransferase, wherein the lipid acyltransferase has least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10; mixing the crude soybean oil with the enzymes of steps (a), (b), and (c), thereby degumming the crude soybean oil. In some aspects, method for degumming a crude soybean oil does not comprise a phospholipase A.

In another aspect the present disclosure provide a method for degumming an edible oil comprising: providing a phosphatidylinositol-specific phospholipase with at least 80% identity to SEQ ID NO: 1, 2, 3, or 4; providing a phosphatidylcholine and phosphatidylethanolamine-specific phospholipase C with at least 80% identity to SEQ ID NO: 5; providing a lipid acyltransferase with at least 80% identity to SEQ ID NO: 6, 7, 8, 9, or 10; and mixing the edible oil with the enzymes of steps (a), (b), and (c), thereby degumming the edible soybean oil. In some embodiments of the method, the lipid acyltransferase is a phosphatidylcholine-sterol O-acyltransferase (i) wherein the method hydrolyze greater than 80% (w/w) of phospholipids in the edible oil into diacylglycerol and phosphate ester; (ii) wherein the method increases the oil yield by at least 2.0% compared to a non-enzymatic degumming method; (iii) wherein a free fatty acid content does not increase; (iv) wherein the activity of the phosphatidylinositol-specific phospholipase, and the phosphatidylcholine and phosphatidylethanolamine-specific phospholipase is maintained at a 80-90% activity level; (v) wherein phosphatidylinositol-specific phospholipase or the phosphatidylcholine and phosphatidylethanolamine-specific phospholipase is higher compared to an enzymatic oil degumming method without a lipid acyltransferase; and (vi) wherein the total enzymatic activity comprising phosphatidylinositol-specific phospholipase activity and the phosphatidylcholine and phosphatidylethanolamine-specific phospholipase activity is at least 10% higher compared to an enzymatic oil degumming method without a lipid acyltransferase activity. In some embodiments of the method, the concentration of the lipid acyltransferase as enzymatic stabilizer is not greater than 0.01 TIPU/g oil. In some embodiments of the method, the concentration of the lipid acyltransferase is not greater than 0.05 TIPU/g oil. In some embodiments of the method, the concentration of the lipid acyltransferase is not greater than 0.002 TIPU/g oil. In some embodiments of the method, the concentration of the lipid acyltransferase is about 0.01 TIPU/g oil. In some embodiments of the method, the concentration of the lipid acyltransferase is about 0.002 TIPU/g oil. In some embodiments of the method, the concentration of the lipid acyltransferase is about 0.05 TIPU/g oil.

IV. COMPOSITIONS

Oils for a Consumer Product

The present disclosure provides an edible oil for a consumer product made by the methods and methods provided herein. In some aspects the edible oil for a consumer product can comprises a soybean oil, a rapeseed oil, a sunflower seed oil, a rice bran oil, a sesame oil, a corn oil, a palm oil, a peanut oil, an acai oil, an almond oil, a babassu oil, a blackcurrent seed oil, a borage seed oil, a canola oil, a cashew oil, a castor oil, a coconut oil, a coriander oil, a cottonseed oil, a *crambe* oil, a flax seed oil, a grape seed oil, a hazelnut oil, other nut oils, a hempseed oil, a jatropha oil, a jojoba oil, a linseed oil, a macadamia nut oil, a mango kernel oil, a meadowfoam oil, a mustard oil, a neat's foot oil, an olive oil, a palm oil, a palm kernel oil, a palm olein oil, a pecan oil, a pine nut oil, a pistachio oil, a poppy a seed oil, a rapeseed oil, a rice bran oil, a safflower oil, a sasanqua oil, a shea butter oil, a tall oil, a tsubaki oil, a walnut oil, or any combination thereof.

The present disclosure provides a biofuel made by the methods and methods provided herein. In some aspects the biofuel can comprises a fish oil, an animal oil, a plant oil, an algae oil, a vegetable oil, a straight vegetable oil, a virgin vegetable oil, a waste vegetable oil, an animal fat, a grease, a tallow, a lard, or a yellow grease or any composition comprising a lipid or an alkyl ester.

B. Expression Vectors and Cassettes

The present disclosure provides for an expression vector or expression cassette comprising at least one nucleic acid of SEQ ID NO: 1, 2, 3, 4, 5, 6, 7, 8, 9, or 10, or a fragment, a variant, or a derivative thereof. In the expression vector or expression cassette, the nucleotide sequence as provided herein can be operably linked to regulatory sequences such that the regulatory sequences are capable of providing the expression of the nucleotide sequence by a host cell or organism.

A vector or cassette of the present disclosure can comprise a molecular backbone with a regulatory sequence, a promoter, a gene, a selectable marker gene, a heterologous regulatory sequence, a heterologous promoter, a heterologous gene, or a combination thereof.

The vector or cassette can be used for the production of RNA or protein molecule in a host cell. The vector or cassette can be transfected or transformed into a host cell.

In some aspects, the vector or cassette is expressed in vitro. In some aspects, the vector or cassette is expressed in vivo. The vector or cassette can be transiently transformed into a host cell or organism. The vector or cassette can be incorporated into the genome of a host cell or organism using any method known in the art. The term "incorporated" preferably covers stable incorporation into a genome of a cell or organism.

In some aspects, the present disclosure provides for a vector or cassette to be expressed in a host cell. The present disclosure provides for a vector or cassette to be expressed a host cell and culturing the host cell in a media. The present disclosure provides for a vector or cassette to be expressed a host cell and culturing the host cell in a media, thereby allowing the host cell to grow and replicate, followed by the isolation of the expressed recombinant polypeptide from the media.

There are many commercially available expression vectors. Examples of such as expression vectors that can be use with the present disclosure include, but are not limited to, pBR322 (ATCC 37017), pKK223-3 (Pharmacia Fine Chemicals, Uppsala, Sweden), GEM1 (Promega Biotec, Madison, Wis., USA) pQE70, pQE60, pQE-9 (Qiagen), pD10, psiX174 pBluescript II KS, pNH8A, pNH16a, pNH18A, pNH46A (Stratagene), ptrc99a, pKK223-3, pK 233-3, pDR540, pRIT5 (Pharmacia), pK 232-8 and pCM7. Particular eukaryotic vectors include pSV2CAT, pOG44, pXT1, pSG (Stratagene) pSVK3, pBPV, pMSG, pSVL (Pharmacia). These and other expression vectors known in the art may be used with the present disclosure.

Regulatory Sequences

A vector or cassette can comprises one or more regulatory sequences for controlling expression of the sequences provided by the present disclosure.

A regulatory sequence can be any segment of a nucleic acid molecule which is capable of increasing or decreasing the expression of specific genes within a host cell or an organism. The regulatory sequences for controlling expression can be from the host cell or organism. The regulatory sequences for controlling expression can be heterologous. The regulatory sequences can be chimeric, comprising sequence elements from two or more different regulatory sequences. Examples of uses of 3' UTR regulatory sequences with the sequences of the present disclosure are as follows: a vector can comprise enhancers or repressors of gene expression. A vector can comprises 3' UTR sequences to control expression or stability of a RNA molecule. The 3' UTR sequences can be from the same host cell. The 3' UTR sequences can be heterologous. The 3' UTR sequences can be chimeric comprising sequence elements from two or more different 3' UTR sequences.

As another example, a vector can comprise secretion leader sequence. The leader sequence can be from the same host cell or organism. The secretion leader sequence can be heterologous. Suitable leader sequences can include, but are not limited to, fungal amyloglucosidase (AG) gene (glaA—both 18 and 24 amino acid versions e.g. from *Aspergillus*), the α-factor gene (yeasts e.g. *Saccharomyces, Kluyveromyces* and *Hansenula*) or the α-amylase gene (*Bacillus*). In some aspects, a chimeric secretion leader sequence can be used with the present disclosure. The particular secretion leader sequence used is generally selected based on the host cell to be used for expression of the gene or protein.

Promoters

A promoter can be a region of DNA that initiates transcription of a particular gene, cell type, or host cell. Promoters are generally located near the transcription start sites of genes. A vector or cassette can comprise one or more promoters. A vector or cassette can comprise one or more promoters and can further comprise one or more regulatory sequences as provided herein.

Promoters used with the present disclosure can be a constitutive promoter. The promoter can be an inducible promoter. The promoter can be a host-cell specific promoter. The promoter can be a tissue-specific promoter. The promoter can be from the same host cell or organism as it is expressed in. The promoter can be a heterologous. The promoter can be a chimeric, comprising sequence elements from two or more different promoters described above.

Depending on the application a prokaryotic promoters or eukaryotic promoters may be used. Examples of suitable prokaryotic promoters they can be used include but are not limited to, the *E. coli* lac or trp promoters, the lacI promoter, the lacZ promoter, the T3 promoter, the T7 promoter, the gpt promoter, the lambda PR promoter, the lambda PL promoter, promoters from operons encoding glycolytic enzymes such as 3-phosphoglycerate kinase (PGK), or the acid phosphatase promoter.

Examples of suitable eukaryotic promoters include but are not limited to, the CMV immediate early promoter, the HSV thymidine kinase promoter, heat shock promoters, the early and late SV40 promoter, LTRs from retroviruses, or the mouse metallothionein-I promoter.

Promoters suitable for use with the present disclosure can be about 40-60 base pairs long, about 80-100 base pairs long, about 100-300 base pairs long, 300-1000 base pairs long.

In addition, depending on the application or host cell type, a particular promoter type will be used. Promoters used with the present disclosure can comprise TATA box, Pribnow box, SOS box, CAAT box, CCAAT box, operator, origin of replication of plasmids pUC19, pACYC177, pUB110, pE194, pAMB1, pIJ702, an upstream activation sequence, or the like.

The vectors may further comprise one or more selectable marker genes. Example of a selectable marker gene, can be a gene which confers antibiotic resistance (e.g. ampicillin, kanamycin, chloramphenicol or tetracyclin resistance). In some aspects, the selection may be accomplished by co-transformation with a second vector carrying one or more selectable marker genes.

The nucleotide sequences of the present disclosure may be present in an expression vector. Example of expression vector types that can be used with the compositions and methods include but are not limited to: a plasmid, a cosmid, a virus such as a, a DNA virus, a RNA virus, a retrovirus, a phage vector, a phagemid, a fosmid, a bacteriophage such as a bacteriophage P1-derived vector (PAC), or an artificial chromosome such as a bacterial artificial chromosome (BAC), a yeast artificial chromosome (YAC), or a mammalian artificial chromosome (MAC).

The present disclosure also provides for other forms of expression vectors which serve equivalent functions and which are, or become, known in the art for carrying out expression of a protein in a host cell or organism.

The type of vector chosen for a given application will depend on the amount of protein desired, the type of host cell to be expressed in, the size of the constructed to be used in the vector, or the organism to be used to express the vector.

C. Genetically Modified Organisms

The present disclosure provides for genetically modified organisms (GMOs) comprising a nucleotide sequence encoding a polypeptide SEQ ID NO: 1, 2, 3, 4, 5, 6, 7, 8, 9, 10, as provided herein or their complementary sequences.

A genetically modified organism encompassed by the present disclosure is any microorganism or host cell that comprises a sequence, a vector or a cassette of the present disclosure. In some aspects the genetically modified organism comprises a nucleotide sequence encoding a variant, fragment or a functional homolog of the a polypeptide SEQ ID NO: 1, 2, 3, 4, 5, 6, 7, 8, 9, or 10 as provided herein.

The GMO can be modified to be deficient in one or more genes. The GMO can be genetically modified to include one or more genes. The GMO can be genetically modified to be deficient in one or more genes and to include one or more genes. Various means for transformation of a host cell to make a GMO are well known in the art. The vector may be introduced into the host cells using any of a variety of techniques including but not limited to: transformation, transfection, transduction, viral infection, gene guns, or Ti-mediated gene transfer. Particular methods that can be used with the present disclosure include calcium phosphate transfection, DEAE-Dextran mediated transfection, lipofection, or electroporation See Davis, L., Dibner, M., Battey, I., *Basic Methods in Molecular Biology*, (1986) and Sambrook et al *Molecular Cloning: A Laboratory Manual, 2nd edition*, Cold Spring Harbor Laboratory Press (1989).

In some aspects, the GMO can comprise one type of vector or cassette. In some aspects, the GMO can comprise at least one or more types of vector(s) or cassette(s). In some aspects, the GMO can comprise a cassette and a vector of the present disclosure.

The nucleotide sequence of the present disclosure can be incorporated within the host's genome or stably replicated by the host as an autonomous plasmid or other molecular-structure.

Suitable host cell to make a GMO of the present disclosure can be: a prokaryote, a fungal, a bacterial, a yeast, a plant, an insect, or a mammalian cell. Examples of a yeast cell that can be used with the present disclosure include but are not limited to: *Pichia pastoris, Saccharomyces cerevisiae*, or *Schizosaccharomyces pombe. Examples of bacterial cells that can be used, include but are not limited to, E. coli, Lactococcus lactis, Streptomyces, Bacillus subtilis, Bacillus cereus, Salmonella typhimurium* or any species within the genera *Bacillus*, such as for example, *B. licheniformis, B. alkalophilus, B. amyloliquefaciens, B. circulans, B. clausii, B. coagulans; B. firmus, B. lautus; B. lentus; B. megaterium, B. pumilus* or *B. stearothermophilus*, or any species within the genera *Streptomyces* and *Staphylococcus.*

In some aspects, a preferred prokaryotic host cell can be *E. coli* or *Bacillus subtilis*. Examples of insect cells that can be used include but are not limited to, *Drosophila* S2 and *Spodoptera* Sf9. Examples of mammalian cell can include any mouse or human cell line. A particular host cell will be chosen based its characteristics see or cassette incorporated into the genome of a host microorganism or cell. In some aspects, the media mixture can comprise the vector or cassette can be transiently maintained in a host microorganism or cell. In some aspects, the media mixture comprises one type of host organism. In some aspects, the media comprise at least one or more types of host microorganism(s) or cell(s).

As known to those with skill in the art, a growth or culture media is a liquid or gel designed to support the growth of microorganisms or cells. As those who are in the art will appreciate, there are different types of media for growing different types of cells or organisms. Genetically modified organisms (e.g. host cells comprising a sequence, vector or a cassette of the present disclosure) can be cultured in nutrient media to make a media comprising the polynucleotides or polypeptides of the present disclosure.

In general, there are two major types of growth media: those used for cell culture, which is generally used for growth of specific cell types derived from plants or animals, and microbiological culture, which are generally used for growing bacteria or yeast and other microorganisms.

The most common growth media for microorganisms are nutrient broths and agar plates that can use for example nutrient broths such as LB broth (Casein enzymatic digest, 10 g/L; low-sodium Yeast extract, 5 g/L; Sodium Chloride, 5 g/L; Inert tableting aids, 2 g/L) or SAS media (K2HPO4, 10 g/L; MOPS (3-morpholinopropane sulfonic acid), 40 g/L; Sodium Chloride, 5 WI; Antifoam (Sin 260), 5 drops/I; Soy flour degreased, 20 g/L; Biospringer 106 (100% dw YE). For some microorganisms, more specialized media containing other factors may be required for their growth and culture. By way of example, viruses require a growth media comprising living cells for their growth and reproduction.

TABLE 1

Table 1: (*Gene Expression Systems. Using nature for the art of expression* (Fernandez, J. M. & Hoeffler, J. P., eds), Academic Press, San Diego, 1999.).

| Characteristics | *E. coli* | Yeast | Insect cells | Mammalian cells |
|---|---|---|---|---|
| Cell growth | Rapid (30 min) | Rapid (90 min) | Slow (18-24 hr) | Slow (24 hr) |
| Complexity of growth medium | Minimum | Minimum | Complex | Complex |
| Cost of growth medium | Low | Low | High | High |
| Expression level | High | Low-high | Low-high | Low-moderate |
| Extracellular expression | Secretion to periplasm | Secretion to medium | Secretion to medium | Secretion to medium |
| Posttranslational modifications | | | | |
| Protein folding | Refolding usually required | Refolding may be required | Proper folding | Proper folding |
| N-linked glycosylation | None | High mannose | Simple, no sialic acid | complex |
| O-linked glycosylation | No | Yes | Yes | Yes |
| Phosphorylation | No | Yes | Yes | Yes |
| Acetylation | No | Yes | Yes | Yes |
| Acylation | No | Yes | Yes | Yes |
| Gamma-carboxylation | No | No | No | Yes |

D. Media Mixtures

The present disclosure provides media mixture compositions. In some aspects, the media mixture comprises at least one of the polypeptides as provided herein, wherein the polypeptide is secreted from the host into the culture media. In some aspects, the media mixture can comprise the vector

Nutrient Media

Nutrient media contain all the elements that most bacterium need for growth and cultivation Some examples of nutrient media include but are not limited to, plate count agar, nutrient agar, or trypticase soy agar.

Minimal Media

Minimal media are growth media that contain the minimum nutrients possible for colony growth and are often used to grow "wild type" or genetically unaltered microorganisms. In general a minimal media typically comprises: water, a carbon source for growth, such as for example, a sugar (e.g. glucose or succinate), various salts, which can be tailored for a specific microorganism and other essential growth elements such as for example, magnesium, nitrogen, phosphorus, or sulfur.

Enriched Media

An enriched media usually comprise all the nutrients required to support the growth of a wide variety of organisms. They can be used to culture many different types of organisms. Examples of enriched media include but are not limited to blood agar or chocolate agar.

Selective Media

Selective growth media can be used with the methods and compositions of the present disclosure to ensure the survival or proliferation of cells expressing the polypeptide and poly nucleotides of the invention. Selective growth media typically will comprise cell that have either antibiotic resistance or the ability to synthesize a certain metabolite and as such allows for the growth and selection of a specific microorganisms or recombinant host cell types as provided herein.

For example, if a microorganism is made to be resistant to a certain antibiotic, such as an organism comprising ampicillin or tetracycline, then that antibiotic can be added to the media in order to prevent other cells, which do not possess the resistance gene from growing. Alternatively, selective media can be lacking an amino acid such as proline in conjunction with microorganism that is genetically alter and naturally unable to synthesize the amino acid.

Transport Media

The present disclosure also encompasses the use of transport medias with the methods and compositions of the present disclosure. In general, transport media comprises buffers and salt and lack of carbon, nitrogen, and organic growth factors so as to prevent microbial multiplication. These types of media can serve as a temporary storage of specimens being transported for cultivation at a later time. Examples of transport media include but are not limited to: thioglycolate broth or stuart transport media.

E. Polypeptides and Polynucleotide Sequences

The polypeptide and polynucleotide sequences of the present disclosure will typically comprise heterologous sequences.

In some aspects, a heterologous sequence can encode one or more polypeptides, homologs of polypeptides, variants of the polypeptides, fragments peptides of the polypeptides, or fusions of the polypeptides that have a similar function. In addition, present disclosure provides for the nucleotide sequence that encode for the polypeptide sequences as well as their complementary sequences.

In some aspects, the polypeptide comprises a sequence from SEQ ID NO: 1, such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 1:

(SEQ ID NO: 1)
MAASERDNINLSEWMREIPNSNTLAEISIPGTHDSGTFRLEDPIKSVWAK

TQENDFRYQMDHGVRFFDIRGRVTDDNTIVLHHGPIYLYVTLQQFINEAK

-continued

EFLKSHPSETIIMSLKEEYESMPGAKESFAKTFENMYFGDSIFLKTEGNI

TLGDSRGKIVLLRRYSGSTMTGGFKNFGWKDNATFTSTTNGNVKITVQDK

YNVNYEEKKAAIDSMLKETVLNKDNPNHIHINFTSLSSGGTAWSSPYYYA

SYLNSISAAKVRLDHLKNLDTKAGWIIMDYIGDRWDPKLYEEIIRANFRY

PPTDEPHLFEHIDGEGIDFTNLPHSKWNDQVSSILLKSYTEITIYEHSNF

TGKSVTLTNTTNSAQLFNLTTYNFNDKMSSYTWKLIR,.

In some aspects, the polypeptide comprises a sequence from SEQ ID NO: 2, such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 2:

(SEQ ID NO: 2)
MGVRLSVQDWMSALGDATPVQRLTIPGTHDSGARVGGPWVACQNTPVDAQ

LNSGIRFLDVRCRAIDNVFAIHHGAFYQELMFGDVLNACRAFLRAHPSET

VLMRVKQEYSEVGAEEFRRIFGIYLDDKGYRSLFRLDAGLPTLGQARGRV

VLLADSDGLGGVRYADPQLFDIQDDYMAEAFGKYPKIEAQFRKAVAQPGK

LFVNYVSTAALLPPRSNADRLNPQVKRLLEGSEGSGWTGLGIVPMDFPNE

NGLAETLIRHNLAGQGVRLTA,.

In some aspects, the polypeptide comprises a sequence from SEQ ID NO: 3 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 3:

(SEQ ID NO: 3)
MVKKIFLNFLIGIGLIILNNFVFSVNEVFADSRWMSTIRDDKPLSRVAVP

GTHDSGTFKMSDPIISALVRTQEQDFRQQLEQGIRFFDIRGRATKNNQIV

LHHGPKYLLVTLHQFLQEAENFLRNNPSETIIMSLKEEYPAMEEVTKSFF

SIFKESYFNYYPFYTGNSSNPKIQETRGKIVLFDRTGNSTLPGYNKIYNW

EDNATFQTTTNNTLPLYVQDEYNATYNRKTHAILDLLKTSSESNEGIFLN

YVSLATGGTAWSSPYYFASYLNPLTGGYINEFHVSNPGWVVMDYSGNRWN

PNLTKKVIETNRYLQ,.

In some aspects, the polypeptide comprises a sequence from SEQ ID NO: 4 such as a functional homolog or variants thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 4:

(SEQ ID NO: 4)
MSIYSSANLNAWMGELKDDTLLSSLSIPGTHNSPTCHVAPPSVRCQAVSP

REQLENGVRFFDIRVQPQYPEDADKDELALVHSVFPISLTGSKYFRDLMR

EVNEFLDQNPSETLIISLKREGPGEHTDQQLSRILSDHYARPDSRWYTNP

KIPTLGEVRGKVVLIRRFDILDHLKDIHGGAGWGICASGWADNCSNATCP

SGQLCIQDFYEVLETENIGEKIKYVQEHCFRAAETCYPFGVLPDHEATKA

-continued

HPFYINFLSASNFWKLGTWPEKIAGKLNPAAVDYLCRKHGEKDDCDWSTG

ILVTDWVGLDGDWDLVRCIVGMNARLKLRQDRHEGDN, .

In some aspects, the polypeptide comprises a sequence from SEQ ID NO: 5 such as a functional homolog or variants thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 5 (also see PCT/US2014/043294, which is hereby incorporated by reference in its entirety):

(SEQ ID NO: 5)

WSAEDKHKEGVNSHLWIVNRAIDIMSRNTTLVKQDRVALLNEWRTELENG

IYAADYENPYYDNST [W or Y]

ASHFYDPDNGKTYIPYAKQAKETGAKYFKLAGESYKNKDMKQAFFYLGLS

LHYLGDVNQPMHAANFTNLSYPQGFHSKYENFVDTIKDNYKVTDGNGYWN

WKGTNPEDWIHGAAVVAKQDYAGIVNDNTKDWFVRAAVSQEYADKWRAEV

TPMTGKRLMDAQRVTAGYIQLWFDTYGNR, .

In some aspects, the polypeptide comprises a sequence from SEQ ID NO: 6 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 6:

(SEQ ID NO: 6)

MAKFMDKTHPISELYVFGDSLSDTGMVFRATGGMYPPNPTYFQGRYSNGR

VWIEYLAESLHLSPKQTHNFAYGGATTANVGNSYVPSLLNQVQSFTQTHQ

QTNPDALYVLWAGANDYLQGVSSASIPVKNVTTAINSLTDVGAKKILVGN

LPDLGQLPATRNSTNSVSLSALTQAHNQGLRRSLKVLGQQHSDLEIVQLD

ANALYRHAIAKPAAFNFTNVISPCLSGDRTCSNPDQFLFWDGIHPTAAAH

RIIAETAFSTIQEAGMTNPLLSLSLEYN, .

In some aspects, the polypeptide comprises a sequence from SEQ ID NO: 7 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 7:

(SEQ ID NO: 7)

MAPIQSSNMIQISHQINRLYVFGDSLSDVGNVYHASGKIYPPNPPYFEGR

YCNGLVWVEYLSAKLALTPEQNANFAYGGATTGNGSVNGVPGLLAQVQAF

TKVHQEVNSNALYVLWAGANDYLYGGANPTLTLGNISKAVESLLKMGAKK

IMVVNLPDLGKLPATRTSANSNTISSFAIAHNQSLAKSVEELKQKLGSDT

QIAILDIYSLYQEATKHPGMFGLTNVTNACSNNLAICDRPDKYLFWDGIH

PTTVAHRIIAEAALKVIKTEFSFSATSPQPLS, .

In some aspects, the polypeptide comprises a sequence from SEQ ID NO: 8 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 8:

(SEQ ID NO: 8)

MAPTTSITNCHTSINELYVFGDSLSDIGNVFNATEGFHPSSPPYFQGRFS

NGLVWVEYLASGLALTPKQNTNFAYGGATTGSGNINRIPDLLTQVDGFIK

IHQQVDRNALYILWAGANDYLHSMSNPSVSISNISQAIQSLAKVGAKKIL

VANLPDLGNIPATRNSPYSSILSSATIAHNLSLVKSLDILKQKLGHDSQM

IMLDVHSLYKEAIANPTKFGFINVTEACLNKLATCGNPDKFLFWDGIHPT

TAAHQILAKAALKELKTTYSFPPLPELLQ, .

In some aspects, the polypeptide comprises a sequence from SEQ ID NO: 9 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 9:

(SEQ ID NO: 9)

MAEGRQPFSRVVMFGDSLSDTGKMYKKMRGYLPSSPPYFNGRFSNGPVWL

EQLGDERFPGLVVANEAEGGATAVAYNHLGALNGWLGFWSWDPKYQVINN

LDYEIDQFLKKDKFRPDDLVVIWVGANDYLAYGWNTERDADRVIDTIRLA

SNRLVLNGAQQILLFNIPDLGQTPSARSMKVVEKVRHVASYHNQKLQNLT

RELAPLGIVKLFEVDKQFDEMMRDPQLFGLSDTEHACYGGGYTWKPFSGS

AAEVAATPALSVSERVAIAGNPILAQAVVSGQAKGRAATLNCDEHMFWDQ

VHPTRTVHKVLSQRVADFIDQHYEFVRH, .

In some aspects, the polypeptide comprises a sequence SEQ ID NO: 10 such as a functional homolog or variant thereof, e.g. comprising up to 1, 2, 3, 4, 5, 6, 7, 8, 9, 10, 11, 12, 13, 14, 15, 16, 17, 18, 19, 20, 25, 30, 35, 40, or more amino acid changes, such as substitutions or deletions, of SEQ ID NO: 10.

(SEQ ID NO: 10)

MMKKWLVCLLGLLALTAQAVERPSFSRIVMFGDSLSDTGKMYKKMKGYLP

SSPPYYEGRFSNGPVWLERLRDEHFPGLQLANEAEGGATAVAYNKLGWLN

FWAWDPKYQVINNLDYEIDQFLAKDSLRPDDLVVIWVGANDYLAYGWNQE

KDADRVIETIRLASNRLVLNGAQQILLFNIPDLGRTPSANSMKVVDQVRH

VASYHNQRLLNLSRELAPLGIVKMFEVDKQFDEMVGDPQKFGLSDIEHAC

YGGGYLWKPFSDASEAPALSVPERLAVAGNPILAQAVVSPQAARSAAARN

CDEHMFWDQVHPTATVHKAMGERVAAFIEQHYEFIRR, .

Specifically, the present disclosure provides a polypeptide comprising SEQ ID NO: 1, 2, 3, 4, 5, 6, 7, 8, 9, or 10 or their complementary sequences. The present disclosure also provides for a functional homologs or variant thereof, the polypeptide comprising at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to an exemplary polypeptide SEQ ID NO: 1, 2, 3, 4, 5, 6, 7, 8, 9, or 10.

The present disclosure also provides for fragments or smaller peptides of the polypeptide comprising at least 10, 15, 20, 25, 30, 35, 40, 45, 50, 55, 60, 65, 70, 75, 80, 85, 90, 95 or 100 or more consecutive bases of the exemplary polypeptide SEQ ID NO: 1, 2, 3, 4, 5, 6, 7, 8, 9, or 10. These smaller peptides of the exemplary polypeptide can be a fragment, a motif, an active site, or a binding site required for its function.

Functional Homologs

Functional homologs of the polypeptides described above are also suitable for use with the methods and kits described herein.

A functional homolog is a polypeptide that has some sequence similarity to the reference polypeptides or polynucleotides provided herein, and that carries out one or more of the biochemical or physiological function(s) of the reference polypeptide.

In some aspects the functional homolog and the reference polypeptide may be natural occurring. In some aspects the functional homolog and the reference polypeptide may be non-natural occurring, that is to say divergent from a wild-type (e.g. natural occurring) sequence.

The percent sequence similarity of the homologs provided by the present disclosure may be low due to convergent or divergent evolutionary events. As such, functional homologs can also be known as variants of homologs, orthologs, or paralogs.

Variants of a naturally occurring functional homolog are also encompassed by the present disclosure, such as, for example polypeptides encoded by mutants of a wild-type coding sequence, may themselves be functional homologs. Functional homologs can also be created by site-directed mutagenesis of the coding sequence for a polypeptide, or by combining domains from the coding sequences for different naturally-occurring polypeptides ("domain swapping").

The term "functional homolog" can also be applied to the nucleic acid that encodes a functionally homologous polypeptide. Techniques for modifying genes encoding the polypeptides provides herein are well known on the art. For example, to modify the DNA sequences one can use methods such as, but not limited to, directed evolution techniques, site-directed mutagenesis techniques, or random mutagenesis techniques. Such techniques can be useful to increase specific activity of a polypeptide, alter substrate specificity, alter expression levels, alter subcellular location, or modify the polypeptide's interactions in a desired manner that increase oil yield. Such modifications of the polynucleotides and polypeptides of the present disclosure are considered functional homologs encompassed by the present disclosure.

One method which can be used to identify functional homologs of the present disclosure can be by means of nucleotide or polypeptide sequence alignment. For example, performing a query on a database of nucleotide or polypeptide sequences can identify homologs of the polypeptides provided herein. The homologs can be identified using computer alignment and sequence identity software known in art or as provided herein.

Sequence analysis can involve BLAST, Reciprocal BLAST, or PSI-BLAST analysis of nonredundant databases using the amino acid sequence as the reference sequence provided herein. Amino acid sequence is, in some instances, deduced from the nucleotide sequence.

Polypeptides in the database that have greater than 40% sequence identity are candidates for further evaluation for suitability as functional homologs of the polypeptides of the present disclosure. Additionally, manual inspection of homolog candidates can be carried out. Manual inspection can be performed by selecting those candidates that appear to have conserved functional domains present in the polypeptides provided by the present disclosure.

Conserved regions can be identified by locating a region within the primary amino acid sequence of a polypeptide that is a repeated sequence, forms some secondary structure {e.g., helices and beta sheets), establishes positively or negatively charged domains, or represents a protein motif or domain. For example, see, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al, Nucl. Acids Res., 26:320-322 (1998); Sonnhammer et al., Proteins, 28:405-420 (1997); and Bateman et al., Nucl. Acids Res., 27:260-262 (1999). Conserved regions also can be determined by aligning sequences of the same or related polypeptides from closely related species. Closely related species preferably are from the same family. In some embodiments, alignment of sequences from two different species is adequate. Typically, polypeptides that exhibit at least about 40% amino acid sequence identity are useful to identify conserved regions. Conserved regions of related polypeptides exhibit at least 45% amino acid sequence identity (e.g., at least 50%, at least 60%), at least 70%>, at least 80%>, or at least 90%>amino acid sequence identity). In some embodiments, a conserved region exhibits at least 92%, 94%>, 96%>, 98%>, or 99% amino acid sequence identity. Sequence identity can be determined as described herein or by other methods known in the art.

Polypeptides with Phospholipase Activity

The disclosure provides numerous exemplary polypeptides, and the nucleic acids encoding them, having a phospholipase activity, as well as smaller peptides of the exemplary polypeptides encompassing the important active sites, regulatory, binding domains, or a combination thereof that impart its functional activity.

As used herein, the term "phospholipase" encompasses enzymes having any phospholipase activity, for example, cleaving a glycerolphosphate ester linkage (catalyzing hydrolysis of a glycerolphosphate ester linkage). In some aspects, polypeptides having phospholipase activity may have an activity comprising cleavage of a glycerolphosphate ester linkage, the ability to hydrolyze phosphate ester bonds, including patatin, lipid acyl hydrolase (LAH), phospholipase A, B, C and/or phospholipase D activity, or any combination thereof.

The phospholipase activity can comprise a phospholipase C (PLC) activity; a PI-PLC activity, a phospholipase A (PLA) activity, such as a phospholipase A1 or phospholipase A2 activity; a phospholipase B (PLB) activity, such as a phospholipase B1 or phospholipase B2 activity, including lysophospholipase (LPL) activity and/or lysophospholipase-transacylase (LPTA) activity, a phospholipase D (PLD) activity, such as a phospholipase D1 or a phospholipase D2 activity; or a patatin activity or any combination thereof. In some aspects, the phospholipase activity can further comprise a patatin enzymatic activity, including patatin esterase activity. In some aspects, the phospholipase activity can further comprise a lipid acyl hydrolase (LAH) activity.

Types of Phospholipase Enzymes

Natural occurring phospholipases enzymes can be found in both prokaryotes and eukaryotes. Several types of phospholipases are known which differ in their specificity according to the position of the bond attacked in the phospholipid molecule.

There are four major classes of phospholipase enzymes, distinguished by the type of reaction which they catalyze, termed: phospholipase A, phospholipase B, phospholipase C, and phospholipase D. Phospholipase types C and D are considered phosphodiesterases.

Phospholipase A can be further broken down into two subtypes, termed A1 and A2. Phospholipase A1 cleaves the SN-1 acyl chain. Phospholipase A2-cleaves the SN-2 acyl chain, releasing arachidonic acid. Phospholipase A2 acts on the intact lecithin molecule and hydrolyses the fatty acid esterified to the second carbon atom. The resulting products ca be lysolecithin and a fatty acid. Phospholipase B cleaves both SN-1 and SN-2 acyl chains; this enzyme is also known as a lysophospholipase. Enzyme that displays both PLA1 and PLA2 activities are often called a phospholipase B.

Phospholipase C cleaves before the phosphate, and can act to release diacylglycerol and a phosphate-containing head group. Phospholipase C can also be considered to be a phosphodiesterase.

Phospholipase D cleaves after the phosphate, releasing phosphatidic acid and an alcohol. Phospholipase D can also be considered to be a phosphodiesterase. Furthermore, phospholipase D can be further broken down into two subtypes, termed D1 and D2.

Families of phospholipase C (PLC) enzymes have been identified in bacteria and in eukaryotic trypanosomes. PLC enzymes belong to the family of hydrolases and phosphodiesterases. PLC participate in phosphatidylinositol 4,5-bisphosphate (PIP2) metabolism and lipid signaling pathways in a calcium-dependent manner. Studies on various Phospholipase C isoforms show that in some aspects these isoforms can differ in their mode of activation, expression levels, catalytic regulation, cellular localization, membrane binding avidity and tissue distribution. See (Carmen, G., J. Biol. Chem. 270 (1995) 18711-18714, Jianag, Y., J. Biol. Chem, 271 (1996) 29528-29532, Waggoner, D., J. Biol. Chem. 270 (1995) 19422-19429, Molecular Probes Product Sheet 2001, and Sano et al, Am. J. Physiol. Lung Cell Mol. Physiol. 281:844-851, 2001).

Phosphatidylinositol-specific phospholipase C (PI-PLC) enzymes are a family of eukaryotic intracellular enzymes which can play an important role in signal transduction methods. The PI-PLC catalyzed reaction is: 1-phosphatidyl-ID-myo-inositol 4,5-bisphosphate (also called PIP2, phosphatidylinositol bisphosphate)+H20→ID-myo-inositol 1,4, 5-trisphosphate (also called IP3, inositol triphosphate)+ diacylglycerol.

In one aspect, the PLC phospholipases can catalyze the hydrolysis of a variety of phospholipid substrates including phosphatidylcholine (PC), phosphatidylethanolamine (PE), phosphatidylserine (PS), phosphatidylinositol (PI), or phosphatidic acid (PA), or a combination thereof. In addition, these enzymes can have varying degrees of activity on the lysophospholipid forms of these phospholipids. For example they can provide hydrolysis for one type of phospholipid substrate at 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the original concentration and provide hydrolysis for another type of phospholipid substrate at 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 0.47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the original concentration.

One can test if a given phospholipase enzyme is encompassed by the present disclosure using comparative nuclear magnetic resonance (NMR) analysis of treated and non-treated oil as provided herein to determine the specific phospholipase substrate as well as the extent of hydrolysis obtained.

In some aspects, the polypeptides of the present disclosure can use a variety of phospholipid substrates including phosphatidylcholine (PC), phosphatidylethanolamine (PE), phosphatidylserine (PS), phosphatidylinositol (PI), and phosphatidic acid (PA), or a combination thereof. In one aspect, the function of the polypeptide is phospholipase activity. The phospholipase activity of the exemplary polypeptide can comprise a phospholipase C (PLC) activity, a phospholipase A (PLA) activity, such as a phospholipase A1 or phospholipase A2 activity, a phospholipase D (PLD) activity, such as a phospholipase D1 or a phospholipase D2 activity.

In another aspect, a phospholipase of the disclosure can have multifunctional activity. In some aspects, polypeptides of the present disclosure can comprise one phospholipase substrate activity, or any combination of phospholipase activities. For example, the phospholipase activity can comprise a specificity for PE and PC; PE and PI; PE and PS; PS and PC; PS and PI; PI and PC; PS, PI and PC; PE, PI and PC; PC, PE and PS; PE, PS and PI; or, PE, PS, PI and PC, or any combination thereof.

Polypeptides with Acyltransferase Activity

In one aspect, a polypeptide of the present disclosure is acyltransferase. In another aspect, the polypeptide is a lipid acyltransferase. In another aspect the polypeptide is a phosphatidylcholine-sterol O-acyltransferase.

In some aspects of the present invention the lipid acyltransferase is an enzymatic stabilizer and it works at 1/5, 1/6, 1/7, 1/8, 1/9, 1/10, 1/11, 1/12, 1/13, 1/14, 1/15, 1/16, 1/17, 1/18, 1/19, 1/20, 1/30, 1/40 or 1/50 of the recommended concentration for an oil degumming method.

In aspects the concentration of the lipid acyltransferase is not greater than 0.01 TIPU/g oil. In some aspects the concentration of the lipid acyltransferase enzyme is not greater than 0.002 TIPU/g oil. In some aspects the concentration of the lipid acyltransferase enzyme is not greater than 0.06 TIPU/g oil.

In some aspects the concentration of the lipid acyltransferase enzyme is about 0.01 TIPU/g oil. In some aspects the concentration of the lipid acyltransferase is about 0.002 TIPU/g oil. In some aspects the concentration of the lipid acyltransferase is about 0.06 TIPU/g oil.

Conditions and Polypeptides Activity

The polypeptides of the present disclosure can comprise homologs or variants of the exemplary polypeptides SEQ ID NO: 1, 2, 3, 4, 5, 6, 7, 8, 9, or 10. For example, the homologs or variants that can hybridize to SEQ ID NO: 1, 2, 3, 4, 5, 6, 7, 8, 9, or 10 under high or intermediate stringency conditions. The polypeptide can comprise functional fragments or positions of SEQ ID NO: 1, 2, 3, 4, 5, 6, 7, 8, 9, or 10. A functional fragment is a polypeptide that can perform substantial the same function in the methods provided in the present disclosure.

In one aspect, the polypeptide can retain its functional activity as provide herein under conditions comprising a temperature range of between about 37° C. to about 95° C., between about 55° C. to about 85° C., between about 70° C. to about 95° C., or between about 90° C. to about 95° C.

In another aspect, the polypeptide encompassed by the present disclosure can be thermotolerant. The polypeptide can retain a activity after exposure to a temperature in the range from greater than 37° C. to about 95° C., or in the range from greater than 55° C. to about 85° C. In one aspect, the exemplary polypeptide can retain its functional activity as provide herein after exposure to a temperature in the range from greater than 90° C. to about 95° C.

In one aspect, the polypeptide can retain its activity as provide herein under conditions comprising about pH 6.5, 6, 5.5, 5, 4.5 or 4. In another aspect, the polypeptide can retain its functional activity as provide herein under conditions comprising about pH 7, 7.5, 8.0, 8.5, 9, 9.5, 10, 10.5, or 11.

In some aspects the polypeptide has activity within a pH range of about pH 3 to pH 10. In some aspects the polypeptide activity within a pH range of about pH 4 to pH 9. In some aspects the polypeptide has activity within a pH range of about pH 5 to pH 9. In some aspects the polypeptide has activity within a pH range of about pH 4.5 to pH 9.5

Assays for Enzymatic Activity Levels

Phospholipase Activity in Oil

Untreated and degummed oil can be emulsified using for example an Ultra-Turrax T 50 Homogenizer (IKA) for 1 min. Next, 300 mg oil samples are extracted with 900 μl of NMR solution (100 mM Tris-HCl pH 10.5, 50 mM EDTA, 2.5% sodium deoxycholate) during 1 hr at 37° C. with constant agitation. The resulting aqueous phase can be extracted with 600 μl hexane and analyzed by NMR.

NMR spectra can be acquired using a Bruker DRX 600 equipment. Pure samples of PC, PE, PA, and PI can be run in parallel as standards. By comparing untreated and treated oil one can determine the extent of PC, PE, PA, and PI activity of a given polypeptide in an oil.

PC-PLC Activity

Briefly, 10 μl of sample containing PC-PLC was incubated with 10 mM O-(4-Nitrophenylphosphoryl)choline as a substrate in buffer 250 mM HEPES pH7, 0.1 mM ZnCl2 in a final volume of 100 μl at 55° C. for 30 min. Absorbance at 405 nm determined and PLC activity calculated. 1 PLC unit corresponds to the amount of enzyme releasing 1 μmol of p-nitrophenol per minute.

PI-PLC activity

PI-PLC activity can be determined using for example a water-soluble fluorogenic substrate butyl-FLIP (Toronto Research chemicals). One unit is the amount of enzyme that converts 1 umol of substrate (butyl-FLIP) to product per minute under the conditions specified.

Briefly, 2 mg/ml butyl-FLIP stock solution is prepared in H2O and stored at −20° C. Enzyme preparations (10-100 nM) are incubated with butyl-FLIP as a substrate in 50 mM sodium acetate buffer pH 5, 1 uM BSA, 0.04 mM butyl-FLIP. Assays can be carried out in a total volume of 0.2 mL in 96 well polycuvette and fluorescence is determined in a Synergy HT microplate reader with temperature maintained at 25° C.

Fluorescence spectra are recorded using excitation and emission filters of 485 and 528 nm respectively, and a slit width of 20 nm.

A 10-min time scan is recorded and the resulting change in fluorescence is converted to units of uM fluorescent product produced per second by making use of a calibration curve prepared by converting a solution of substrate completely to product by extended treatment with dilute sodium hydroxide.

LAT Activity

Lipid acyltransferase (LAT) activity can be determined by titration phospholipase units (TIPU) using for example the WAKO NEFAC kit. This kit utilizes an in vitro enzymatic colorimetric method for the quantitation of non-esterified (or free) fatty acids.

Briefly, 45 ul of a substrate solution containing 0.6% PC, 0.4% triton, 5 mM $CaCl_2$), 50 mM HEPES pH 7 is incubated with 5 ul of sample containing LAT enzyme for 10 min at 30° C. Afterwards 100 ul of NEFA A solution is added and incubated for 10 min at 37° C., following this incubation 200 ul of NEFA B solution is added and incubated for 10 min at 37° C., absorbance is measured at 520 nm using Synergy HT microplate reader. Enzyme activity TIPU can be calculated as micromole of FFA produced per minute.

Heterologous Sequence

The polypeptide or nucleotide sequences encoding for the polypeptide sequences can comprise a heterologous sequences.

The heterologous sequence can be one or more amino acid changes compared to the natural occurring sequence. The heterologous sequence can be one or more posttranslational modification compared to the natural occurring sequence.

In some aspects, the heterologous sequence can be an additional sequence located at the amino-terminal to, carboxy-terminal to, or on both ends of the polypeptide. The heterologous sequence can comprise a promoter, a leader sequence, a secretion signal, a signal peptide, a catalytic domain, an active site, a RNA or protein stabilizing sequence, or combination thereof.

In some aspects the heterologous polypeptide can comprises an exemplary polypeptide with at least one non-natural occurring posttranslational modification. Examples of non-natural occurring posttranslational modification that can occur on the heterologous polypeptides of the present disclosure include but are not limited to, glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, or disulfide bond reduction.

In some aspects the heterologous polypeptide can comprises the exemplary polypeptide with at least one glycosylation site not found in the natural occurring polypeptide. In one aspect, the non-natural occurring glycosylation can be an N-linked glycosylation. In one aspect, the non-natural occurring glycosylation can be an O-linked glycosylation. In one aspect the heterologous polypeptide can comprises, the exemplary polypeptide glycosylated at two or more the non-natural occurring sites after being expressed in a host cell.

The heterologous polypeptide or nucleotide sequence can comprises the exemplary polypeptide and one or more regulatory sequences as provided herein and known in the art. In some aspects, the heterologous polypeptide or nucleotide sequence can comprises the exemplary polypeptide and a cassette construct. In some aspects, the heterologous polypeptide or nucleotide sequence can comprises the exemplary polypeptide and a vector means as provided herein.

The present disclosure provides heterologous variants of SEQ ID NO: 1, 2, 3, 4, 5, 6, 7, 8, 9, or 10 by the use of alternative codon replacements. Such heterologous variant can be made by replacing the nucleic acid codons such that the codons facilitate the increase of its expression (e.g. are optimized) in a particular host cell. In some aspects, the exemplary sequences provided herein are optimized for the host cell, E. coll. The method for finding a modified nucleotide sequence of the present disclosure that increasing its expression in a particular host cell can comprises the steps of (a) providing a exemplary polynucleotide of the invention; (b) identifying a non-preferred or a less preferred codon in the nucleic acid and replacing it with a preferred or neutrally used codon encoding the same amino acid as the replaced codon, wherein a preferred codon is a codon over-represented in coding sequences in genes in the host cell and a non-preferred or less preferred codon is a codon under-represented in coding sequences in genes in the host cell, thereby modifying the exemplary polynucleotide of the invention to increase its expression in a particular host cell.

In some applications, the *E. coli* codon optimized DNA sequence of SEQ ID NO: 1 can be:

(SEQ ID NO: 11)

ATGGCGGCGTCAGAAAGAGACAACATTAACTTGAGCGAGTGGATGAGAGA
AATTCCTAACAGCAACACATTGGCAGAAATCAGCATTCCGGGAACACATG
ATTCAGGAACGTTTAGACTGGAAGACCCTATTAAAAGCGTGTGGGCAAAG
ACCCAGGAAAACGATTTCCGTTATCAAATGGACCACGGCGTCAGATTTTT
CGATATCCGCGGACGTGTCACCGATGACAACACTATTGTTCTGCATCACG
GTCCAATCTACTTGTACGTGACACTGCAACAATTCATCAACGAAGCGAAG
GAGTTCTTGAAGTCTCATCCTTCCGAAACGATTATCATGAGTCTGAAAGA
AGAGTATGAGTCTATGCCAGGCGCTAAAGAATCCTTTGCCAAGACTTTCG
AGAACATGTACTTTGGAGATTCCATTTTCTTGAAAACCGAAGGTAATATC
ACTCTGGGTGACTCACGTGGCAAGATTGTCCTGTTGCGTAGATATTCCGG
CTCAACCATGACTGGTGGCTTTAAAAACTTCGGATGGAAGGATAATGCTA
CATTTACGTCCACCACTAACGGTAATGTTAAAATTACCGTGCAGGACAAG
TACAACGTTAACTACGAAGAGAAAAAGGCTGCCATCGATTCAATGTTGAA
AGAAACTGTGCTGAACAAGGACAACCCAAATCATATTCACATCAATTTCA
CCTCTCTGTCTTCTGGTGGTACGGCATGGTCAAGCCCGTATTACTATGCG
TCTTACCTGAACAGCATTAGTGCAGCGAAAGTTCGCCTGGATCACTTGAA
AAATCTGGACACAAAGGCTGGTTGGATTATCATGGATTACATCGGCGATC
GTTGGGACCCAAAGCTGTATGAAGAGATTATCAGAGCCAACTTTCGCTAC
CCACCGACCGATGAACCGCATTTGTTTGAGCACATTGATGGCGAAGGAAT
CGACTTCACTAACCTGCCTCATAGTAAATGGAATGATCAAGTCAGTTCTA
TTCTGTTGAAGTCTTACACAGAGATCACGATCTACGAACACTCAAACTTC
ACTGGAAAGAGCGTTACCTTGACTAACACAACCAACTCTGCCCAACTGTT
CAACCTGACCACCTACAACTTCAATGATAAAATGTCCTCCTACACTTGGA
AACTGATTAGATAA, .

In some applications, the *E. coli* codon optimized DNA sequence of SEQ ID NO: 2 can be:

(SEQ ID NO: 12)

ATGGGAGTTAGACTGTCCGTTCAAGACTGGATGAGCGCATTGGGCGACGC
AACCCCTGTTCAAAGACTGACGATTCCGGGCACGCACGACTCCGGTGCAC
GTGTTGGTGGACCATGGGTGGCGTGTCAGAACACTCCTGTTGATGCTCAA
CTGAATAGCGGCATTAGATTTTTGGATGTCCGCTGCCGTGCAATTGACAA
CGTTTTCGCTATCCATCACGGTGCCTTTTATCAGGAACTGATGTTCGGCG
ATGTTTTGAATGCATGTCGTGCGTTTCTGCGTGCTCATCCGAGTGAGACA
GTGTTGATGAGAGTCAAACAAGAATACTCTGAAGTGGGTGCCGAAGAGTT
TCGTAGAATTTTCGGCATCTATCTGGATGACAAGGGATACCGCTCACTGT
TCCGTTTGGATGCCGGCCTGCCTACGTTGGGACAGGCAAGAGGTCGCGTT
GTGCTGTTGGCGGATTCTGACGGACTGGGAGGTGTCCGCTATGCAGATCC
ACAGTTGTTTGACATTCAAGATGACTATATGGCAGAAGCGTTTGGAAAAT
ACCCAAAGATCGAGGCGCAGTTCCGTAAAGCTGTGGCCCAACCGGGAAAG
CTGTTCGTCAACTACGTTTCAACCGCTGCCCTGTTGCCACCGAGAAGCAA
CGCCGATCGCCTGAATCCTCAAGTGAAACGTCTGTTGGAAGGTTCTGAGG
GCTCCGGATGGACTGGTTTGGGCATCGTCCCTATGGACTTTCCAAACGAA
AATGGCTTGGCAGAAACATTGATTAGACATAACTTGGCAGGACAGGGAGT
GAGATTGACAGCATAA, .

In some applications, the *E. coli* codon optimized DNA sequence of SEQ ID NO: 3 can be:

(SEQ ID NO: 13)

ATGGTCAAGAAGATTTTCCTGAACTTCCTGATTGGTATCGGACTGATTAT
CCTGAATAACTTTGTGTTTAGCGTGAATGAGGTGTTTGCTGATAGCCGCT
GGATGAGTACTATTCGTGATGACAAACCACTGAGTCGCGTCGCTGTTCCG
GGCACGCATGATTCTGGAACCTTCAAGATGTCTGACCCGATTATCTCCGC
CCTGGTGCGTACCCAGGAACAAGATTTTCGCCAGCAATTGGAGCAGGGTA
TTCGTTTCTTTGACATCCGTGGTAGAGCTACTAAAAACAATCAAATCGTG
CTGCATCACGGTCCTAAGTATCTGTTGGTCACACTGCACCAGTTCTTGCA
AGAAGCAGAGAATTTTCTGAGAAACAATCCATCAGAAACGATTATCATGA
GCTTGAAAGAAGAGTACCCGGCGATGGAAGAGGTCACCAAATCCTTTTTC
TCAATCTTCAAGGAATCTTACTTCAACTACTACCCTTTTTACACTGGCAA
CTCTTCCAATCCAAAAATTCAGGAGACACGTGGAAAGATCGTTCTGTTCG
ATAGAACTGGTAACTCCACATTGCCTGGCTACAACAAAATTTACAACTGG
GAAGACAACGCTACGTTTCAGACCACTACAAACAATACCCTGCCATTGTA
TGTTCAAGATGAGTATAATGCAACTTACAACCGTAAAACACATGCGATTC
TGGACCTGTTGAAGACCTCAAGCGAATCCAATGAGGGTATCTTTCTGAAC
TACGTTTCATTGGCTACGGGTGGCACCGCCTGGAGTTCTCCGTATTACTT
CGCCTCTTATCTGAACCCTTTGACTGGAGGTTACATTAATGAATTTCACG
TGAGCAACCCAGGCTGGGTTGTGATGGATTATAGTGGCAACAGATGGAAC
CCTAACCTGACAAAGAAAGTGATTGAGACTAATAGATACCTGCAATAA, .

In some applications, the *E. coli* codon optimized DNA sequence of SEQ ID NO: 4 can be:

(SEQ ID NO: 14)
ATGTCTATTTATTCCTCCGCAAACCTGAACGCTTGGATGGGCGAGTTGAA

AGACGACACACTGCTGTCCTCATTGAGTATCCCTGGCACCCATAACTCAC

CAACATGTCACGTTGCACCACCATCTGTGAGATGCCAGGCAGTCTCCCCG

CGTGAACAACTGGAGAATGGTGTTCGTTTCTTTGATATTAGAGTGCAGCC

TCAATATCCAGAAGATGCTGACAAAGATGAGCTGGCCTTGGTCCATTCTG

TTTTTCCGATCTCACTGACCGGCAGCAAGTACTTCCGCGATCTGATGCGT

GAAGTGAACGAGTTTTTGGACCAGAATCCGTCCGAAACACTGATTATCTC

ATTGAAAAGAGAAGGACCTGGAGAGCATACGGATCAGCAACTGAGTCGCA

TTTTGTCTGATCACTATGCCAGACCTGACTCACGCTGGTACACAAACCCG

AAAATCCCTACGCTGGGAGAAGTTCGCGGAAAGGTTGTGTTGATTCGTAG

ATTCGATATCCTGGACCATTTGAAAGATATTCACGGTGGCGCAGGCTGGG

GAATCTGTGCAAGCGGATGGGCGGACAACTGTAGCAATGCTACCTGCCCT

AGTGGTCAGCTGTGCATTCAAGATTTTTATGAGGTCTTGGAAACTGAGAA

CATTGGCGAAAAGATCAAGTACGTTCAAGAGCATTGTTTTAGAGCTGCCG

AAACCTGCTACCCATTCGGAGTTCTGCCGGACCATGAAGCTACTAAAGCC

CACCCATTTTATATTAACTTCCTGTCTGCTTCCAATTTCTGGAAGTTGGG

CACCTGGCCTGAGAAAATCGCCGGAAAGCTGAATCCAGCAGCGGTGGATT

ACTTGTGTCGTAAACACGGTGAAAAGGATGACTGCGATTGGTCCACCGGC

ATTCTGGTGACTGACTGGGTCGGTCTGGACGGCGATTGGGACTTGGTCAG

ATGCATTGTTGGTATGAACGCAAGACTGAAGTTGAGACAGGATAGACACG

AAGGAGATAATTAA, .

In some applications, the DNA sequence of SEQ ID NO: 10 can be:

(SEQ ID NO: 15)
ATGAAAAAAATGGCTTGTTTGTTTATTGGGGTTACTGGCGCTGACCGCTCA

GGCGGTGGAGCGCCCGAGCTTTTCCCGGATCGTGATGTTTGGTGACAGCC

TCTCGGACACCGGCAAGATGTACAAGAAGATGAAGGGGTATCTCCCCTCC

AGCCCTCCCTATTACGAGGGGCGTTTCAGCAATGGCCCGGTCTGGTTGGA

ACGGTTGCGAGACGAACACTTCCCCGGGCTTCAGCTGGCTAACGAGGCTG

AAGGTGGGGCGACGGCGGTGGCCTACAACAAGCTGGGCTGGCTCAACTTC

TGGGCCTGGGATCCCAAGTATCAGGTGATCAACAACCTCGACTACGAGAT

CGATCAGTTCCTGGCGAAGGACAGCTTGCGTCCCGACGATCTGGTGGTGA

TCTGGGTGGGGGCCAACGACTATCTGGCCTATGGCTGGAATCAGGAGAAA

GATGCCGATCGGGTGATCGAGACCATTCGCCTGGCATCCAACCGACTGGT

GCTCAACGGGGCGCAGCAGATCCTGCTGTTCAACATCCCGGATCTGGGCA

GAACTCCATCCGCCAACAGCATGAAGGTAGTGGATCAGGTGCGCCACGTA

GCCAGCTATCACAACCAGCGGCTGCTCAATCTCTCGCGCGAACTGGCCCC

CCTTGGCATCGTCAAGATGTTCGAAGTGGACAAGCAGTTTGACGAGATGG

TTGGTGATCCCCAGAAATTCGGGCTGAGCGACATCGAGCACGCCTGCTAT

GGCGGCGGGTATCTGTGGAAGCCCTTCTCCGATGCGAGCGAGGCGCCAGC

-continued

CTTGAGCGTCCCAGAGCGTCTGGCAGTGGCCGGCAACCCGATCCTGGCCC

AGGCTGTTGTGAGCCCGCAAGCGGCCCGCAGTGCGGCAGCCCGGAACTGC

GATGAACACATGTTCTGGGATCAGGTGCACCCGACTGCGACGGTGCACAA

GGCGATGGGGGAGCGGGTCGCCGCTTTCATCGAACAGCATTACGAGTTTA

TTCGTCGCTGA, .

In some applications, the *E. coli* codon optimized DNA sequence of SEQ ID NO: 10 can be:

ATGGTGGAACGCCCGAGTTTCTCACGTATTGTTATGTTTGGTGATAGTCT

GTCCGACACCGGCAAAATGTACAAGAAAATGAAAGGTTATCTGCCGAGCA

GCCCGCCGTATTACGAAGGTCGTTTTAGCAATGGTCCGGTGTGGCTGGAA

CGTCTGCGTGATGAACATTTCCCGGGTCTGCAACTGGCAAATGAAGCTGA

AGGCGGTGCCACGGCAGTTGCTTATAACAAACTGGGCTGGCTGAATTTTT

GGGCGTGGGACCCGAAATATCAGGTCATTAACAATCTGGATTACGAAATC

GACCAATTCCTGGCCAAAGATTCACTGCGTCCGGATGACCTGGTGGTTAT

TTGGGTTGGTGCGAACGATTATCTGGCCTACGGCTGGAATCAGGAAAAAG

ATGCAGACCGCGTCATTGAAACCATCCGTCTGGCATCCAACCGCCTGGTG

CTGAATGGTGCTCAGCAAATTCTGCTGTTTAACATCCCGGATCTGGGCCG

TACGCCGTCAGCGAACAGCATGAAAGTCGTGGACCAGGTGCGCCATGTTG

CCTCATATCACAACCAACGTCTGCTGAATCTGTCGCGCGAACTGGCCCCG

CTGGGTATCGTCAAAATGTTCGAAGTGGATAAACAGTTCGACGAAATGGT

GGGTGATCCGCAAAAATTTGGCCTGAGCGACATCGAACATGCATGCTATG

GCGGTGGCTACCTGTGGAAACCGTTCAGCGATGCTTCTGAAGCCCCGGCA

CTGTCTGTTCCGGAACGTCTGGCAGTTGCTGGTAACCCGATCCTGGCCCA

GGCAGTTGTCAGTCCGCAAGCCGCACGTTCCGCAGCTGCGCGTAATTGTG

ATGAACACATGTTCTGGGACCAGGTGCATCCGACCGCGACGGTTCACAAA

GCGATGGGCGAACGTGTGGCAGCATTTATTGAACAACATTATGAATTTAT

CCGTCGTTAA

Various methods are well known within the art for the amplification and isolation of the sequences provided by the present disclosure. By way of example, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesized, e.g. in an automatic DNA synthesizer, purified, annealed, ligated and cloned in appropriate vectors.

Alternatively a genomic DNA or cDNA library may be constructed. Labelled oligonucleotide probes may be synthesized and used to identify polypeptide-encoding clones from the genomic library prepared from the organism.

Alternatively, a labelled oligonucleotide probe containing sequences homologous to another known polypeptide gene could be used to identify polypeptide-encoding clones. In the latter case, hybridization and washing conditions of lower stringency are used. In yet another example of a method, one can obtain clones expressing the polypeptide and then use polymerase chain reaction to amplify the sequence of interest and isolated the nucleic sequence.

Polynucleotides of the present disclosure may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments are usefully in the identification of the protein in a library or a homologous variant provided by the present disclosure. Such primers, probes can be at least 15, 20, 25, 30, 35, or 40 nucleotide base pairs in length, and are also encompassed by the present disclosure.

In one aspect, the polypeptide or polynucleotide of the present disclosure can be in an isolated form. The term "isolated" can mean that the sequence is at least substantially free from at least one other component with which the sequence is naturally associated in nature and as found in nature. The term "isolated" can mean that the sequence has at least one other component that is not naturally found in nature.

In another aspect, polypeptide or polynucleotide of the present disclosure can be in a purified form. The term "purified" can be at least about 51% pure, or at least about 65% pure, or at least about 70% pure, or at least about 75%, or at least about 80% pure, or at least about 90% pure, or at least about 95% pure, or at least about 98% pure or at least about 99% pure.

Identification of Homologs

The present disclosure also provides methods of discovering phospholipase homologs encompassed by the present disclosure by using the nucleic acids, polypeptides and fragments provided herein. As such, the present disclosure also encompasses the use of nucleotide sequences that are capable of hybridizing to the sequences that are complementary to the sequences provided herein, derivative, or any fragment thereof. The present disclosure also encompasses sequences that are complementary to sequences that are capable of hybridizing to the sequences.

In general, hybridization conditions are chosen based on the melting temperature (Tm) and/or length of the nucleotide complex. See Berger and Kimmel (1987, Guide to Molecular Cloning Techniques, Methods in Enzymology, Vol. 152, Academic Press, San Diego Calif.).

Polynucleotide sequences that are capable of hybridizing to the nucleotide sequences provided herein under conditions of intermediate to maximal stringency are encompassed by the present disclosure. Preferably, the sequence will also have the functional properties as provide herein.

As a general guideline and not being bound to any particular theory, a maximum stringency hybridization can be used to identify sequences that are highly identical, of about 90% to 100% sequence identity to the sequences encompassed by the present disclosure, while an intermediate stringency hybridization can identify sequences, of about 90% to 70% sequence identity to the polynucleotides encompassed by the present disclosure.

Maximum stringent hybridization conditions typically occurs at about Tm−5° C. (5° C. below the Tm of the probe), high stringency at about 5° C. to 10° C. below Tm, intermediate stringency at about 10° C. to 20° C. below Tm, and low stringency at about 20° C. to 25° C. below Tm. By way of example only, highly stringent conditions can comprise: hybridization at about 42° C. in a hybridization solution comprising 25 mM KPO4 (pH 7.4), 5×SSC, 5×Denhart's solution, 50 μg/mL denatured, sonicated salmon sperm DNA, 50% formamide, 10% Dextran sulfate, and 1-15 ng/mL SEQ ID NO: 1, 2, 3, 4, 5, 6, 7, 8, 9, or 10 washing at about 65° C. in a wash solution comprising 0.2×SSC.

Oil Degumming

Briefly, 3 g of crude soybean oil containing about 1000 ppm phosphate will be homogenized for about 1 min using Ultra-Turrax T8 Homogenizer (IKA) with about 22.5 μg of the protein interest in 90 μl of buffer comprising NaCitrate 50 mM pH 6.2, 1 mM $ZnCl_2$. Next, tubes containing the reaction mixture will be incubated at about 50° C. with constant agitation using a magnetic tumble stirrer such as the VP 710 magnetic tumble stirrer (VP-Scientific). Next the oil will be homogenized and 200 μl of the homogenized oil were mixed with 200 μl of 2 M Tris-HCl pH 8 to stop the reaction at various time points (for example, between 60-120 min). Then, 800 μl of water will be added to the mixture and incubated for 1 h at 37° C. with constant agitation, and then centrifuged for about 5 min at 14000 g. Finally, 45 μl of the aqueous phase will be recovered and treated with 0.3 U of calf intestinal phosphatase (Promega, WI, USA) for 1 h at 37° C.

The concentration of inorganic phosphate can be determined according to the method of Sumner (Sumner, J. B., Science 1944 196: 413). Briefly, a 500 μl sample, containing 0.025 to 0.25 μmol of inorganic phosphate in 5% TCA was mixed with 500 μl of color reagent (4% $FeSO_4$, 1% $(NH_4)_6MoO_{24}.H_2O$, 3.2% $H_2SO_4$). Spectrophotometric readings should be made at about 700 nm, and the micromoles of inorganic phosphate in the sample can be calculated using a standard curve.

Comparative Nuclear Magnetic Resonance Analysis

Oil samples can be extracted with about 900 μl of NMR solution (100 mM Tris-HCl pH 10.5, 50 mM EDTA, 2.5% sodium deoxycholate) during 1 h at 37° C. with constant agitation step. The resulting aqueous phase can be extracted with 600 μl hexane and then analyzed by NMR analysis.

NMR spectra of the crude oil and treated crude oil can by acquired using a Bruker DRX 600 and samples of pure phosphatidylcholine, phosphatidylethanolamine, phosphatidic acid and phosphatidylinositol control can be run as standards.

F. Isolated Polypeptides

The present disclosure provides isolated polypeptides enzyme compositions. In some aspects, the isolated polypeptides enzyme comprises an exemplary sequence or functional homolog of variant thereof as provided herein. In some aspects, the isolated polypeptide enzyme comprises an exemplary sequence or homolog and at least one heterologous sequence or nucleotide. In some aspects the isolated polypeptide enzyme is a phospholipase C comprising at least one heterologous sequence or nucleotide.

In some aspects the isolated polypeptide enzyme is a phosphatidylinositol-specific phospholipase C comprising at least one heterologous sequence or nucleotide. In some aspects the isolated polypeptide enzyme is a phosphatidylethanolamine-specific phospholipase C comprising at least one heterologous sequence or nucleotide. In some aspects the isolated polypeptide enzyme is a phosphatidylcholine-specific phospholipase C comprising at least one heterologous sequence or nucleotide.

In some aspects the isolated polypeptide enzyme is a phosphatidylethanolamine-specific phospholipase C and a phosphatidylcholine-specific phospholipase C comprising at least one heterologous sequence or nucleotide.

In some aspects the isolated polypeptide enzyme can be used for an oil degumming method. In some aspects the isolated enzymes as provided herein is used for an oil degumming method of an edible oil or biofuel for production of a consumer product. For example, the isolated enzymes can be used to method oils and phospholipids in different forms, including crude forms, degummed, gums, wash water, clay, silica, soapstock, and the like.

In some aspects the biofuel can be a composition of an oil or a fat. In some aspects the biofuel can be a composition comprising fish oils, animal oils, plant oils, algae oils, a vegetable oil, a straight vegetable oil, a virgin vegetable oil, a waste vegetable oil, an animal fat, a grease, a tallow, a lard, or a yellow grease. In some aspects the biofuel can be a composition comprising a lipid or an alkyl ester. The isolated polypeptide enzyme can be used to make an enzymatic mixture used in the processing or refining of a crude oil, an edible oil, a biofuel or to method oils and phospholipids in different forms, including crude forms, degummed, gums, wash water, clay, silica, soapstock, and the like.

The isolated polypeptide comprising phosphodiesterase activity can be obtained from a culture media of the genus *Lysinibacillus, Streptomyces, Enterococcus*, or *Aspergillus*. In another aspect, the isolated polypeptide comprising phosphodiesterase activity can be obtained from a culture media of the species *Lysinibacillus sphaericus, Streptomyces antibioticus, Enterococcus faecalis*, or *Aspergillus flavus*.

In some aspects, enzymes can be obtained from a culture media of a genetically modified microorganism, such as an *E. coli* strain modified to harbor a sequence encoding a phosphodiesterase from the genus *Lysinibacillus, Streptomyces, Enterococcus*, or *Aspergillus*. In some aspects, enzymes can be obtained from a culture media of a genetically modified *E. coli* strain harboring a sequence encoding a phosphodiesterase from the species *Lysinibacillus sphaericus, Streptomyces antibioticus, Enterococcus faecalis*, or *Aspergillus flavus*.

In some aspects, the isolated polypeptide enzyme can be obtained from a culture media of a genetically modified *E. coli* strain harboring a phosphodiesterase encoded by an exemplary SEQ ID NO: 1, 2, 3, or 4. The present disclosure also encompasses the use of any homolog, derivative, fragment, or enzymatic derivative thereof of the exemplary sequence capable of achieving the methods as illustrated herein.

In some aspects, the homologs, variants, fragments or derivatives comprises at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4 and provides the similar functional benefits to the enzymatic method for refining a crude oil as provided herein. In some aspects, a homolog, variant, fragment, or enzymatic derivative thereof may comprise conservative amino acid substitutions of the exemplary sequence.

The isolated lipid acyltransferases enzyme can be obtained from a culture media of the genus *Nostoc, Fischerella, Scytonema*, or *Aeromonas*. The isolated polypeptide lipid acyl transferase can be obtained from a culture media of the species *Nostoc punctiformes, Fischerella muscicola, Scytonema* spp., *Aeromonas veronii*, or *Aeromonas enteropelogenes*.

In some aspects, enzymes can be obtained from a culture media of a genetically modified microorganism, such as an *E. coli* strain modified to harbors a sequence encoding a lipid acyltransferases from the genus *Nostoc, Fischerella, Scytonema*, or *Aeromonas*. In some aspects, enzymes can be obtained from a culture media of a genetically modified *E. coli* strain harboring a sequence encoding a lipid acyltransferase from *Nostoc punctiformes, Fischerella muscicola, Scytonema* spp., *Aeromonas veronii*, or *Aeromonas enteropelogenes*. In some aspects, enzymes can be obtained from a culture media of a genetically modified *E. coli* strain harboring a lipid acyl transferase encoded by the sequence of SEQ ID NO: 6, 7, 8, 9, or 10.

In some aspects, the isolated polypeptide enzyme can be obtained from a culture media of a genetically modified *E. coli* strain harboring a lipid acyltransferase encoded by an exemplary SEQ ID NO: 6, 7, 8, 9, or 10. The present disclosure also encompasses the use of any homolog, derivative, fragment, or enzymatic derivative thereof of the exemplary sequence capable of achieving the methods as illustrated herein. In some aspects, the homologs, variants, fragments or derivatives comprises at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10 and provides the similar functional benefits to the enzymatic method for refining a crude oil as provided herein. In some aspects, a homolog, variant, fragment, or enzymatic derivative thereof may comprise conservative amino acid substitution of the exemplary sequence provided by the present disclosure.

Production of Polypeptides

Large-scale production of polypeptides of the present disclosure can be obtained by the culturing of the genetically modified organisms provided herein. By way of example only, large-scale production can be obtained by the following method:

a) A nucleic acid molecule encoding a codon optimized version of a gene or functional homolog encoding SEQ ID NO: 2, 3, 4, 5, 6, 7, 8, 9, or 10) is cloned into any suitable vector such as for example a pET24b plasmid (Novagen, USA) or host cell.

b) The resulting plasmid can be transformed by electroporation or any other means into a host cell organism such as the BL21A1 *E. coli* strain. Transformed colonies can be selected in LBA plates containing 50 mg/L Kanamycin.

c) A colony of the recombinant clone can be grown on 100 ml of LB at 37° C. until cell density reaches about OD600=2.

d) The culture can be transferred to a seed fermentor containing about 10 liters (L) of medium (such as HM media described below) and grown for 10 hrs at 35° C.

e) The culture can be transferred to a 1000 L fermentor containing about 600 L of HM medium or the a like and grown at about 35° C. until glycerol exhaustion. An exponential feeding of a nutrient solution containing about 80% w/v glycerol and about 20 g/L $MgSO^4$ is then initiated at a rate sufficient to maintain the specific grow rate at a value of about 0.35 h-1±0.05. When $OD_{600}$ reaches a value of about 80, about 1 mM IPTG is added and the nutrient solution is fed at a constant rate of about 9±1 L/h for 10 hrs. Dissolved oxygen concentration is kept above about 30% of saturation by enrichment of the air stream with pure oxygen when necessary. The pH is maintained at about 7 by the addition of $NH_4OH$ as necessary.

f) At the end of the fermentation method, the broth can be treated with three cycles of compression/decompression at about 1000 bar in an APV homogenizers to disrupt the host cells.

g) The resulting liquid can be centrifuged until clarification to separate solid materials in a sharpless centrifuge at about 5000 g.

h) $(NH_4)_2SO_4$ is added to about 80% saturation to the clarified liquid, the mixture can be incubated at 8° C. for 3 hrs and then centrifuged at 5000 g to obtain a brown paste.

Variants and Fragments

The disclosure provides methods for determining a functional homologs, variants, fragments or derivatives of enzymes of the present disclosure comprising the steps of: (a) providing a homolog variants, fragments or derivatives of enzymes comprising an amino acid sequence of the invention; and, (b) deleting a plurality of amino acid residues from the sequence of step (a) and testing the remaining subsequence for a given activity as provide herein, thereby determining a functional fragment.

Variants of the exemplary polypeptides encompassed by the present disclosure can include those wherein conservative substitutions have been introduced. A conservative substitution is recognized in the art as a substitution of one amino acid for another amino acid that has similar properties. Amino acids can be classified according to physical properties and contribution to secondary and tertiary protein structure.

In one aspect, the conservative amino acid substitutions can be as described as

Conservative Substitutions I

Side Chain Characteristic: Substitution Amino Acid Residues

Aliphatic: G A P

Non-polar: I L V

Polar—uncharged: C S T M N Q

Polar—charged: D E K

Aromatic: H F W Y

Other: NODE

Alternatively, conservative amino acids can be as described in Table Y. See Lehninger, [Biochemistry, Second Edition; Worth Publishers, Inc. NY, N.Y. (1975), pp. 71-77].

Table Y: Conservative Substitutions II

Side Chain Characteristic: Amino Acid

Non-polar (hydrophobic)

Aliphatic: A L I V P

Aromatic: F W

Sulfur-containing: M

Borderline: G

Uncharged-polar

Hydroxyl: S T Y

Amides: N Q

Sulfhydryl: C

Borderline: G

Positively Charged (Basic): K R H

Negatively Charged (Acidic): D E

As still another alternative, exemplary conservative substitutions can be described in as:

Conservative Substitutions III

Original Residue: Exemplary Substitution Residues

Ala (A): Val, Leu, He

Arg (R): Lys, Gin, Asn

Asn (N): Gin, His, Lys, Arg

Asp (D): Glu

Cys (C): Ser

Gin (Q): Asn

Glu (E): Asp

His (H): Asn, Gin, Lys, Arg lie (I) Leu, Val, Met, Ala, Phe,

Leu (L): He, Val, Met, Ala, Phe

Lys (K): Arg, Gin, Asn

Met (M): Leu, Phe, lie

Phe (F): Leu, Val, lie, Ala

Pro (P): Gly

Ser (S): Thr

Thr (T): Ser

Trp (W): Tyr

Tyr (Y): Trp, Phe, Thr, Ser

Val (V): He, Leu, Met, Phe, Ala

A variant homologs may also be obtained using degenerate PCR which will use primers designed to target sequences encoding conserved amino acid sequences within the sequences of the present disclosure. In general, homologs will comprise conserved sequences that code for important functional domains, active sites, ect. of the provided sequences herein.

Conserved sequences provided by the present disclosure can be predicted, for example, by aligning the amino acid sequences from several variants homologs. For constructing and refining multiple sequence alignments to identify conserved functional domains you can use computer software for example PileUp, SeqLab, and the GCG Wisconsin program suite.

For example phospholipase activity can be measured by providing a phospholipase substrate and detecting a decrease in the amount of the substrate (e.g. such as an oil comprising phospholipid) or an increase in the amount of a reaction product in parallel with appropriate experimental controls.

Likewise, lipid acyltransferase activity can be measured by providing a lipid acyltransferase substrate (e.g. such as cholesterol) and detecting an increase in the amount of the substrate or a decrease in the amount of a reaction product.

Percent Sequence Identity or Similarity

Sequence identity calculations can be conducted manually, or more usually, with the aid of publically available sequence comparison programs. These commercially available computer programs can calculate percent sequence identity, or percent sequence similarity (i.e. amino acid residues having similar chemical properties/functions) between two or more sequences.

The percent sequence identity or percent sequence similarity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

The degree of polypeptide identity with regard to a sequence may be determined over the whole amino acid sequence. Suitably, the degree of percent sequence identity, or percent sequence similarity with regard to a polypeptide sequence is determined over at least 20 contiguous amino acids, at least 30 contiguous amino acids, 40 contiguous amino acids, 50 contiguous amino acids, 60 contiguous amino acids, or at least 100 contiguous amino acids.

The degree of polynucleotide identity with regard to a sequence may be determined over the whole nucleotide sequence. Suitably, the degree of percent sequence identity, or percent sequence similarity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

The calculation of maximum percent sequence identity, or percent sequence similarity between two or more sequences can often require optimal alignment between the sequences. Such alignment in general required consideration gap penalties. After the computer software has produce the most optimal alignment, then one should calculate of percent sequence identity, or percent sequence similarity.

Examples of computer program for carrying out such optimal alignments include, but are not limited to, BLAST (see Ausubel et al. 1999 Short Protocols in Molecular Biology, 4th Ed-Chapter 18), and FASTA (Altschul et al. 1990 J. Mol. Biol. 403-410) or commercially available programs such as Vector NTI (Life Technologies) based on an algorithm, analogous to CLUSTAL (Higgins D G & Sharp P M (1988), Gene 73(1), 237-244), or the a like.

Typically, these programs will allow a user to allow the gap penalties to be modified. However, depending on the specific complexity, length, or number of sequences being aligned it will be preferred to use the default values when using such software programs.

When the computer program provides consideration for "gap penalties", it will produce an alignment with as few gaps as possible—reflecting higher relatedness between the two compared sequences—and as a results will achieve a higher score than compared to an alignment method that produces many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps.

Stabilizers

An isolated polypeptide enzyme or enzymatic mixture is often unstable when not in its native cellular environment. If certain buffer conditions are not maintained, the isolated polypeptide may not function properly or can lose activity as a result of proteolysis, aggregation and suboptimal buffer conditions. Optimal conditions for storage are distinctive to each protein.

In some aspects, the isolated polypeptide enzyme of the present disclosure can further comprise one or more stabilizing reagents which protect the proteins comprising the mixture from environmental stresses that can otherwise lead to enzyme inactivation, aggregation and freeze-thaw damage.

Example of additives that can be used with the isolated polypeptide enzymes or the enzymatic mixtures of the present disclosure can include but are not limited to: Protein Stabilizing Cocktail solution to extend the shelf-life for storage at 4° C. or −20° C. Cryoprotectants such as glycerol or ethylene glycol to a final concentration of about 25-50% help to stabilize proteins by preventing the formation of ice crystals at −20° C. Protease inhibitors prevent proteolytic cleavage of proteins disulfide bonds within a protein structure. Anti-microbial agents such as sodium azide (NaN3) at a final concentration of about 0.02-0.05% (w/v), or thimerosal at a final concentration of about 0.01% (w/v) inhibit microbial growth. Metal chelators such as EDTA at a final concentration range of about 1-5 mM avoid metal-induced oxidation of —SH groups and helps to maintain the protein in a reduced state. Reducing agents such a dithiothreitol (DTT) and 2-mercaptoethanol (2-ME) at final concentrations of 1-5 mM also help to maintain the protein in the reduced state by preventing oxidation of cysteine residues.

Example of stabilizing reagents that can be used with the isolated polypeptide enzymes or enzymatic mixtures of the present disclosure can include but are not limited to: can comprise for example, glycerol, ethyleneglycol, trehalose, glucosylglycerol and glucosylglycerate, azide, mercury. Suitable stabilizing reagents can also comprise commercially available stabilizing reagents such as, Stabilizing Cocktails such as Protein Stabilizing Cocktail (Pierce) Ethylene Glycol (Pierce), SuperFreeze™ Peroxidase Conjugate Stabilizer (Pierce), Guardian Peroxidase Conjugate Stabilizer/Diluent (Pierce), Halt™ Protease Inhibitor Cocktail kit with EDTA (Pierce), Halt™ Protease Inhibitor Cocktail EDTA free (Pierce), PMSF (Phenylmethylsulfonyl fluor) (Pierce), Thermo Scientific Protein Stabilizing Cocktail (Life technologies), COMPLETE and PHOSSTOP (Roche), and other know or new in the art of protein stabilization.

In this method the lipid acyltransferase is an enzymatic stabilizer of the other enzymes, and produces an increase of the half life time of the other components of the enzymatic mixture, particularly the lipid acyltransferse increase the half life time of the polypeptides that has phosphatidylinositol-specific phospholipase activity, a phosphatidylcholine and phosphatidylethanolamine-specific phospholipase activity.

The inventors of the present invention have surprisingly found that a lipid acyltransferase acts as an enzymatic stabilizer. This it means that this enzimatic stabilizer maintain 80-90% activity level of PLC enzymes at least for a year of storage in aqueous solution and also maintain PLC activity in oil over 80% initial activity for at least 6 hours. Preferably, for this invention said enzymatic stabilizer is a lipid acyltransferase from *Aeromonas enteropelogenes*. The enzymatic stabilizer stabilize other enzymes, and produces an increase of the half life time of the other components of the enzymatic mixture, particularly the lipid acyltransferse increase the half life time of the polypeptides that has phosphatidylinositol-specific phospholipase activity, a phosphatidylcholine and phosphatidylethanolamine-specific phospholipase activity.

G. Enzymatic Mixtures

The present disclosure provides numerous enzymatic mixture compositions comprising an isolated polypeptide enzyme as provided herein. In some aspects, the present disclosure provides the enzymatic mixture, wherein the polypeptide enzymes are provided from a commercial source. In some aspects, the present disclosure provides the enzymatic mixture comprising a combination of a commercially available polypeptide enzyme and the isolated polypeptide enzyme provided herein.

The present discourse provides for isolated enzymes and mixtures to be stored and shipped to consumer who are in the oil processing and refinement industry. As those skilled in the art appreciate will appreciate, the enzymatic mixtures of the present disclosure can further comprise a stabilizing reagents or an additive.

The present disclosure provides for an enzymatic mixture comprising: a phosphatidylinositol-specific phospholipase (PI-PLC), a phosphatidylcholine and phosphoethanolamine-specific phospholipase (PC/PE-PLC).

The present disclosure provides for an enzymatic mixture comprising: a phosphatidylinositol-specific phospholipase (PI-PLC), a phosphatidylcholine and phosphoethanolamine-specific phospholipase (PC/PE-PLC), and a lipid acyltransferase (LAT).

The present disclosure provides for an enzymatic mixture comprising: a phosphatidylinositol-specific phospholipase (PI-PLC), a phosphatidylcholine and phosphoethanolamine-specific phospholipase (PC/PE-PLC), and a lipid acyltransferase (LAT), wherein the enzymatic mixture does not comprise a phospholipase A (PLA). In some aspects the lipid acyltransferase is a polypeptide that at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6, 7, 8, 9, or 10. In some aspects the lipid acyltransferase produces lysophospholipids and acylesterol when reacting with a crude oil.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase, and lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure proved for enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the amino acid sequences of SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 0.19%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase and lipid acyltransferase, wherein lipid acyltransferase has at least 40%, 41%, 42%, 43%, 44%, 45%, 46%, 47%, 48%, 0.19%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 31%, 32%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 0.49%, 50%, 51%, 52%, 53%, 5.4%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 3.4%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 32%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 31%, 82%, 83%, 3.4%, 85%, 86%, 37%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 31%, 32%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the amino acid sequences of SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase and a lipid acyltransferase, wherein the lipid acyltransferase and has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase and a lipid acyltransferase, wherein the lipid acyltransferase has at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the amino acid sequences of SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase and a lipid acyltransferase, wherein the lipid acyltransferase has at least 40%, 41%, 42%, 43%, 44%, 45%, 46%, 47%, 48%, 0.19%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the amino acid sequences of SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity SEQ ID NO: 3, a phosphatidylcholine and phosphoethanolamine-specific phospholipase comprising at least %, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 31%, 32%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 0.49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 3.4%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, a phosphatidylcholine and phosphoethanolamine-specific phospholipase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 31%, 32%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 0.49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 3.4%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture comprising: a phosphatidylinositol-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, a phosphatidylcholine and phosphoethanolamine-specific phospholipase comprising at least 40%, 41%, 42%, 43%, 44%, 45%, 46%, 0.17%, 48%, 49%, 50%, 51%, 52%, 53%, 54%, 55%, 56%, 57%, 58%, 59%, 60%, 61%, 62%, 63%, 6.4%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a lipid acyltransferase, wherein the lipid acyltransferase has at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, and a polypeptide with at 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7, wherein the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some aspects the enzymatic mixture does not comprise a phospholipase A.

The present disclosure provides for an enzymatic mixture for oil degumming comprising: a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, and a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some aspects the enzymatic mixture does not comprise a phospholipase A.

Applications for Enzymatic Mixtures

In some aspects the enzymatic mixture or isolated polypeptide as provided herein is used for oil refining of oil compositions. The enzymatic mixture or isolated polypeptide as provided herein can be incorporated into either a chemical or physical oil refining method.

In some aspects the enzymatic mixture or isolated polypeptide provided herein is used for oil refining of an edible oil. In some aspects the enzymatic mixture or isolated polypeptide as provided herein is used for oil refining of a crude biofuel. In some aspects the enzymatic mixture can hydrolyze greater than 80% (w/w) of phospholipids in the edible oil into diacylglycerol and phosphate ester when used for oil refining of an oil. In some aspects enzymatic mixture can increase the oil yield by at least 1%, 2%, 3%, 4%, 5%, 6%, 7%, 8%, 9%, 10%, 11%, 12%, 13%, 14%, 15%, 16%, 17%, 18%, 19%, 20%, compared to a non-enzymatic degumming method when used for oil refining of an oil. In some aspects enzymatic mixture can increase the oil yield by at least 1%, 2%, 3%, 4%, 5%, 6%, 7%, 8%, 9%, 10%, 11%, 12%, 13%, 14%, 15%, 16%, 17%, 18%, 19%, 20%, compared to an enzymatic degumming method when used for oil refining of an oil. In some aspects the enzymatic mixture does not increase the free fatty acid content in the oil composition when used for oil refining of an oil. In some aspects the enzymatic mixture of the phosphatidylinositol-specific phospholipase, and the phosphatidylcholine and phosphatidylethanolamine-specific phospholipase is maintained at a 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% activity level when used for oil refining of an oil. In some aspects the enzymatic mixture of the phosphatidylinositol-specific phospholipase, and the phosphatidylcholine and phosphatidylethanolamine-specific phospholipase is maintained at a range of 70%-75%, 70%-80%, 75%-80%, 80%-85%, 80%-90%, 90%-95%, activity level when used for oil refining of an oil. In some aspects the enzymatic mixture's phosphatidylinositol-specific phospholipase or the phosphatidylcholine and phosphatidylethanolamine-specific phospholipase has higher activity compared to an enzymatic oil degumming method without a lipid acyltransferase when used for oil refining of an oil. In some aspect the affects above are accomplished wherein the lipid acyltransferase enzyme provided in the enzymatic mixture is at one tenth of the recommended concentration for an enzymatic oil degumming method with a lipid acyltransferase activity.

In some aspects the enzymatic mixture or isolated polypeptide as provided herein is used for an oil degumming method of a crude oil. In some aspects the enzymatic mixture or isolated polypeptide as provided herein is used for an oil degumming method of an edible oil. In some aspects the enzymatic mixture or isolated polypeptide as provided herein is used for an oil degumming method of a biofuel.

The present disclosure provides an oil for a consumer product comprising detectable amounts of a polypeptide with at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 2, 3, or 4. In some aspects, the consumer product is a food, a cosmetic, or a fuel for a vehicle. In some aspects, the oil does not comprise detectable amounts of a phospholipase A.

The present disclosure provides an oil for a consumer product comprising detectable amounts of a polypeptide with at least 40%, 41%, 42%, 43%, 44%, 45%, 46%, 0.47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 5, 6, 7, 8, 9, or 10. In some aspects, the consumer product is a food, a cosmetic, or a fuel for a vehicle. In some aspects, the oil does not comprise detectable amounts of a phospholipase A.

H. Oil Mixtures

The present disclosure provides for an oil mixture comprising: a crude oil, a phosphatidylinositol-specific phospholipase C, and a lipid acyltransferase. In some embodiments the oil mixture does not comprise a phospholipase A. In some embodiments the oil mixture can further comprise, a, a phospholipase C.

In some aspects the oil mixture comprises an edible oil. In certain aspects, the edible oil mixture comprises: a soybean oil, rapeseed oil, sunflower seed oil, rice bran oil, palm oil, sesame oil, peanut oil, acai oil, almond oil, babassu oil, blackcurrent seed oil, borage seed oil, canola oil, cashew oil, castor oil, coconut oil, coriander oil, corn oil, cottonseed oil, *crambe* oil, flax seed oil, grape seed oil, hazelnut oil, other nut oils, hempseed oil, jatropha oil, jojoba oil, linseed oil, macadamia nut oil, mango kernel oil, meadowfoam oil, mustard oil, neat's foot oil, olive oil, palm oil, palm kernel oil, palm olein oil, pecan oil, pine nut oil, pistachio oil, poppy seed oil, rapeseed oil, rice bran oil, safflower oil, sasanqua oil, shea butter oil, tall oil, tsubaki oil, walnut oil, or a combination thereof.

In some aspects the oil of the mixture comprises a biofuel. In certain aspects the biofuel oil mixture comprises: a corn oil, vegetable oil, *Neochloris oleoabundans* oil, *Scenedesmus dimorphus* oil, *Euglena gracilis* oil, *Phaeodactylum tricornutum* oil, *Pleurochrysis carterae* oil, *Prymnesium parvum* oil, *Tetraselmis chui* oil, *Tetraselmis suecica* oil, *Isochrysis galbana* oil, *Nannochloropsis salina* oil, *Botryococcus braunii* oil, *Dunaliella tertiolecta* oil, *Nannochloris* species oil, *Spirulina* species oil, Chlorophycease oil, Bacilliarophy oil, or a combination thereof.

The crude oil in the oil mixture can be a whole crude oil, a partially crude oil, a partially refined oil, or a substantially refined oil. Whole crude oil can be provided from conventional A crude oil can include oil that has undergone some method or pre-treatment.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some embodiments the oil mixture can further comprises, a phospholipase C. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some embodiments the oil mixture can further comprises a phospholipase A, a phospholipase B, a phospholipase C, or a phospholipase D. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some embodiments the oil mixture can further comprises a phospholipase A, a phospholipase B, a phospholipase C, or a phospholipase D. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 6. In some embodiments the oil mixture can further comprises, a phospholipase C. In some aspects the enzymatic mixture does not comprise a phospholipase A.

The present disclosure provides for a crude oil mixture comprising: an oil composition, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some embodiments the oil mixture can further comprises a phospholipase A, a phospholipase B, a phospholipase C, or a phospholipase D. In some aspects the enzymatic mixture does not comprise a phospholipase A.

The present disclosure provides for a crude oil mixture comprising: a oil composition, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some embodiments the oil mixture can further comprises a phospholipase A, a phospholipase B, a phospholipase C, or a phospholipase D. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3 and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some embodiments the oil mixture can further comprises a phospholipase A, a phospholipase B, a phospholipase C, or a phospholipase D. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, and a lipid acyltransferase comprising at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 7. In some embodiments the oil mixture can further comprises a phospholipase A, a phospholipase B, a phospholipase C, or a phospholipase D. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some embodiments the oil mixture can further comprises a phospholipase A, a phospholipase B, a phospholipase C, or a phospholipase D. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some embodiments the oil mixture can further comprises a phospholipase A, a phospholipase B, a phospholipase C, or a phospholipase D. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the amino acid sequences of SEQ ID NO:8. In some embodiments the oil mixture can further comprises a phospholipase A, a phospholipase B, a phospholipase C, or a phospholipase D.

In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 8. In some embodiments the oil mixture can further comprises a phospholipase C. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some embodiments the oil mixture can further comprises a phospholipase C. In some aspects the enzymatic mixture does not comprise a phospholipase A.

The present disclosure provides for a crude oil mixture comprising: an oil composition, a phosphatidylinositol-specific phospholipase C comprising at least 40%, 41%, 42%, 43%, 44%, 45%, 46%, 0.47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2 and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some embodiments the oil mixture can further comprises a phospholipase C. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some embodiments the oil mixture can further comprises a phospholipase C. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4, and a lipid acyltransferase comprising at least 40%, 41%, 42%, 43%, 44%, 45%, 46%, 47%, 48%, 49%, 50%, 51%, 52%, 53%, 5.4%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 9. In some embodiments the oil mixture can further comprises a phospholipase C. In some aspects the enzymatic mixture does not comprise a phospholipase A.

The present disclosure provides for an oil composition mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO:1 and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some embodiments the oil mixture can further comprises a phospholipase C. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2 and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some embodiments the oil mixture can further comprises a phospholipase C. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some embodiments the oil mixture can further comprises a phospholipase C. In some aspects the enzymatic mixture does not comprise a phospholipase A.

The present disclosure provides for a crude oil mixture comprising: a crude oil, a phosphatidylinositol-specific phospholipase C comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 4 and a lipid acyltransferase comprising at least 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 10. In some embodiments the oil mixture can further comprises a phospholipase C. In some aspects the enzymatic mixture does not comprise a phospholipase A.

EXAMPLES

Example 1: Production of Enzymes

This example describes methods for the production and isolation of the polypeptide and enzymes provided by the present disclosure.

A recombinant expression host cell (e.g. GMO) can be generated to expresses one or more copies of the exemplary proteins of SEQ ID NO: 1-10 of the present disclosure, or a combination thereof, using the protocol described below.

Briefly, the protein encoding sequences can be cloned into an expression vector. The genes may be on one vector, multiple vectors, or as a DNA expression cassette. The genes may be inserted into the genome of the expression host cell using any method known in the art.

In applications where a vector is used, the expression vector can be transformed or transfected into a host cell. The vectors can be transformed into the host cell individually or co-transformed depending on the application.

The host cell expression strain or GMO can be constructed using any microorganism prokaryotic, eukaryotic, yeast, fungal, insect, such as for example *E. coli*, other gram-negative bacteria, gram-positive bacteria, or other proteins expression systems known in the art and as provided herein.

Depending on the number of copies of each gene and the type of promoter the host cell or GMO can be engineered to express varying ratios of each enzyme so that they are produced at a desired ratio.

The host cell is then cultured in the appropriate media and conditions that allow for growth and reproduction of the host cell.

Finally the expressed enzymes from the host cell or GMO can be isolated from the culture broth using any method known by those skilled in the art.

Lastly, the purified proteins from the broth can be stored inappropriate storage buffer and conditions in order to maintain their desired enzymatic activity.

Exemplary Protocol for *E. coli* a) A nucleic acid molecule encoding a polypeptide of the present disclosure is cloned into the NdeI-EcoRI sites of the pET24b plasmid (Novagen, USA).

b) The resulting plasmid is transformed by electroporation into the BL21A1 *E. coli* strain and colonies selected in LBA plates containing 50 mg/L Kanamycin.

c) A colony of the recombinant clone is grown on 100 ml of LB at 37° C. until cell density reaches an OD600.2.

d) The culture obtained above is transferred to a seed fermentor containing 10 liters (L) of HM medium (described below) and grown for 10 hrs at 35° C.

e) The culture is transferred to a 1000 L fermentor containing 600 L of HM medium and grown at 35° C. until glycerol exhaustion. An exponential feeding of a nutrient solution containing 80% w/v glycerol and 20 g/L $MgSO_4$ is then initiated at a rate sufficient to maintain the specific grow rate at a value of 0.35 h-1±0.05. When $OD_{600}$ reaches a value of 80, 1 mM IPTG is added and the nutrient solution is fed at a constant rate of 9±1 L/h for 10 hrs. Dissolved oxygen concentration is kept above 30% of saturation by enrichment of the air stream with pure oxygen when necessary. pH is maintained at pH 7 by the addition of $NH_4OH$.

f) At the end of the fermentation method, the broth is treated with three cycles of compression/decompression at 1000 bar in an APV homogenizers to disrupt the *E. coli* cells.

g) The resulting liquid is centrifuged until clarification to separate solid materials in a sharpless centrifuge at 5000 g.

h) $(NH_4)_2SO_4$ is added to 80% saturation to the clarified liquid, the mixture is incubated at 8° C. for 3 hrs and the centrifuged in a sharpless centrifuge at 5000 g.

i) Carefully decant the supernatant from the pellet. A brown paste pellet comprising the enzyme is then resuspended in an appropriate buffer.

Example 2: Production of Phosphatidylinositol-Specific Phospholipase (PI-PLC)

a—Production of Codon Optimized DNA Sequence of the Phosphatidylinositol-Specific Phospholipase (PI-PLC)

Phosphatidylinositol-specific phospholipase (PI-PLC) genes were selected from *Aspergillus flavus* (SEQ ID NO: 4); *Lysinibacillus sphaericus* (SEQ ID NO: 1); *Streptomyces antibioticus* (SEQ ID NO: 2); and *Enterococcus faecalis* (SEQ ID NO: 3) all of which possess conserved catalytic amino acid sequences. With the exception of *A. flavus*, all these proteins are predicted to be secreted with an N-terminal signal sequence from the Sec system as determined by Phobius software. Therefore, the predicted mature proteins were reverse translated and codon optimized for its expression in *E. coli* using a codon randomization algorithm (Menzella, 2011). The resulting sequences (SEQ ID NO:11, SEQ ID NO:12, SEQ ID NO:13 and SEQ ID NO: 14), were synthesized, and cloned in expression plasmids under the control of the BAD promoter to analyze their expression and activity.

To determine if the constructs express the corresponding PI-PLC proteins in a soluble form, the expression vectors were transformed into *E. coli* BL21(AI) strain for expression tests, and the soluble and insoluble fractions of the induced cell lysates were analyzed by SDS-PAGE.

Strains carrying the different expression plasmids were grown over-night on LB. A 100-fold dilution of the cultures was made in the same medium and incubated with shaking at 37° C. When $OD_{600}$ reached 0.5, the cultures were induced with 0.4 g/L of L-arabinose (Royal Cosun, Netherlands) for 6 hs at 30° C. Cells and culture supernatant were separated by centrifugation. The cells pellets were resuspended in buffer 10 mM HEPES pH 7.0, and 100 mM NaCl to a final $OD_{600}$ of 4 and disrupted on ice in a GEX 600 Ultrasonic Processor. The cell extracts were centrifuged, analyzed by SDS-PAGE on 12% gels, with Coomassie Brilliant blue staining and quantified by densitometry using a scanner and bovine serum albumin (BSA, Sigma) as a standard. ImageJ software was used to perform the quantitation of the scanned images (FIG. 1).

Figure 5:
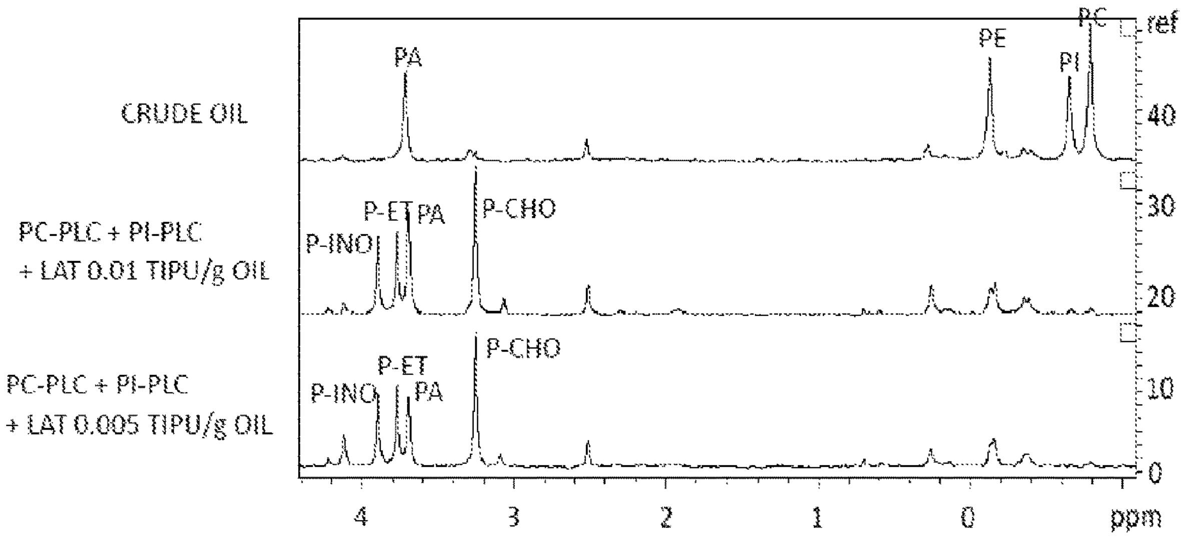

For most industrial enzymes, manufacturing cost is a critical factor and high protein expression levels are desirable. As shown in FIG. 5, PI-PLC L. *sphaericus* (SEQ ID NO: 1) expression levels are 2.46 times higher than PI-PLC *Bacillus cereus*, determined by densitometry. Since both enzymes were equally efficient at removing gums from crude oil when used similar concentration (FIG. 3), PI-PLC *L. sphaericus* provides an advantage for the development of a cost effective production process.

b—High Cell Density Protein Production Process

A seed culture of *E. coli* BL21(Al) harboring pKCN233 (pBAD::pi-PLClsphaericus) was prepared in a 1 l Erlenmeyer flask containing 0.1 l of LB medium cultivated at 37° C. and 200 rpm in a shaking incubator. Kanamycin was added at a concentration of 50 mg Li to maintain the plasmid stability.

Fed-batch fermentation was carried out in a 3 l or 20 l (New Brunswick Bio Flo 115 and Bio Flo 415, USA) containing 1 or 12 l of semi-defined HM medium (Menzella et al., 2003). The temperature, stirring and the pH were maintained at 37° C., 1200 rpm and 7 (by addition of 25% $NH_4OH$), respectively. Dissolved oxygen level was controlled at 30% of air saturation by changing the pure oxygen percentage when necessary. The feeding process was initiated when the glycerol present in the medium was exhausted. A solution containing 800 g $l^{-1}$ glycerol and 20 g $l^{-1}$ $MgSO_4.7H_2O$ was added at a variable way according to the feeding rate (F, ml $h^{-1}$) determined by equation 1 (Lee, 1996) in order to maintain the specific growth rate at 0.25 $h^{-1}$.

$$F = \frac{\mu XoVoe^{\mu t}}{SoY_{X/S}}, \qquad \text{equation 1}$$

$X_0$ is the biomass concentration (g $l^{-1}$) when the feeding is started, Vo is the initial volume (l), μ is the desired specific growth rate ($h^{-1}$), So is the glucose concentration in the feeding solution (g $l^{-1}$) and $Y_{X/S}$ is the substrate yield. Expression of PI-PLC gene was induced when the $OD_{600}$ reached 100 by adding the low cost inducer L-arabinose at a final concentration of 0.4 g Li. Afterwards, the feeding rate was maintained at 10 ml $h^{-1}$.

Figure 6:
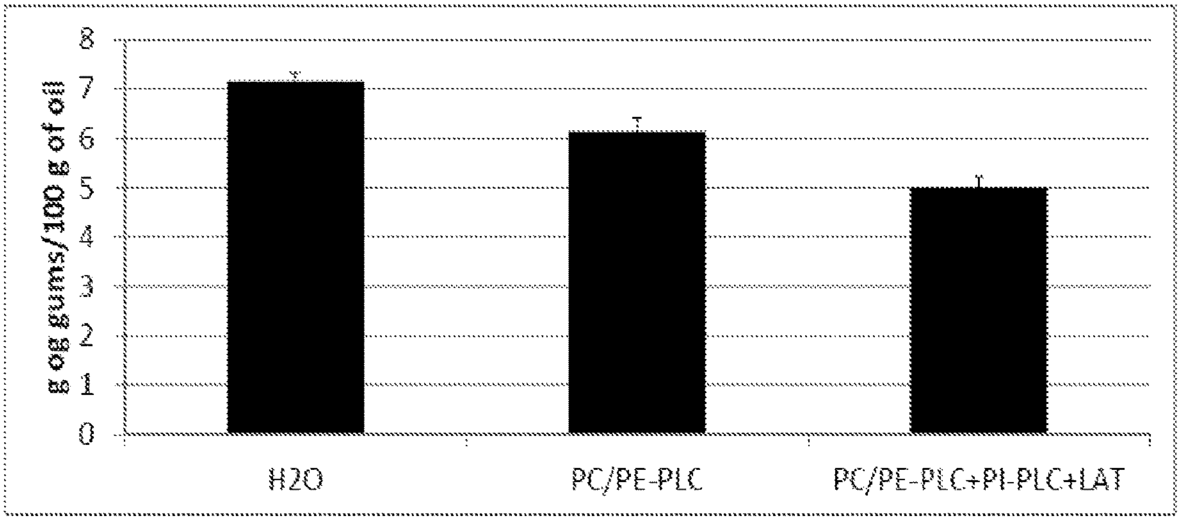
FIG. 6. Gums recovered after oil treatment. g of gum/100 g of oil was calculated for crude oil treated with (A) water (noted as $H_2O$), (B) PC/PE-PLC alone or (C) PC/PE-PLC+PI-PLC+LAT.

After the fermentation process, the cell culture was chilled and passed twice through a high pressure homogenizer at 1000 Bars (GEA Niro Soavi, Panda Plus 2000). The cell debris was separated by centrifugation at 10000 rpm for 30 minutes in a Continuous Flow Centrifuge (GEA Westfalia Separator FSD 1-06-107). The FIG. 6 shows that the expression of PI-PLC *L. sphaericus* at the induction point was approximately 3.5 g $l^{-1}$, as consequence of promoter leakage, and its production continuously increased until a maximum titer of 15 g $l^{-1}$, reached after 12 h of induction. To further reduce the manufacturing costs, the production of PI-PLC *L. sphaericus* was tested using raw glycerol derived from biodiesel plants as a carbon source, obtaining identical results. The process was scaled up using a 20 l bioreactor without losing productivity. These results are summarized in Table 2.

TABLE 2

Table 2. Fermentation parameters

| Carbon source | Glycerol pro analysis | Crude glycerol | |
|---|---|---|---|
| Fermentation volume | 12 l | 1 l | 12 l |
| $OD_{600}$ | 224 ± 13 | 225 ± 21 | 206 ± 12 |
| PI-PLC (g/l) | 14.6 ± 0.6 | 13.6 ± 0.2 | 15.3 ± 1.3 |
| Productivity (g/l/h) | 1.2 ± 0.1 | 1.1 ± 0.2 | 1.3 ± 0.2 |
| Residual glycerol (g/l) | 0.5 ± 0.1 | 0 | 2.0 ± 0.5 |
| Fermentation (h) | 29 ± 2 | 29 ± 1 | 31 ± 1 |

At the end of the fermentation run, the broth is treated with three cycles of compression/decompression at 1000 bar in an APV homogenizers to disrupt the *E. coli* cells. The resulting liquid is centrifuged until clarification to separate solid materials in a sharpless centrifuge at 5000 g. $(NH_4)_2SO_4$ is added to 80% saturation to the clarified liquid, the mixture is incubated at 8° C. for 3 hrs and centrifuged in a sharpless centrifuge at 5000 g. The supernatant is carefully decanted from the pellet. The brown paste pellet containing the enzyme is then resuspended in an appropriate buffer.

Example 3: Enzymatic Oil Degumming Using PI-PLC a—Testing for Phospholipase Activity in an Oil This example illustrates one method for testing a polypeptide for specific phospholipase C activity in an oil or oil mixture using comparative nuclear magnetic resonance analysis (NMR) and quantitation of inorganic phosphate. A reaction mixture comprising 3 grams of crude oil comprising about 15-45 μg of (SEQ ID NO: 1-4) in 90 μl of buffer comprising Sodium Citrate 50 mM pH 6.2, 1 mM $ZnCl_2$ was homogenized for about 1 min using the Ultra-Turrax T8 Homogenizer (IKA).

Next, tubes containing the reaction mixture were incubated at about 50° C. with constant agitation using a magnetic tumble stirrer such as the VP 710 magnetic tumble stirrer (VP-Scientific).

After 2 hrs incubation at 50° C. PLC activity was determined as follows:

Assay of PLC Activity in an Oil

Quantitation of Inorganic Phosphate

Phospholipase C activity was measured with a sensitive method based on the quantitation of inorganic phosphate. Polar head groups (phosphocholine, phosphoethanolamine or phosphoinositol) from hydrolyzed phospholipids in oil were recovered with aqueous extraction and hydrolyzed by alkaline phosphatase to generate inorganic phosphate.

Inorganic phosphate was determined using a modified method of Sumner (Sumner, J. B., Science 1944 196: 413).

Briefly, a 500 μl sample, containing 0.025 to 0.25 μmol of inorganic phosphate in 5% TCA was mixed with 500 μl of color reagent (4% $FeSO_4$, 1% $(NH_4)_6MoO_{24}.H_2O$, 3.2% $H_2SO_4$). Spectrophotometric readings were made at 700 nm, and the micromoles of inorganic phosphate in the sample were calculated from a standard curve.

NMR Analysis of Crude and PLC Treated Oil

Oil degumming experiments were performed using buffer as a control or enzymatic treatment for 2 h at 50° C. as indicated. Treated oil was emulsified using an Ultra-Turrax T-65 Homogenizer (IKA) for 1 min before taking 300 mg samples for further analysis. Oil samples were extracted with 900 μl of NMR solution (100 mM Tris-HCl pH 10.5, 50 mM EDTA, 2.5% sodium deoxycholate) during 1 h at 37° C. with constant agitation and the resulting aqueous phase was extracted with 600 μl hexane. Finally, 50 μl of $D_2O$ was added to the aqueous phase. $^{31}P$ NMR phospholipids profile was acquired using a Bruker 300 Ultrashield equipment. Samples of phosphatidylcholine, phosphatidylethanolamine, phosphatidic acid and phosphatidylinositol were used as standards.

Figure 3:
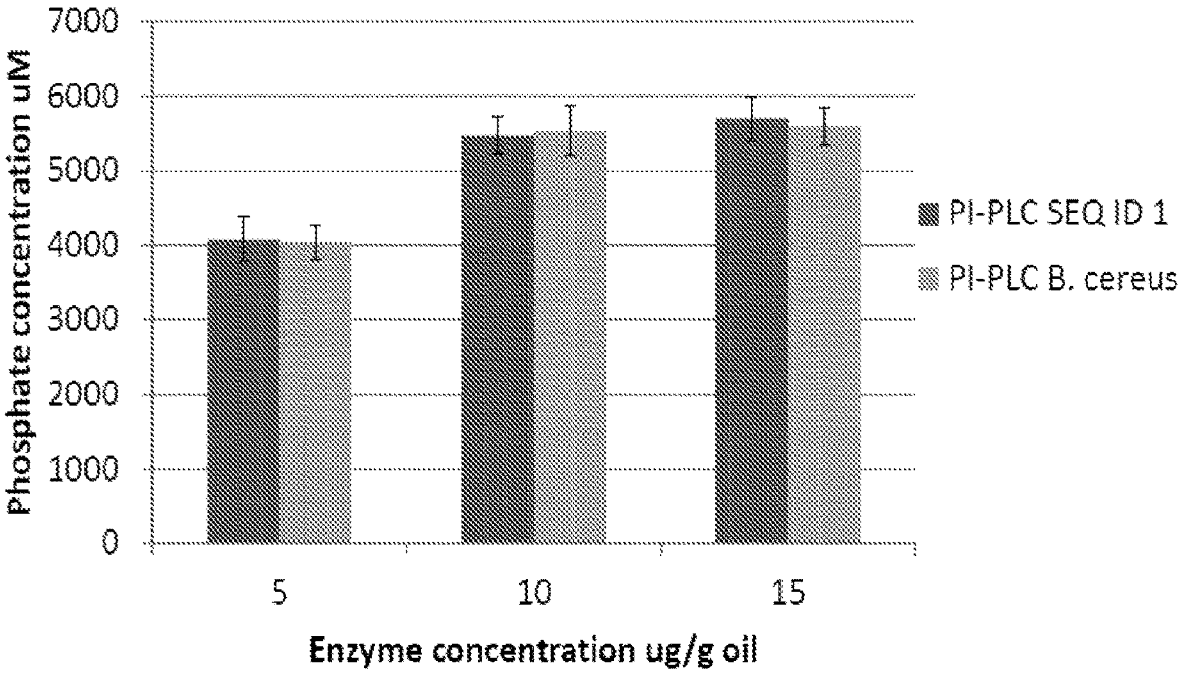
FIG. 3: shows PI-PLC activity analysis. Activity of the PI-PLC purified proteins determined in crude soybean oil as released phosphate concentration. The concentrations used of each PI-PLC were 5, 10 and 15 μg of protein per g of crude soybean oil. The results are expressed as mean and deviation standard of at least three independent experiments.

Results shown in FIGS. 3 and 4A show the capability of PI-PLC *L. sphaericus* (SEQ ID NO:1) for efficiently hydrolyzing phosphatidylinositol PI in a water-in-oil emulsion at 50° C., conditions used in industrial oil degumming. 10 μg of enzyme per gram of crude oil were sufficient to hydrolyze the PI present in crude soybean oil containing 3% of phospholipids (1200 ppm phosphate), indicating that the process of protein production, with a yield of 15 g 1-1 is suitable for the development of an industrial scale protein production. Considering a 25% margin for protein loss in the downstream process, a liter of fermentation broth would suffice for the treatment of 1 ton of crude oil (1000-1500 ppm phosphate), which makes this protein the most cost effective alternative for industrial application described so far. We also observed that proteins SEQ ID NO: 2-4 can remove near 100% of PI from an oil using 10 ug of enzyme per g of oil.

Example 4: Enzymatic Oil Degumming Using Plc Mixtures

A reaction mixture comprising 3 grams of crude oil comprising about 10 μg of (SEQ ID NO: 1) per g of oil or 5 μg of (SEQ ID NO: 5) per g of oil or a mixture of 10 μg of (SEQ ID NO: 1) per g of oil and 5 μg of (SEQ ID NO: 5) per g of oil in 90 μl of buffer comprising NaCitrate 50 mM pH 6.2, 1 mM $ZnCl_2$ was homogenized for about 1 min using the Ultra-Turrax T8 Homogenizer (IKA).

Next, tubes containing the reaction mixture were incubated at about 50° C. with constant agitation using a magnetic tumble stirrer such as the VP 710 magnetic tumble stirrer (VP-Scientific).

After 2 hrs incubation at 50° C. PLC activity was determined measuring inorganic phosphate as described above (Table 3).

We observed that the enzymatic activities of PC/PE-PLC, PI-PLC when combined in a mixture are not additive. See FIG. 4D, Tables 3 and 4.

Figure 4:
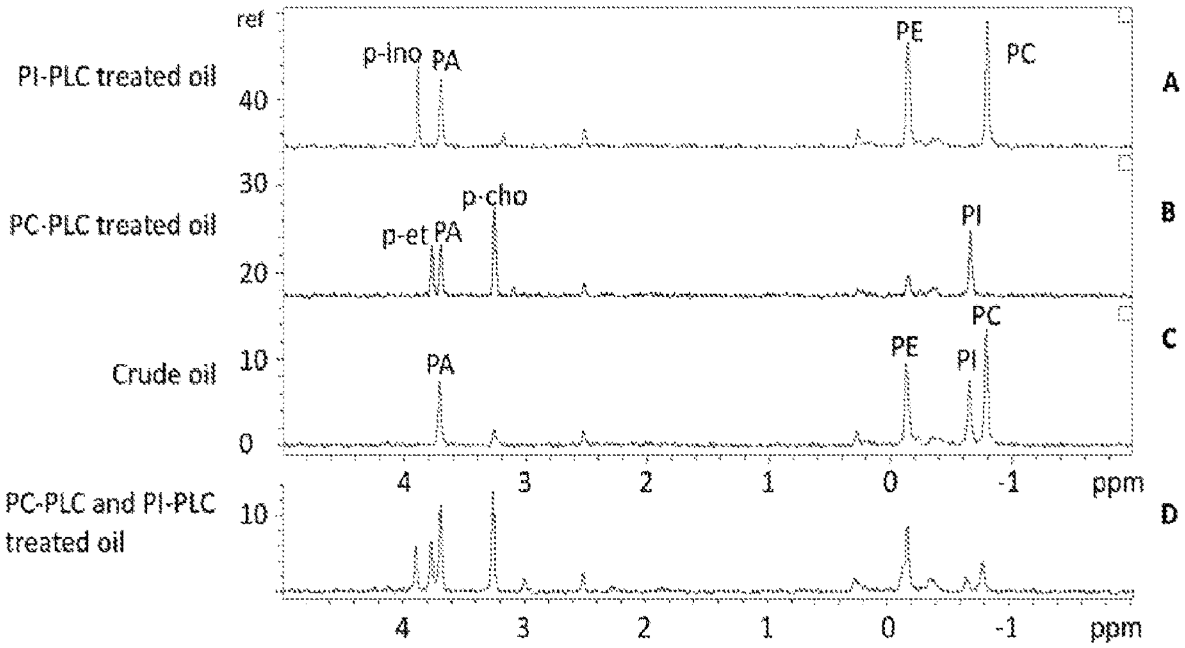
FIG. 4A-D: shows a comparative NMR analysis as one method for testing a polypeptide for specific phospholipase C hydrolysis activity in an oil. In the NMR spectra the abbreviation “PC” denotes phosphatidylcholine, “PE” denotes phosphatidylethanolamine, “PI” denotes phosphatidylinositol, “PA” denotes phosphatidic acid, “p-Cho” denotes phosphocholine, “p-Et” denotes phosphoethanolamine, and “p-Ino” denotes phosphoinositol. NMR spectra from PI-PLC (SEQ ID NO: 1) treated Oil, (B) NMR spectra from PC/PE-PLC (SEQ ID NO: 5) treated Oil and (C) an exemplary NMR spectra from Untreated crude oil (D) an exemplary NMR spectra from PC/PE-PLC+PI-PLC treated Oil FIG. 5 (A)-(C): Comparative NMR analysis of the three-enzyme for oil degumming method with low concentrations of LAT enzyme compared to an untreated crude oil. (A) shows the NMR analysis for Untreated Crude Oil (B) shows the NMR analysis for the three-enzyme mixture PC/PE-PLC+PI-PLC+LAT 0.01 TIPU/g (C) NMR analysis for PC/PE-PLC+PI-PLC+LAT 0.005 TIPU/g.

NMR analysis of phospholipids remaining in oil after enzymatic treatment shows incomplete hydrolysis of PC, PI and PE when both enzymes are combined (FIG. 4D). However, when either enzyme is used alone, using the same amount of enzymes per g of oil, complete hydrolysis of PI for PI-PLC (FIG. 4 A) or PC and PE for PC/PE-PLC (FIG. 4 B) is observed.

TABLE 3

| Enzyme Mixture | PLC Activity Units (μM phosphate) |
|---|---|
| PC/PE-PLC | 15,978 |
| PI-PLC | 6,132 |
| PC/PE-PLC + PI-PLC | 11,728 |
| negative Control | 0 |

This result shows that when both enzymes (PC/PE-PLC and PI-PLC) are added together in oil the activity is lower than the activity of PC/PE-PLC alone.

TABLE 4

| Enzyme Mixture (A) | Inactivation | PLC Activity Units (A) | Enzyme Mixture (B) | PLC Activity Units (B) | PLC Activity Units (B-A) |
|---|---|---|---|---|---|
| Control | 90° C. for 5 min | 0 | PC/PE- PLC for 2 hrs | 0 | 0 |
| PI-PLC for 0 min | 90° C. for 5 min | 276 | PC/PE- PLC for 2 hrs | 16,227 | 15,951 |
| PI-PLC for 1 hr | 90° C. for 5 min | 4,817 | PI-PLC for 2 hrs | 7,206 | 2,389 |
| PC/PE-PLC for 0 min | 90° C. for 5 min | 152 | PI-PLC for 2 hrs | 6,053 | 5,901 |
| PC/PE-PLC for 1 hr | 90° C. for 5 min | 11,114 | PI-PLC for 2 hrs | 13,584 | 2,470 |

To analyze the mixture of PC/PE-PLC and PI-PLC added sequentially and at different time points, in this example each enzyme indicated in column 1 was added to 3 g of crude soybean oil (22.5 μg of PC/PE-PLC or 30 μg of PI-PLC). At 0 min (control) or after 1 hr the oil was heated at 90° C. for 5 min to inactivate the enzyme. At this point a sample of oil was taken to determine PLC activity (column A). Next, the second enzyme was added (column 4) and after 2 hrs of incubation at 50° C. PLC activity was determined as described herein (column B). Column B-A indicates PLC activity for the second added enzyme.

These results show that PC/PE-PLC activity is reduced if oil is previously treated with PI-PLC. Similarly, PI-PLC activity is reduced if oil is previously treated with PC/PE-PLC (see Table 4).

Example 5: Two-Enzyme System with LAT as Enzymatic Stabilizer in Low Concentration for Oil Degumming This example shows a method for oil degumming using a low amount of lipid acyltransferase (LAT) as compared to other enzymatic degumming methods that are currently used.

Briefly, 3 grams of crude soybean oil containing 1200 ppm of phosphate was degummed with 10 μg of phosphatidylinositol-specific phospholipase (PI-PLC, SEQ ID NO: 1) per g of oil, 5 ug of phosphatidylcholine and phosphoethanolamine-specific phospholipase (PC/PE-PLC, SEQ ID NO: 5) per g of oil and the enzymatic stabilizer in a concentration of 0.01 TIPU of LAT (SEQ ID NO: 10) per g of oil, after 2 hrs at 50° C. the PLC activity was determined as described herein. 0.01 TIPU/g of oil is equivalent to 0.2 ug of protein (SEQ ID NO: 10) per g of oil.

This is equivalent to 50 TIPU/mg of protein,

The results in Table 5 and FIG. 5A-C show that the presence of LAT at low concentrations surprisingly improved overall PLC activity. In this example it can be observed that the highest PLC activity increase for the PC/PE-PLC/PI-PLC combination was obtained when a LAT concentration of 0.01 TIPU/g oil was used. However, the effect can be detected even with lower concentrations, such as 0.005 or 0.001 TIPU/g of oil equivalent to 0.1 μg/g oil or 0.02 μg/g of oil respectively.

TABLE 5

| Enzyme Mixture | LAT (TIP Units/g of oil) | PLC Activity Units | Increase PLC Activity Units |
|---|---|---|---|
| PI-PLC | 0 U | 6,906 | N.A. |
| PC/PE-PLC | 0 U | 14,554 | N.A. |
| PI-PLC + PC/PE-PLC | 0 U | 12,882 | N.A. |
| LAT | 0.1 U | 155 | N.A. |
| PC/PE-PLC + PLC + LAT | 0.1 U | 14,460 | 1,578 |
| PC/PE-PLC + PLC + LAT | 0.01 U | 16,228 | 3,346 |
| PC/PE-PLC + PLC + LAT | 0.002 U | 14,219 | 1,337 |
| PC/PE-PLC + PLC + LAT | 0.001 U | 13,884 | 1,002 |

Example 6: Two-Enzyme Method with LAT as Stabilizer for Oil Degumming in Crude Soybean Oil Removal of Gums from a Soybean Oil Using a Two Enzyme System with LAT as Enzymatic Stabilizer of the Present Invention Vs. Water Degumming 40 g of crude oil containing 1200 ppf of phosphate was treated with:

3% water (H2O)

3% water containing 10 μg of phosphatidylinositol-specific phospholipase (PI-PLC, SEQ ID NO: 1) per g of oil, 5 ug of phosphatidylcholine and phosphoethanolamine-specific phospholipase (PC/PE-PLC, SEQ ID NO: 5) per g of oil and 0.01 TIPU of LAT (SEQ ID NO: 10) per g of oil or, 3% water containing 5 ug of phosphatidylcholine and phosphoethanolamine-specific phospholipase (PC/PE-PLC, SEQ ID NO: 5) per g of oil The reaction mixtures were incubated at 50° C. for 2 hrs with constant mixing at 50° C.

The oil mixture was incubated at 85° C. to inactivate the enzymes and centrifuged 5 min at 5000 g. Gum and centrifuged oil was weighed and g of gum/100 g of oil was calculated. Results are shown in FIGS. 6 A-C.

The observed reduction in gums in the PC/PE-PLC+PI-PLC+LAT system resulted in a 2.14% increase of the overall oil yield compared to the control using water and 1.12% increase compared to the use of PC/PE-PLC alone.

TABLE 6

| Treatment | Phosphate (ppm) | 1,3-DAG (%) | 1,2 DAG (%) | FFA (%) | Δ1,2 DAG (%) | ΔFFA (%) |
|---|---|---|---|---|---|---|
| Water | 185 | 0.22 | 0.39 | 0.42 | — | — |
| PC/PE-PLC | 98 | 0.23 | 1.13 | 0.43 | 0.80 | 0.01 |
| PC/PE-PLC + PI-PLC + LAT | 91 | 0.21 | 1.70 | 0.42 | 1.31 | 0.00 |

Example 7—Use of Low Concentration of Lysoacyltransferase (LAT) in Oil Degumming with PC/PE-PLC and PI-PLC A reaction mixture comprising 3 grams of crude oil containing 1200 ppm of phosphate with 3% of water comprising:

(1) 0.1 TIPU of LAT (SEQ ID NO: 10) per g of oil (equivalent to 2 μg of LAT per g of oil).

(2) 10 μg of (SEQ ID NO: 1) per g of oil, 5 μg of (SEQ ID NO: 5) per g of oil and 0.01 TIPU of LAT (SEQ ID NO: 10) per g of oil (equivalent to 0.2 μg of LAT per g of oil)

(3) no enzyme

Reaction mixtures were homogenized for about 1 min using the Ultra-Turrax T8 Homogenizer (IKA).

Next, tubes containing the reaction mixture were incubated at about 50° C. with constant agitation using a magnetic tumble stirrer such as the VP 710 magnetic tumble stirrer (VP-Scientific).

After 2 hrs incubation at 50° C. PLC activity was determined as described above and remaining phospholipids analyzed by NMR.

Figure 7:
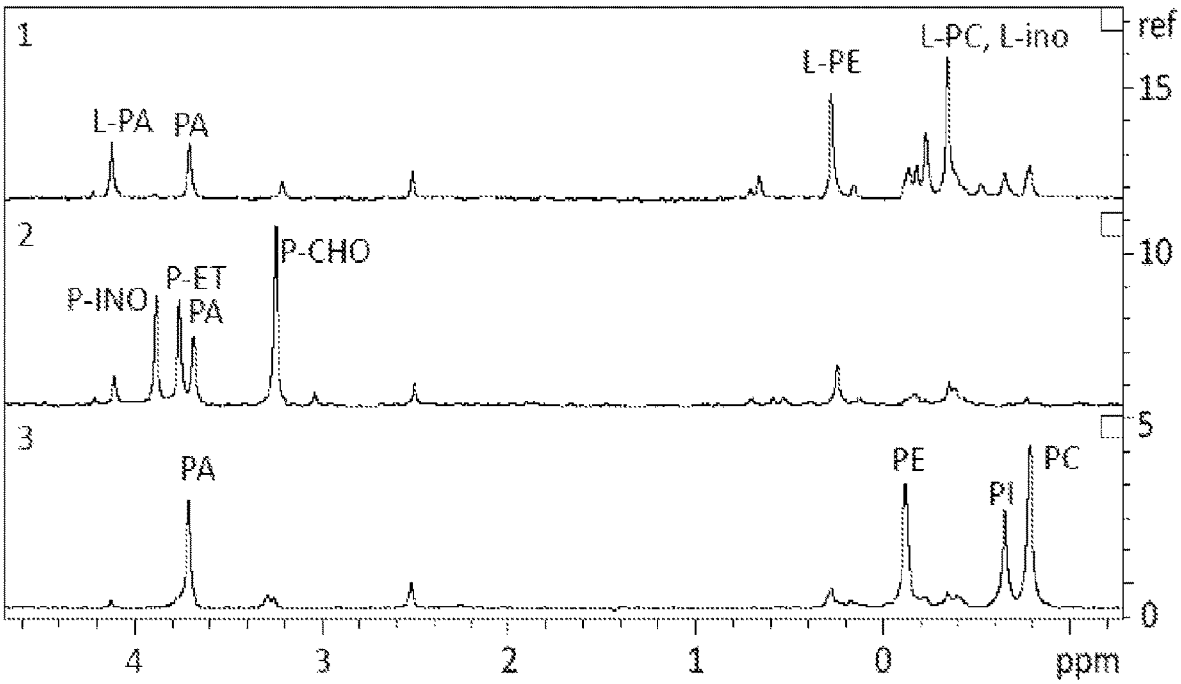
FIG. 7: NMR analysis of crude oil (3) crude oil treated with LAT 0.1 TIPU/g (1) or crude oil treated with mixture of PC/PE-PLC, PI-PLC and LAT 0.01 TIPU/g (2).

NMR spectrum of crude oil shows four peaks corresponding to phospholipids phosphatidylcholine (PC), phosphatidylethanolamine (PE), phosphatidic acid (PA) and phosphatidylinositol (PI). After treatment with lysoacyltransferase (LAT) (0.1 TIPU/g of oil) (FIG. 7-1), phospholipids PC, PE and PI were completely hydrolyzed to lysophospholipids lysophosphatidylcholine (L-PC), lysophosphatidylethanolamine (L-PE) and lysophosphatidylinositol (L-PI). Around 50% of phosphatidic acid (PA) was hydrolyzed to lysophosphatidic acid in these reaction conditions.

Figure 2:
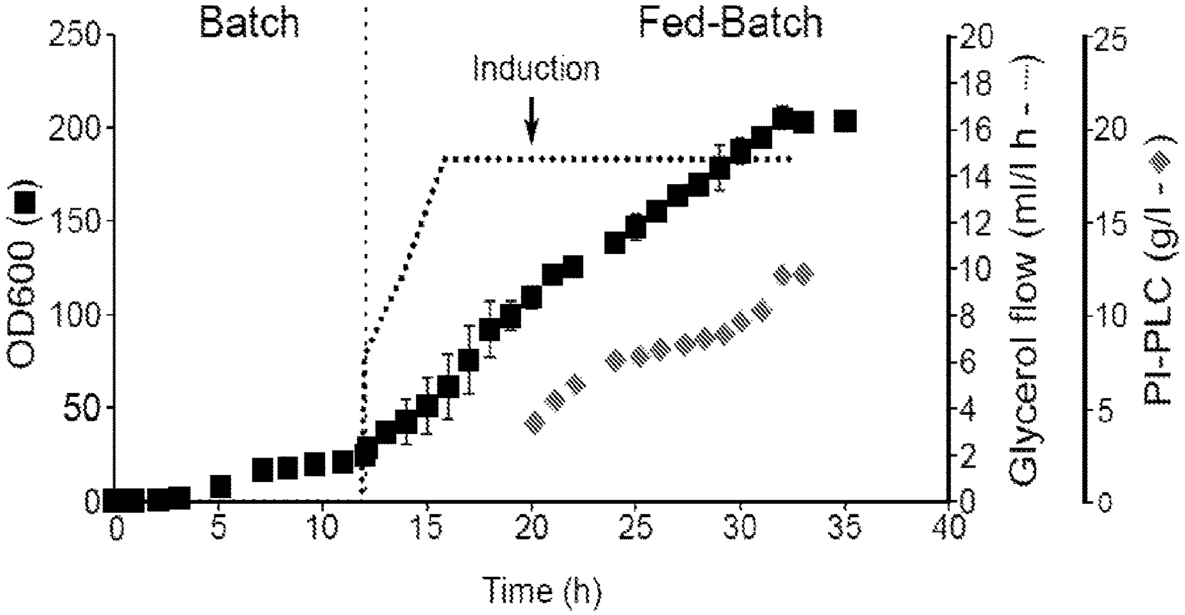
FIG. 2: shows a Fed-batch fermentation process development for PI-PLC from *L. sphaericus* production. Time course of PI-PLC total protein concentration (diamonds), biomass (black square), and glycerol flow (grey line) during fed-batch fermentation in the 2-L fermenter with a semi-defined medium. Glycerol was used as the sole carbon source and L-arabinose was used as inducer.

When crude oil was treated with the mixture of PC/PE-PLC (SEQ ID NO: 5), PI-PLC (SEQ ID NO: 1) and a low concentration (0.01 TIPU/g) of lysoacyltransferase (SEQ ID NO: 10) (FIG. 7-2) phospholipids phosphatidylcholine (PC), phosphatidylethanolamine (PE) and phosphatidylinositol (PI) were completely hydrolyzed to diacylglycerol and polar head groups phosphocholine (p-CHO), phosphoethanolamine (p-ET) and phosphoinositol (p-INO) respectively. Lysophospholipids were not detected showing that the lysoacyltransferase enzyme did not react with phospholipids under these reaction conditions.

TABLE 7

| | Lysophospholipid (mg) | PLC activity |
|---|---|---|
| Negative control | 0 | 0 |
| PC/PE-PLC | 0 | 15449 |
| PC/PE-PLC + PI-PLC | 0 | 10753 |
| PC/PE-PLC + PI-PLC | 10 | 10611 |
| PC/PE-PLC + PI-PLC | 30 | 12292 |
| PC/PE-PLC + PI-PLC | 100 | 13394 |
| PC/PE-PLC + PI-PLC + LAT | 0 | 18795 |

Crude oil was treated with the mixture of 10 μg of (SEQ ID NO: 1) per g of oil, 5 μg of (SEQ ID NO: 5) per g of oil and different added amounts (10-100 mg) of lysophospholipids or with the mixture of 10 μg of (SEQ ID NO: 1) per g of oil, 5 μg of (SEQ ID NO: 5) per g of oil and 0.01 TIPU of LAT (SEQ ID NO: 10) per g of oil PC/PE-PLC (SEQ ID NO: 5) (Table 7). The addition of lysophospholipids, the product of the catalytic activity of the LAT enzyme, did not have any effect on the mutual inhibition of PC/PE-PLC and PI-PLC. On the contrary, a low amount (0.01 TIPU/g of oil) of LAT (SEQ ID NO: 10) added to the PC/PE-PLC and PI-PLC mixture showed a significative increase in the measured PLC activity. This result suggests that the LAT protein is not exerting its effect on increasing the activity of PC/PE PLC and PI-PLC through its catalytic activity.

Example 8 Increased Protein Stability

PC/PE-PLC and PI-PLC enzymes preparations were concentrated by ultrafiltration and stored using appropriate buffers (20 mM Sodium acetate pH6, 35% glycerol). Both enzymes were stored individually or combined (mixture of PC/PE-PLC, PI-PLC and LAT). Samples were stored at 4° C. or 25° C. for up to 365 days and enzymatic activity was measured using the methods described to evaluate the stability of the enzymes. PC-PLC activity was measured using colorimetric assay with O-(4-Nitrophenylphosphoryl)choline substrate as described above (FIG. 8).

Figure 8:
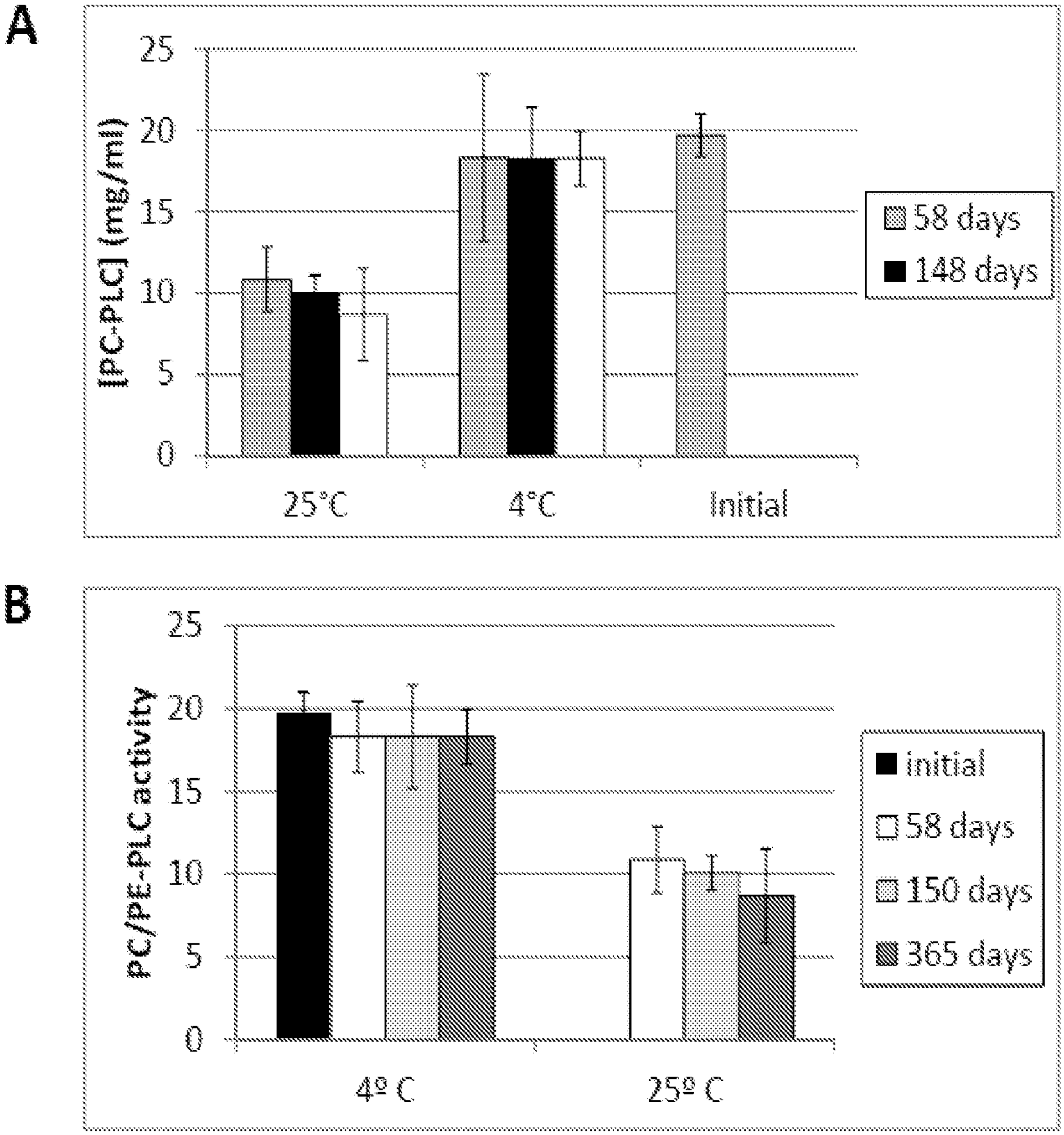
FIG. 8 PC/PE-PLC stability. PC/PE-PLC was stored alone (A) or in mixture of PC/PE-PLC+PI-PLC+LAT (B). Enzymes were stored at 4° C. or room temperature 25° C. Enzymatic activity was determined at the time of preparation (initial) or after 50, 140 and 365 days.

Results in FIG. 8 show that when stored alone (FIG. 8[a]), PC/PE-PLC enzyme preparation loses around 50% of its activity after 50 days at room temperature. However, when stored in combination with the PI-PLC and LAT (FIG. 8B) the enzyme preparation remains stable even after 365 days at room temperature. Both enzyme preparations are stable at 4° C. for at least 365 days.

Figure 9:
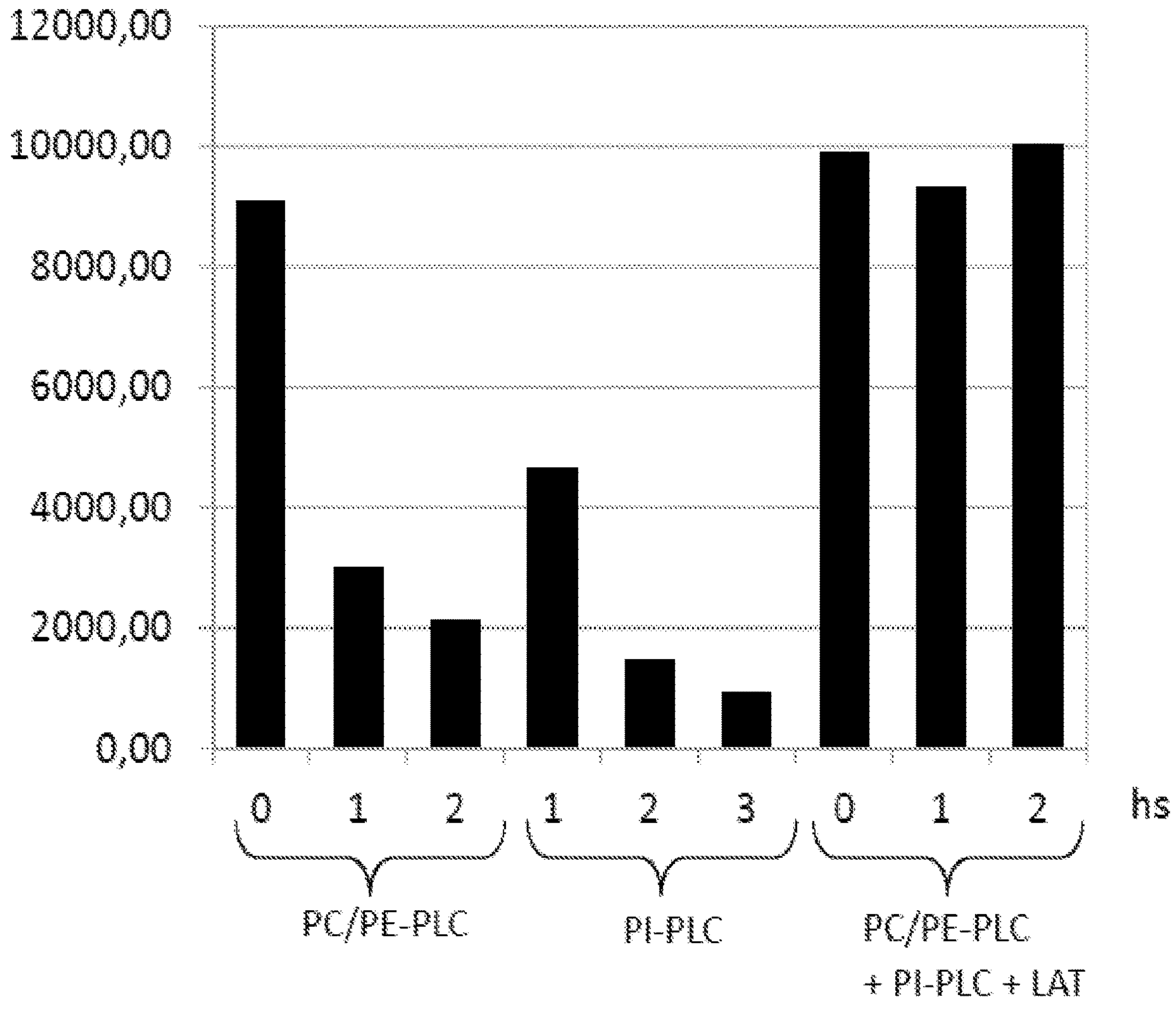
FIG. 9: shows a comparative of the enzyme stability in oil.

Results in FIG. 9 show the enzymatic stability of PLC enzymes (PC/PE-PLC and PI-PLC) in oil at 50° C. (oil degumming temperature). Enzymes PC/PE-PLC, PI-PLC or a mixture of both enzymes with the addition of LAT were incubated in 1 g of refined oil (containing no phospholipids) for the indicated time (0 as control or 1-2 h) at 50° C. This incubation was performed to evaluate the stability of the added enzyme in oil, no reaction takes place as no phospholipids are present. After this incubation, 2 g of crude oil (containing 3% phospholipids) were added and the degumming reaction took place for 2 hs at 50° C. with constant agitation. PI-PLC and PC-PLC reactions were quantified measuring inorganic phosphate as described above. Both enzymes were inactivated (less than 50% recovered activity) if incubated alone for 1 or 2 hs in oil at 50° C. However the mixture of three enzymes PC/PE-PLC, PI-PLC and LAT remained stable in the assayed condition, recovering 100% of initial activity (0 h 50° C. incubation) even after two hs of pre incubation at 50° C. This results shows that the mixture of the three enzymes (PC/PE-PLC, PI-PLC and LAT) is more stable that either each PLC alone. Taking together, these results indicate that the LAT exerts its effect at low concentrations by stabilizing the PC/PE-PLC and PI-PLC and not due to its catalytic activity. FIG. 9

Example 9: Enzymatic Treatment of Oil Composition Containing 15% Phospholipids and 15-20% Water A sample of wet gums obtained from industrial water degummed soybean oil was analyzed and found to contain 40.5% of water, 30% phospholipids and 29.5% TAG.

150 g of wet gums were mixed with 150 g of crude soybean oil giving 300 g of an oil composition containing 15% phospholipids and 20% water. This oil composition was treated with a mixture of PC/PE-PLC, PI-PLC and LAT for 6 hours. An experiment with no enzyme was used as a negative control. Enzyme concentrations used were indicated as follows:

CK1X: 5 ug/g of oil of PC/PE-PLC, 10 ug/g of oil of PI-PLC and 0.01 TIPU/g of oil of LAT.

CK2X: 10 ug/g of oil of PC/PE-PLC, 20 ug/g of oil of PI-PLC and 0.02 TIPU/g of oil of LAT.

CK4X: 20 ug/g of oil of PC/PE-PLC, 40 ug/g of oil of PI-PLC and 0.04 TIPU/g of oil of LAT.

CK6X: 30 ug/g of oil of PC/PE-PLC, 60 ug/g of oil of PI-PLC and 0.06 TIPU/g of oil of LAT.

The reaction was incubated for four or six hours (as indicated in Table 7) at 50° C. and centrifuged to separate the remaining gums from the recovered oil. 1,2-DAG and 1,3 DAG concentration was determined according to method AOCS Cd 11d-96:2009. The theoretical DAG concentration corresponding to 90% phospholipids hydrolysis is 9.45%.

Figure 10:
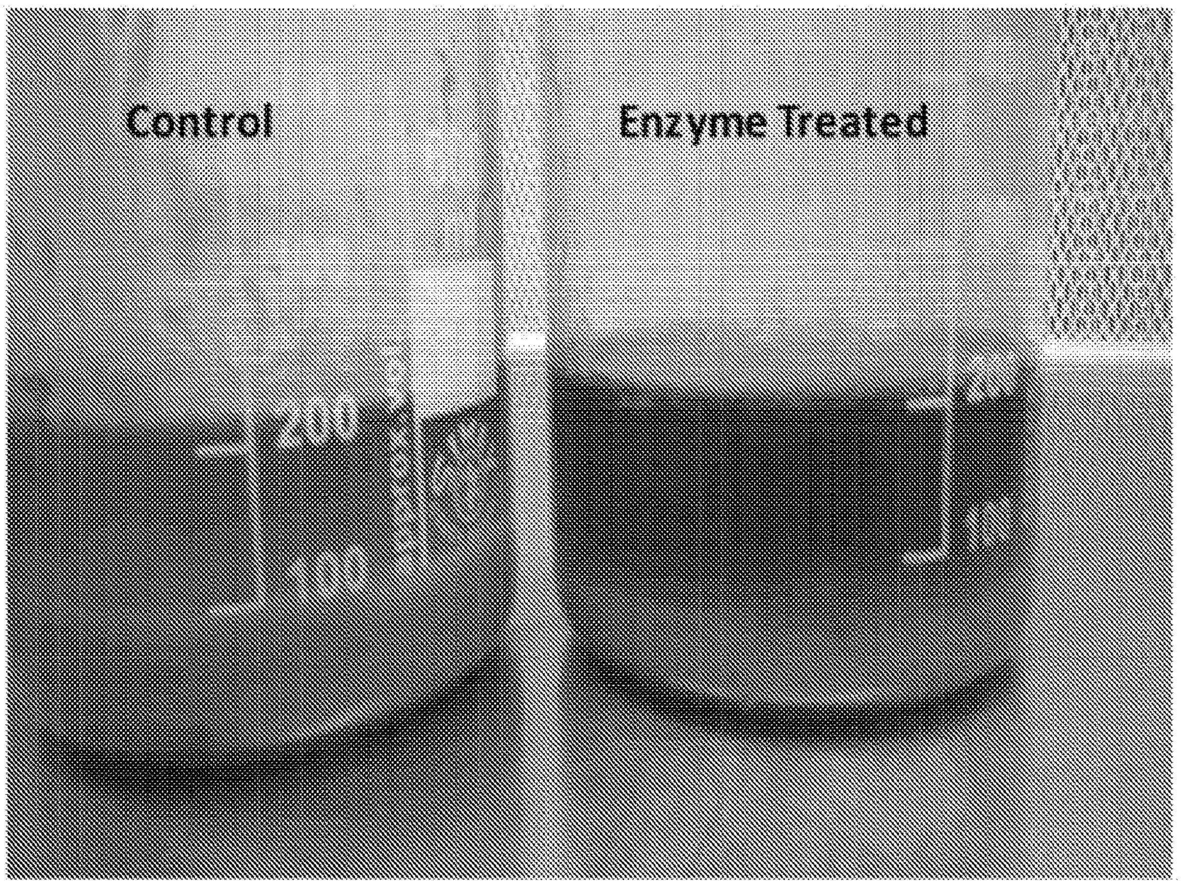
FIG. 10: Oil recovery from enzymatic treatment of oil composition containing 15% phospholipids.

Results are shown in table 8 and FIG. 10.

In order to obtain an economic benefit from an enzymatic treatment of an oil composition for oil recovery from gums, the value of the extra oil recovered in the process must be greater than the enzyme cost plus additional energy and capital costs required in the plant. Previous art teaches treatments that use extremely high enzyme concentrations, which carries costs that are far above the profitability of the process.

In the reaction number 3 (Table 8) 200 g of oil were recovered in the enzyme treated sample in contrast to 145 g of oil for the negative control (reaction number 7, Table 8). The oil gain represents 37% (calculated as g of oil recovered per 100 g of treated gums). The amount of total DAGs measured indicates hydrolysis of more than 90% of the total phospholipids present in the initial oil composition. The amount of enzyme used (30 μg/g of oil of PC/PE-PLC, 60 μgig of oil of PI-PLC and 0.06 TIPU/g of oil of LAT) is far below previous reports.

TABLE 8

Oil gain is expressed as g of oil recovered per 100 g of treated gums. 150 g of gums were incubated with 150 g of crude oil. Total recovered oil is indicated in column 4.

| reaction no | Reaction condition | % hydrolysis | Recovered oil (g) | 1,3-DAGs (%) | 1,2-DAGs (%) | Total DAG | Oil gain (%) |
|---|---|---|---|---|---|---|---|
| 1 | CK 6x, 6 hs | 98 | 197 | 2.28 | 6.62 | 8.9 | 36 |
| 2 | CK 4x, 6 hs, | 90 | 187 | 2.14 | 6.84 | 8.98 | 34 |
| 3 | CK 6x, 6 hs, | 90 | 205 | 1 | 8.88 | 9.88 | 37 |
| 4 | CK 6x, 4 hs, | 70 | 190 | 1 | 8.22 | 9.22 | 35 |
| 5 | CK 6x, 4 hs, | 70 | 200 | 1.38 | 8.62 | 10 | 35 |
| 6 | CK 2x, 6 hs | 40 | 174 | 0.84 | 5.66 | 6.5 | 27 |
| 7 | Negative control | 0 | 145 | 0.23 | 0.33 | 0.56 | — |

Example 10: Enzymatic Treatment of Oil Composition Containing 30% Phospholipids and 40% Water A sample of wet gums obtained from industrial water degummed soybean oil was analyzed and found to contain 40.5% of water, 30% phospholipids and 29.5% TAG.

300 g of wet gums were treated with a mixture of PC/PE-PLC, PI-PLC and LAT for 6 hours. An experiment with no enzyme was used as a negative control. Enzyme concentrations used was:

CK6X: 30 μgig of oil of PC/PE-PLC, 60 μgig of oil of PI-PLC and 0.06 TIPU/g of oil of LAT.

The reaction was incubated for six hours at 50° C. and centrifuged to separate the remaining gums from the recovered oil. 59.4 g of oil were recovered in the enzyme treated sample in contrast to 0 g of oil for the negative control giving 19.8% of oil gain (calculated as g of oil recovered per 100 g of treated gums). FIG. 10.

What is claimed is:

1. A process for degumming an oil composition that comprises between 1% and 40% w/w of phospholipids and 1% to 30% w/w water, wherein said method comprises: contacting said oil composition with an enzymatic mixture that comprises the polypeptides of SEQ ID NO: 1, SEQ ID NO: 5 and SEQ ID NO: 10, wherein the concentration of the polypeptide of SEQ ID NO: 10 is no greater than 0.06 TIPU/g oil.

2. The process of claim 1, wherein the enzymatic mixture hydrolyzes more than 70% (w/w) of phospholipids present in said oil composition into diacylglycerol and phosphate ester.

3. The process of claim 1, wherein said process results in increasing the degummed oil yield by at least 2% compared to a non-enzymatic oil degumming process.

4. The process of claim 1, wherein said process does not comprise the use of a protein with phospholipase A activity.

5. The process of claim 1, wherein said oil composition is an edible oil selected from the group consisting of a soybean, a rapeseed, a sunflower seed, a rice bran, a sesame, a corn, a palm, and a peanut oil.

6. The process of claim 1, wherein said oil composition is a mixture of crude oils and wet gums containing a composition of 10%-30% phospholipids, said oil composition is contacted with said enzymatic mixture for a time of at least 4 hours and more than 70% of the total phospholipids present in the initial wet gum is hydrolyzed, and the oil gain is at least 34 g of oil recovered per 100 g of treated gum.

* * * * *

SEQUENCE LISTING

<160> NUMBER OF SEQ ID NOS: 16

<210> SEQ ID NO 1
<211> LENGTH: 387
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 1

Met Ala Ala Ser Glu Arg Asp Asn Ile Asn Leu Ser Glu Trp Met Arg
1 5 10 15

Glu Ile Pro Asn Ser Asn Thr Leu Ala Glu Ile Ser Ile Pro Gly Thr
20 25 30

His Asp Ser Gly Thr Phe Arg Leu Glu Asp Pro Ile Lys Ser Val Trp
35 40 45

Ala Lys Thr Gln Glu Asn Asp Phe Arg Tyr Gln Met Asp His Gly Val
50 55 60

Arg Phe Phe Asp Ile Arg Gly Arg Val Thr Asp Asp Asn Thr Ile Val
65 70 75 80

Leu His His Gly Pro Ile Tyr Leu Tyr Val Thr Leu Gln Gln Phe Ile
85 90 95

Asn Glu Ala Lys Glu Phe Leu Lys Ser His Pro Ser Glu Thr Ile Ile
100 105 110

Met Ser Leu Lys Glu Glu Tyr Glu Ser Met Pro Gly Ala Lys Glu Ser
115 120 125

Phe Ala Lys Thr Phe Glu Asn Met Tyr Phe Gly Asp Ser Ile Phe Leu
130 135 140

Lys Thr Glu Gly Asn Ile Thr Leu Gly Asp Ser Arg Gly Lys Ile Val
145 150 155 160

Leu Leu Arg Arg Tyr Ser Gly Ser Thr Met Thr Gly Gly Phe Lys Asn
165 170 175

Phe Gly Trp Lys Asp Asn Ala Thr Phe Thr Ser Thr Thr Asn Gly Asn
180 185 190

Val Lys Ile Thr Val Gln Asp Lys Tyr Asn Val Asn Tyr Glu Glu Lys
195 200 205

Lys Ala Ala Ile Asp Ser Met Leu Lys Glu Thr Val Leu Asn Lys Asp
210 215 220

Asn Pro Asn His Ile His Ile Asn Phe Thr Ser Leu Ser Ser Gly Gly
225 230 235 240

Thr Ala Trp Ser Ser Pro Tyr Tyr Tyr Ala Ser Tyr Leu Asn Ser Ile
245 250 255

Ser Ala Ala Lys Val Arg Leu Asp His Leu Lys Asn Leu Asp Thr Lys
260 265 270

Ala Gly Trp Ile Ile Met Asp Tyr Ile Gly Asp Arg Trp Asp Pro Lys
275 280 285

Leu Tyr Glu Glu Ile Ile Arg Ala Asn Phe Arg Tyr Pro Pro Thr Asp
290 295 300

Glu Pro His Leu Phe Glu His Ile Asp Gly Glu Gly Ile Asp Phe Thr
305 310 315 320

Asn Leu Pro His Ser Lys Trp Asn Asp Gln Val Ser Ser Ile Leu Leu
325 330 335

Lys Ser Tyr Thr Glu Ile Thr Ile Tyr Glu His Ser Asn Phe Thr Gly

```
        340                 345                 350

Lys Ser Val Thr Leu Thr Asn Thr Thr Asn Ser Ala Gln Leu Phe Asn
    355                 360                 365

Leu Thr Thr Tyr Asn Phe Asn Asp Lys Met Ser Ser Tyr Thr Trp Lys
    370                 375                 380

Leu Ile Arg
385


<210> SEQ ID NO 2
<211> LENGTH: 271
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 2

Met Gly Val Arg Leu Ser Val Gln Asp Trp Met Ser Ala Leu Gly Asp
1               5                   10                  15

Ala Thr Pro Val Gln Arg Leu Thr Ile Pro Gly Thr His Asp Ser Gly
            20                  25                  30

Ala Arg Val Gly Gly Pro Trp Val Ala Cys Gln Asn Thr Pro Val Asp
        35                  40                  45

Ala Gln Leu Asn Ser Gly Ile Arg Phe Leu Asp Val Arg Cys Arg Ala
    50                  55                  60

Ile Asp Asn Val Phe Ala Ile His His Gly Ala Phe Tyr Gln Glu Leu
65                  70                  75                  80

Met Phe Gly Asp Val Leu Asn Ala Cys Arg Ala Phe Leu Arg Ala His
                85                  90                  95

Pro Ser Glu Thr Val Leu Met Arg Val Lys Gln Glu Tyr Ser Glu Val
            100                 105                 110

Gly Ala Glu Glu Phe Arg Arg Ile Phe Gly Ile Tyr Leu Asp Asp Lys
        115                 120                 125

Gly Tyr Arg Ser Leu Phe Arg Leu Asp Ala Gly Leu Pro Thr Leu Gly
    130                 135                 140

Gln Ala Arg Gly Arg Val Val Leu Leu Ala Asp Ser Asp Gly Leu Gly
145                 150                 155                 160

Gly Val Arg Tyr Ala Asp Pro Gln Leu Phe Asp Ile Gln Asp Asp Tyr
                165                 170                 175

Met Ala Glu Ala Phe Gly Lys Tyr Pro Lys Ile Glu Ala Gln Phe Arg
            180                 185                 190

Lys Ala Val Ala Gln Pro Gly Lys Leu Phe Val Asn Tyr Val Ser Thr
        195                 200                 205

Ala Ala Leu Leu Pro Pro Arg Ser Asn Ala Asp Arg Leu Asn Pro Gln
    210                 215                 220

Val Lys Arg Leu Leu Glu Gly Ser Glu Gly Ser Gly Trp Thr Gly Leu
225                 230                 235                 240

Gly Ile Val Pro Met Asp Phe Pro Asn Glu Asn Gly Leu Ala Glu Thr
                245                 250                 255

Leu Ile Arg His Asn Leu Ala Gly Gln Gly Val Arg Leu Thr Ala
            260                 265                 270


<210> SEQ ID NO 3
<211> LENGTH: 315
<212> TYPE: PRT
```

-continued

<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 3

Met Val Lys Lys Ile Phe Leu Asn Phe Leu Ile Gly Ile Gly Leu Ile
1               5                   10                  15

Ile Leu Asn Asn Phe Val Phe Ser Val Asn Glu Val Phe Ala Asp Ser
            20                  25                  30

Arg Trp Met Ser Thr Ile Arg Asp Asp Lys Pro Leu Ser Arg Val Ala
        35                  40                  45

Val Pro Gly Thr His Asp Ser Gly Thr Phe Lys Met Ser Asp Pro Ile
    50                  55                  60

Ile Ser Ala Leu Val Arg Thr Gln Glu Gln Asp Phe Arg Gln Gln Leu
65                  70                  75                  80

Glu Gln Gly Ile Arg Phe Phe Asp Ile Arg Gly Arg Ala Thr Lys Asn
                85                  90                  95

Asn Gln Ile Val Leu His His Gly Pro Lys Tyr Leu Leu Val Thr Leu
            100                 105                 110

His Gln Phe Leu Gln Glu Ala Glu Asn Phe Leu Arg Asn Asn Pro Ser
        115                 120                 125

Glu Thr Ile Ile Met Ser Leu Lys Glu Glu Tyr Pro Ala Met Glu Glu
    130                 135                 140

Val Thr Lys Ser Phe Phe Ser Ile Phe Lys Glu Ser Tyr Phe Asn Tyr
145                 150                 155                 160

Tyr Pro Phe Tyr Thr Gly Asn Ser Ser Asn Pro Lys Ile Gln Glu Thr
                165                 170                 175

Arg Gly Lys Ile Val Leu Phe Asp Arg Thr Gly Asn Ser Thr Leu Pro
            180                 185                 190

Gly Tyr Asn Lys Ile Tyr Asn Trp Glu Asp Asn Ala Thr Phe Gln Thr
        195                 200                 205

Thr Thr Asn Asn Thr Leu Pro Leu Tyr Val Gln Asp Glu Tyr Asn Ala
    210                 215                 220

Thr Tyr Asn Arg Lys Thr His Ala Ile Leu Asp Leu Leu Lys Thr Ser
225                 230                 235                 240

Ser Glu Ser Asn Glu Gly Ile Phe Leu Asn Tyr Val Ser Leu Ala Thr
                245                 250                 255

Gly Gly Thr Ala Trp Ser Ser Pro Tyr Tyr Phe Ala Ser Tyr Leu Asn
            260                 265                 270

Pro Leu Thr Gly Gly Tyr Ile Asn Glu Phe His Val Ser Asn Pro Gly
        275                 280                 285

Trp Val Val Met Asp Tyr Ser Gly Asn Arg Trp Asn Pro Asn Leu Thr
    290                 295                 300

Lys Lys Val Ile Glu Thr Asn Arg Tyr Leu Gln
305                 310                 315

<210> SEQ ID NO 4
<211> LENGTH: 337
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 4

Met Ser Ile Tyr Ser Ser Ala Asn Leu Asn Ala Trp Met Gly Glu Leu
1               5                   10                  15

Lys Asp Asp Thr Leu Leu Ser Ser Leu Ser Ile Pro Gly Thr His Asn
            20                  25                  30

Ser Pro Thr Cys His Val Ala Pro Pro Ser Val Arg Cys Gln Ala Val
        35                  40                  45

Ser Pro Arg Glu Gln Leu Glu Asn Gly Val Arg Phe Phe Asp Ile Arg
    50                  55                  60

Val Gln Pro Gln Tyr Pro Glu Asp Ala Asp Lys Asp Glu Leu Ala Leu
65                  70                  75                  80

Val His Ser Val Phe Pro Ile Ser Leu Thr Gly Ser Lys Tyr Phe Arg
                85                  90                  95

Asp Leu Met Arg Glu Val Asn Glu Phe Leu Asp Gln Asn Pro Ser Glu
            100                 105                 110

Thr Leu Ile Ile Ser Leu Lys Arg Glu Gly Pro Gly Glu His Thr Asp
        115                 120                 125

Gln Gln Leu Ser Arg Ile Leu Ser Asp His Tyr Ala Arg Pro Asp Ser
    130                 135                 140

Arg Trp Tyr Thr Asn Pro Lys Ile Pro Thr Leu Gly Glu Val Arg Gly
145                 150                 155                 160

Lys Val Val Leu Ile Arg Arg Phe Asp Ile Leu Asp His Leu Lys Asp
                165                 170                 175

Ile His Gly Gly Ala Gly Trp Gly Ile Cys Ala Ser Gly Trp Ala Asp
            180                 185                 190

Asn Cys Ser Asn Ala Thr Cys Pro Ser Gly Gln Leu Cys Ile Gln Asp
        195                 200                 205

Phe Tyr Glu Val Leu Glu Thr Glu Asn Ile Gly Glu Lys Ile Lys Tyr
    210                 215                 220

Val Gln Glu His Cys Phe Arg Ala Ala Glu Thr Cys Tyr Pro Phe Gly
225                 230                 235                 240

Val Leu Pro Asp His Glu Ala Thr Lys Ala His Pro Phe Tyr Ile Asn
                245                 250                 255

Phe Leu Ser Ala Ser Asn Phe Trp Lys Leu Gly Thr Trp Pro Glu Lys
            260                 265                 270

Ile Ala Gly Lys Leu Asn Pro Ala Ala Val Asp Tyr Leu Cys Arg Lys
        275                 280                 285

His Gly Glu Lys Asp Asp Cys Asp Trp Ser Thr Gly Ile Leu Val Thr
    290                 295                 300

Asp Trp Val Gly Leu Asp Gly Asp Trp Asp Leu Val Arg Cys Ile Val
305                 310                 315                 320

Gly Met Asn Ala Arg Leu Lys Leu Arg Gln Asp Arg His Glu Gly Asp
                325                 330                 335

Asn

<210> SEQ ID NO 5
<211> LENGTH: 245
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 5

```
Trp Ser Ala Glu Asp Lys His Lys Glu Gly Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Leu Leu Asn Glu Trp Arg Thr Glu Leu Glu
        35                  40                  45

Asn Gly Ile Tyr Ala Ala Asp Tyr Glu Asn Pro Tyr Tyr Asp Asn Ser
    50                  55                  60

Thr His Ala Ser His Phe Tyr Asp Pro Asp Asn Gly Lys Thr Tyr Ile
65                  70                  75                  80

Pro Tyr Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Asn Phe Thr Asn Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Asp Trp Ile
                165                 170                 175

His Gly Ala Ala Val Val Ala Lys Gln Asp Tyr Ala Gly Ile Val Asn
            180                 185                 190

Asp Asn Thr Lys Asp Trp Phe Val Arg Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asn Arg
                245
```

<210> SEQ ID NO 6
<211> LENGTH: 278
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 6

```
Met Ala Lys Phe Met Asp Lys Thr His Pro Ile Ser Glu Leu Tyr Val
1               5                   10                  15

Phe Gly Asp Ser Leu Ser Asp Thr Gly Met Val Phe Arg Ala Thr Gly
            20                  25                  30

Gly Met Tyr Pro Pro Asn Pro Thr Tyr Phe Gln Gly Arg Tyr Ser Asn
        35                  40                  45

Gly Arg Val Trp Ile Glu Tyr Leu Ala Glu Ser Leu His Leu Ser Pro
    50                  55                  60

Lys Gln Thr His Asn Phe Ala Tyr Gly Gly Ala Thr Thr Ala Asn Val
65                  70                  75                  80

Gly Asn Ser Tyr Val Pro Ser Leu Leu Asn Gln Val Gln Ser Phe Thr
```

```
                85                  90                  95

Gln Thr His Gln Gln Thr Asn Pro Asp Ala Leu Tyr Val Leu Trp Ala
            100                 105                 110

Gly Ala Asn Asp Tyr Leu Gln Gly Val Ser Ser Ala Ser Ile Pro Val
        115                 120                 125

Lys Asn Val Thr Thr Ala Ile Asn Ser Leu Thr Asp Val Gly Ala Lys
    130                 135                 140

Lys Ile Leu Val Gly Asn Leu Pro Asp Leu Gly Gln Leu Pro Ala Thr
145                 150                 155                 160

Arg Asn Ser Thr Asn Ser Val Ser Leu Ser Ala Leu Thr Gln Ala His
                165                 170                 175

Asn Gln Gly Leu Arg Arg Ser Leu Lys Val Leu Gly Gln Gln His Ser
            180                 185                 190

Asp Leu Glu Ile Val Gln Leu Asp Ala Asn Ala Leu Tyr Arg His Ala
        195                 200                 205

Ile Ala Lys Pro Ala Ala Phe Asn Phe Thr Asn Val Ile Ser Pro Cys
    210                 215                 220

Leu Ser Gly Asp Arg Thr Cys Ser Asn Pro Asp Gln Phe Leu Phe Trp
225                 230                 235                 240

Asp Gly Ile His Pro Thr Ala Ala Ala His Arg Ile Ile Ala Glu Thr
                245                 250                 255

Ala Phe Ser Thr Ile Gln Glu Ala Gly Met Thr Asn Pro Leu Leu Ser
            260                 265                 270

Leu Ser Leu Glu Tyr Asn
        275


<210> SEQ ID NO 7
<211> LENGTH: 282
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 7

Met Ala Pro Ile Gln Ser Ser Asn Met Ile Gln Ile Ser His Gln Ile
1               5                   10                  15

Asn Arg Leu Tyr Val Phe Gly Asp Ser Leu Ser Asp Val Gly Asn Val
            20                  25                  30

Tyr His Ala Ser Gly Lys Ile Tyr Pro Pro Asn Pro Pro Tyr Phe Glu
        35                  40                  45

Gly Arg Tyr Cys Asn Gly Leu Val Trp Val Glu Tyr Leu Ser Ala Lys
    50                  55                  60

Leu Ala Leu Thr Pro Glu Gln Asn Ala Asn Phe Ala Tyr Gly Gly Ala
65                  70                  75                  80

Thr Thr Gly Asn Gly Ser Val Asn Gly Val Pro Gly Leu Leu Ala Gln
                85                  90                  95

Val Gln Ala Phe Thr Lys Val His Gln Glu Val Asn Ser Asn Ala Leu
            100                 105                 110

Tyr Val Leu Trp Ala Gly Ala Asn Asp Tyr Leu Tyr Gly Gly Ala Asn
        115                 120                 125

Pro Thr Leu Thr Leu Gly Asn Ile Ser Lys Ala Val Glu Ser Leu Leu
    130                 135                 140

Lys Met Gly Ala Lys Lys Ile Met Val Val Asn Leu Pro Asp Leu Gly
```

```
145                 150                 155                 160

Lys Leu Pro Ala Thr Arg Thr Ser Ala Asn Ser Asn Thr Ile Ser Ser
                165                 170                 175

Phe Ala Ile Ala His Asn Gln Ser Leu Ala Lys Ser Val Glu Glu Leu
            180                 185                 190

Lys Gln Lys Leu Gly Ser Asp Thr Gln Ile Ala Ile Leu Asp Ile Tyr
        195                 200                 205

Ser Leu Tyr Gln Glu Ala Thr Lys His Pro Gly Met Phe Gly Leu Thr
    210                 215                 220

Asn Val Thr Asn Ala Cys Ser Asn Asn Leu Ala Ile Cys Asp Arg Pro
225                 230                 235                 240

Asp Lys Tyr Leu Phe Trp Asp Gly Ile His Pro Thr Thr Val Ala His
                245                 250                 255

Arg Ile Ile Ala Glu Ala Ala Leu Lys Val Ile Lys Thr Glu Phe Ser
            260                 265                 270

Phe Ser Ala Thr Ser Pro Gln Pro Leu Ser
        275                 280


<210> SEQ ID NO 8
<211> LENGTH: 279
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 8

Met Ala Pro Thr Thr Ser Ile Thr Asn Cys His Thr Ser Ile Asn Glu
1               5                   10                  15

Leu Tyr Val Phe Gly Asp Ser Leu Ser Asp Ile Gly Asn Val Phe Asn
            20                  25                  30

Ala Thr Glu Gly Phe His Pro Ser Ser Pro Pro Tyr Phe Gln Gly Arg
        35                  40                  45

Phe Ser Asn Gly Leu Val Trp Val Glu Tyr Leu Ala Ser Gly Leu Ala
    50                  55                  60

Leu Thr Pro Lys Gln Asn Thr Asn Phe Ala Tyr Gly Gly Ala Thr Thr
65                  70                  75                  80

Gly Ser Gly Asn Ile Asn Arg Ile Pro Asp Leu Leu Thr Gln Val Asp
                85                  90                  95

Gly Phe Ile Lys Ile His Gln Gln Val Asp Arg Asn Ala Leu Tyr Ile
            100                 105                 110

Leu Trp Ala Gly Ala Asn Asp Tyr Leu His Ser Met Ser Asn Pro Ser
        115                 120                 125

Val Ser Ile Ser Asn Ile Ser Gln Ala Ile Gln Ser Leu Ala Lys Val
    130                 135                 140

Gly Ala Lys Lys Ile Leu Val Ala Asn Leu Pro Asp Leu Gly Asn Ile
145                 150                 155                 160

Pro Ala Thr Arg Asn Ser Pro Tyr Ser Ser Ile Leu Ser Ser Ala Thr
                165                 170                 175

Ile Ala His Asn Leu Ser Leu Val Lys Ser Leu Asp Ile Leu Lys Gln
            180                 185                 190

Lys Leu Gly His Asp Ser Gln Met Ile Met Leu Asp Val His Ser Leu
        195                 200                 205

Tyr Lys Glu Ala Ile Ala Asn Pro Thr Lys Phe Gly Phe Ile Asn Val
```

```
    210                 215                 220

Thr Glu Ala Cys Leu Asn Lys Leu Ala Thr Cys Gly Asn Pro Asp Lys
225                 230                 235                 240

Phe Leu Phe Trp Asp Gly Ile His Pro Thr Thr Ala Ala His Gln Ile
                245                 250                 255

Leu Ala Lys Ala Ala Leu Lys Glu Leu Lys Thr Thr Tyr Ser Phe Pro
            260                 265                 270

Pro Leu Pro Glu Leu Leu Gln
        275


<210> SEQ ID NO 9
<211> LENGTH: 328
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 9

Met Ala Glu Gly Arg Gln Pro Phe Ser Arg Val Val Met Phe Gly Asp
1               5                   10                  15

Ser Leu Ser Asp Thr Gly Lys Met Tyr Lys Lys Met Arg Gly Tyr Leu
            20                  25                  30

Pro Ser Ser Pro Pro Tyr Phe Asn Gly Arg Phe Ser Asn Gly Pro Val
        35                  40                  45

Trp Leu Glu Gln Leu Gly Asp Glu Arg Phe Pro Gly Leu Val Val Ala
    50                  55                  60

Asn Glu Ala Glu Gly Gly Ala Thr Ala Val Ala Tyr Asn His Leu Gly
65                  70                  75                  80

Ala Leu Asn Gly Trp Leu Gly Phe Trp Ser Trp Asp Pro Lys Tyr Gln
                85                  90                  95

Val Ile Asn Asn Leu Asp Tyr Glu Ile Asp Gln Phe Leu Lys Lys Asp
            100                 105                 110

Lys Phe Arg Pro Asp Asp Leu Val Val Ile Trp Val Gly Ala Asn Asp
        115                 120                 125

Tyr Leu Ala Tyr Gly Trp Asn Thr Glu Arg Asp Ala Asp Arg Val Ile
    130                 135                 140

Asp Thr Ile Arg Leu Ala Ser Asn Arg Leu Val Leu Asn Gly Ala Gln
145                 150                 155                 160

Gln Ile Leu Leu Phe Asn Ile Pro Asp Leu Gly Gln Thr Pro Ser Ala
                165                 170                 175

Arg Ser Met Lys Val Val Glu Lys Val Arg His Val Ala Ser Tyr His
            180                 185                 190

Asn Gln Lys Leu Gln Asn Leu Thr Arg Glu Leu Ala Pro Leu Gly Ile
        195                 200                 205

Val Lys Leu Phe Glu Val Asp Lys Gln Phe Asp Glu Met Met Arg Asp
    210                 215                 220

Pro Gln Leu Phe Gly Leu Ser Asp Thr Glu His Ala Cys Tyr Gly Gly
225                 230                 235                 240

Gly Tyr Thr Trp Lys Pro Phe Ser Gly Ser Ala Ala Glu Val Ala Ala
                245                 250                 255

Thr Pro Ala Leu Ser Val Ser Glu Arg Val Ala Ile Ala Gly Asn Pro
            260                 265                 270

Ile Leu Ala Gln Ala Val Val Ser Gly Gln Ala Lys Gly Arg Ala Ala
```

```
        275                 280                 285

Thr Leu Asn Cys Asp Glu His Met Phe Trp Asp Gln Val His Pro Thr
    290                 295                 300

Arg Thr Val His Lys Val Leu Ser Gln Arg Val Ala Asp Phe Ile Asp
305                 310                 315                 320

Gln His Tyr Glu Phe Val Arg His
                325


<210> SEQ ID NO 10
<211> LENGTH: 337
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<223> OTHER INFORMATION: Synthesized

<400> SEQUENCE: 10

Met Met Lys Lys Trp Leu Val Cys Leu Leu Gly Leu Leu Ala Leu Thr
1               5                   10                  15

Ala Gln Ala Val Glu Arg Pro Ser Phe Ser Arg Ile Val Met Phe Gly
            20                  25                  30

Asp Ser Leu Ser Asp Thr Gly Lys Met Tyr Lys Lys Met Lys Gly Tyr
        35                  40                  45

Leu Pro Ser Ser Pro Pro Tyr Tyr Glu Gly Arg Phe Ser Asn Gly Pro
    50                  55                  60

Val Trp Leu Glu Arg Leu Arg Asp Glu His Phe Pro Gly Leu Gln Leu
65                  70                  75                  80

Ala Asn Glu Ala Glu Gly Gly Ala Thr Ala Val Ala Tyr Asn Lys Leu
                85                  90                  95

Gly Trp Leu Asn Phe Trp Ala Trp Asp Pro Lys Tyr Gln Val Ile Asn
            100                 105                 110

Asn Leu Asp Tyr Glu Ile Asp Gln Phe Leu Ala Lys Asp Ser Leu Arg
        115                 120                 125

Pro Asp Asp Leu Val Val Ile Trp Val Gly Ala Asn Asp Tyr Leu Ala
    130                 135                 140

Tyr Gly Trp Asn Gln Glu Lys Asp Ala Asp Arg Val Ile Glu Thr Ile
145                 150                 155                 160

Arg Leu Ala Ser Asn Arg Leu Val Leu Asn Gly Ala Gln Gln Ile Leu
                165                 170                 175

Leu Phe Asn Ile Pro Asp Leu Gly Arg Thr Pro Ser Ala Asn Ser Met
            180                 185                 190

Lys Val Val Asp Gln Val Arg His Val Ala Ser Tyr His Asn Gln Arg
        195                 200                 205

Leu Leu Asn Leu Ser Arg Glu Leu Ala Pro Leu Gly Ile Val Lys Met
    210                 215                 220

Phe Glu Val Asp Lys Gln Phe Asp Glu Met Val Gly Asp Pro Gln Lys
225                 230                 235                 240

Phe Gly Leu Ser Asp Ile Glu His Ala Cys Tyr Gly Gly Gly Tyr Leu
                245                 250                 255

Trp Lys Pro Phe Ser Asp Ala Ser Glu Ala Pro Ala Leu Ser Val Pro
            260                 265                 270

Glu Arg Leu Ala Val Ala Gly Asn Pro Ile Leu Ala Gln Ala Val Val
        275                 280                 285

Ser Pro Gln Ala Ala Arg Ser Ala Ala Ala Arg Asn Cys Asp Glu His
```

-continued

```
    290                 295                 300

Met Phe Trp Asp Gln Val His Pro Thr Ala Thr Val His Lys Ala Met
305                 310                 315                 320

Gly Glu Arg Val Ala Ala Phe Ile Glu Gln His Tyr Glu Phe Ile Arg
                325                 330                 335

Arg


<210> SEQ ID NO 11
<211> LENGTH: 1164
<212> TYPE: DNA
<213> ORGANISM: Escherichia coli

<400> SEQUENCE: 11

atggcggcgt cagaaagaga caacattaac ttgagcgagt ggatgagaga aattcctaac      60

agcaacacat tggcagaaat cagcattccg ggaacacatg attcaggaac gtttagactg     120

gaagacccta ttaaaagcgt gtgggcaaag acccaggaaa acgatttccg ttatcaaatg     180

gaccacggcg tcagattttt cgatatccgc ggacgtgtca ccgatgacaa cactattgtt     240

ctgcatcacg gtccaatcta cttgtacgtg acactgcaac aattcatcaa cgaagcgaag     300

gagttcttga agtctcatcc ttccgaaacg attatcatga gtctgaaaga agagtatgag     360

tctatgccag gcgctaaaga atcctttgcc aagactttcg agaacatgta ctttggagat     420

tccattttct tgaaaaccga aggtaatatc actctgggtg actcacgtgg caagattgtc     480

ctgttgcgta gatattccgg ctcaaccatg actggtggct ttaaaaactt cggatggaag     540

gataatgcta catttacgtc caccactaac ggtaatgtta aaattaccgt gcaggacaag     600

tacaacgtta actacgaaga gaaaaaggct gccatcgatt caatgttgaa agaaactgtg     660

ctgaacaagg acaacccaaa tcatattcac atcaatttca cctctctgtc ttctggtggt     720

acggcatggt caagcccgta ttactatgcg tcttacctga acagcattag tgcagcgaaa     780

gttcgcctgg atcacttgaa aaatctggac acaaaggctg gttggattat catggattac     840

atcggcgatc gttgggaccc aaagctgtat gaagagatta tcagagccaa ctttcgctac     900

ccaccgaccg atgaaccgca tttgtttgag cacattgatg gcgaaggaat cgacttcact     960

aacctgcctc atagtaaatg gaatgatcaa gtcagttcta ttctgttgaa gtcttacaca    1020

gagatcacga tctacgaaca ctcaaacttc actggaaaga gcgttacctt gactaacaca    1080

accaactctg cccaactgtt caacctgacc acctacaact tcaatgataa aatgtcctcc    1140

tacacttgga aactgattag ataa                                           1164


<210> SEQ ID NO 12
<211> LENGTH: 816
<212> TYPE: DNA
<213> ORGANISM: Escherichia coli

<400> SEQUENCE: 12

atgggagtta gactgtccgt tcaagactgg atgagcgcat tgggcgacgc aacccctgtt      60

caaagactga cgattccggg cacgcacgac tccggtgcac gtgttggtgg accatgggtg     120

gcgtgtcaga acactcctgt tgatgctcaa ctgaatagcg gcattagatt tttggatgtc     180

cgctgccgtg caattgacaa cgttttcgct atccatcacg gtgcctttta tcaggaactg     240

atgttcggcg atgttttgaa tgcatgtcgt gcgtttctgc gtgctcatcc gagtgagaca     300

gtgttgatga gagtcaaaca agaatactct gaagtgggtg ccgaagagtt tcgtagaatt     360

ttcggcatct atctggatga caagggatac cgctcactgt tccgtttgga tgccggcctg     420
```

```
cctacgttgg gacaggcaag aggtcgcgtt gtgctgttgg cggattctga cggactggga    480

ggtgtccgct atgcagatcc acagttgttt gacattcaag atgactatat ggcagaagcg    540

tttggaaaat acccaaagat cgaggcgcag ttccgtaaag ctgtggccca accgggaaag    600

ctgttcgtca actacgtttc aaccgctgcc ctgttgccac cgagaagcaa cgccgatcgc    660

ctgaatcctc aagtgaaacg tctgttggaa ggttctgagg gctccggatg gactggtttg    720

ggcatcgtcc ctatggactt tccaaacgaa aatggcttgg cagaaacatt gattagacat    780

aacttggcag gacagggagt gagattgaca gcataa                              816


<210> SEQ ID NO 13
<211> LENGTH: 948
<212> TYPE: DNA
<213> ORGANISM: Escherichia coli

<400> SEQUENCE: 13

atggtcaaga agattttcct gaacttcctg attggtatcg gactgattat cctgaataac     60

tttgtgttta gcgtgaatga ggtgtttgct gatagccgct ggatgagtac tattcgtgat    120

gacaaaccac tgagtcgcgt cgctgttccg ggcacgcatg attctggaac cttcaagatg    180

tctgacccga ttatctccgc cctggtgcgt acccaggaac aagattttcg ccagcaattg    240

gagcagggta ttcgtttctt tgacatccgt ggtagagcta ctaaaaacaa tcaaatcgtg    300

ctgcatcacg gtcctaagta tctgttggtc acactgcacc agttcttgca agaagcagag    360

aattttctga gaaacaatcc atcagaaacg attatcatga gcttgaaaga agagtacccg    420

gcgatggaag aggtcaccaa atccttttc tcaatcttca aggaatctta cttcaactac    480

taccctttt acactggcaa ctcttccaat ccaaaaattc aggagacacg tggaaagatc    540

gttctgttcg atagaactgg taactccaca ttgcctggct acaacaaaat ttacaactgg    600

gaagacaacg ctacgtttca gaccactaca aacaataccc tgccattgta tgttcaagat    660

gagtataatg caacttacaa ccgtaaaaca catgcgattc tggacctgtt gaagacctca    720

agcgaatcca atgagggtat ctttctgaac tacgtttcat tggctacggg tggcaccgcc    780

tggagttctc cgtattactt cgcctcttat ctgaaccctt tgactggagg ttacattaat    840

gaatttcacg tgagcaaccc aggctgggtt gtgatggatt atagtggcaa cagatggaac    900

cctaacctga caaagaaagt gattgagact aatagatacc tgcaataa                 948


<210> SEQ ID NO 14
<211> LENGTH: 1014
<212> TYPE: DNA
<213> ORGANISM: Escherichia coli

<400> SEQUENCE: 14

atgtctattt attcctccgc aaacctgaac gcttggatgg gcgagttgaa agacgacaca     60

ctgctgtcct cattgagtat ccctggcacc cataactcac caacatgtca cgttgcacca    120

ccatctgtga gatgccaggc agtctccccg cgtgaacaac tggagaatgg tgttcgtttc    180

tttgatatta gagtgcagcc tcaatatcca gaagatgctg acaaagatga gctggccttg    240

gtccattctg tttttccgat ctcactgacc ggcagcaagt acttccgcga tctgatgcgt    300

gaagtgaacg agtttttgga ccagaatccg tccgaaacac tgattatctc attgaaaaga    360

gaaggacctg gagagcatac ggatcagcaa ctgagtcgca ttttgtctga tcactatgcc    420

agacctgact cacgctggta cacaaacccg aaaatcccta cgctgggaga agttcgcgga    480
```

-continued

```
aaggttgtgt tgattcgtag attcgatatc ctggaccatt tgaaagatat tcacggtggc    540

gcaggctggg gaatctgtgc aagcggatgg gcggacaact gtagcaatgc tacctgccct    600

agtggtcagc tgtgcattca agatttttat gaggtcttgg aaactgagaa cattggcgaa    660

aagatcaagt acgttcaaga gcattgtttt agagctgccg aaacctgcta cccattcgga    720

gttctgccgg accatgaagc tactaaagcc cacccatttt atattaactt cctgtctgct    780

tccaatttct ggaagttggg cacctggcct gagaaaatcg ccggaaagct gaatccagca    840

gcggtggatt acttgtgtcg taaacacggt gaaaaggatg actgcgattg gtccaccggc    900

attctggtga ctgactgggt cggtctggac ggcgattggg acttggtcag atgcattgtt    960

ggtatgaacg caagactgaa gttgagacag gatagacacg aaggagataa ttaa         1014
```

<210> SEQ ID NO 15
<211> LENGTH: 1011
<212> TYPE: DNA
<213> ORGANISM: Escherichia coli

<400> SEQUENCE: 15

```
atgaaaaaat ggcttgtttg tttattgggg ttactggcgc tgaccgctca ggcggtggag     60

cgcccgagct tttcccggat cgtgatgttt ggtgacagcc tctcggacac cggcaagatg    120

tacaagaaga tgaaggggta tctcccctcc agccctccct attacgaggg gcgtttcagc    180

aatggcccgg tctggttgga acggttgcga gacgaacact tccccgggct tcagctggct    240

aacgaggctg aaggtggggc gacggcggtg gcctacaaca agctgggctg gctcaacttc    300

tgggcctggg atcccaagta tcaggtgatc aacaacctcg actacgagat cgatcagttc    360

ctggcgaagg acagcttgcg tcccgacgat ctggtggtga tctgggtggg ggccaacgac    420

tatctggcct atggctggaa tcaggagaaa gatgccgatc gggtgatcga gaccattcgc    480

ctggcatcca accgactggt gctcaacggg gcgcagcaga tcctgctgtt caacatcccg    540

gatctgggca gaactccatc cgccaacagc atgaaggtag tggatcaggt gcgccacgta    600

gccagctatc acaaccagcg gctgctcaat ctctcgcgcg aactggcccc ccttggcatc    660

gtcaagatgt tcgaagtgga caagcagttt gacgagatgg ttggtgatcc ccagaaattc    720

gggctgagcg acatcgagca cgcctgctat ggcggcgggt atctgtggaa gcccttctcc    780

gatgcgagcg aggcgccagc cttgagcgtc ccagagcgtc tggcagtggc cggcaacccg    840

atcctggccc aggctgttgt gagcccgcaa gcggcccgca gtgcggcagc ccggaactgc    900

gatgaacaca tgttctggga tcaggtgcac ccgactgcga cggtgcacaa ggcgatgggg    960

gagcgggtcg ccgctttcat cgaacagcat tacgagttta ttcgtcgctg a           1011
```

<210> SEQ ID NO 16
<211> LENGTH: 960
<212> TYPE: DNA
<213> ORGANISM: Escherichia coli

<400> SEQUENCE: 16

```
atggtggaac gcccgagttt ctcacgtatt gttatgtttg gtgatagtct gtccgacacc     60

ggcaaaatgt acaagaaaat gaaaggttat ctgccgagca gcccgccgta ttacgaaggt    120

cgttttagca atggtccggt gtggctggaa cgtctgcgtg atgaacattt cccgggtctg    180

caactggcaa atgaagctga aggcggtgcc acggcagttg cttataacaa actgggctgg    240

ctgaattttt gggcgtggga cccgaaatat caggtcatta acaatctgga ttacgaaatc    300

gaccaattcc tggccaaaga ttcactgcgt ccggatgacc tggtggttat ttgggttggt    360
```

-continued

```
gcgaacgatt atctggccta cggctggaat caggaaaaag atgcagaccg cgtcattgaa    420
accatccgtc tggcatccaa ccgcctggtg ctgaatggtg ctcagcaaat tctgctgttt    480
aacatcccgg atctgggccg tacgccgtca gcgaacagca tgaaagtcgt ggaccaggtg    540
cgccatgttg cctcatatca caaccaacgt ctgctgaatc tgtcgcgcga actggccccg    600
ctgggtatcg tcaaaatgtt cgaagtggat aaacagttcg acgaaatggt gggtgatccg    660
caaaaatttg gcctgagcga catcgaacat gcatgctatg gcggtggcta cctgtggaaa    720
ccgttcagcg atgcttctga agccccggca ctgtctgttc cggaacgtct ggcagttgct    780
ggtaacccga tcctggccca ggcagttgtc agtccgcaag ccgcacgttc cgcagctgcg    840
cgtaattgtg atgaacacat gttctgggac caggtgcatc cgaccgcgac ggttcacaaa    900
gcgatgggcg aacgtgtggc agcatttatt gaacaacatt atgaatttat ccgtcgttaa    960
```